(12) United States Patent
Rives et al.

(10) Patent No.: US 9,206,390 B2
(45) Date of Patent: *Dec. 8, 2015

(54) METHODS TO CONTROL PROTEIN HETEROGENEITY

(71) Applicant: ABBVIE INC., North Chicago, IL (US)

(72) Inventors: Lisa M. Rives, Natick, MA (US); Cornelia Bengea, Auburn, MA (US); Xiaobei Zeng, Carolina, PR (US)

(73) Assignee: AbbVie, Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/804,220

(22) Filed: Mar. 14, 2013

(65) Prior Publication Data

US 2014/0065710 A1 Mar. 6, 2014

Related U.S. Application Data

(60) Provisional application No. 61/696,219, filed on Sep. 2, 2012.

(51) Int. Cl.
| | | |
|---|---|---|
| *C12N 5/00* | (2006.01) | |
| *C07K 16/00* | (2006.01) | |
| *C07K 16/24* | (2006.01) | |

(52) U.S. Cl.
CPC ............. *C12N 5/0018* (2013.01); *C07K 16/00* (2013.01); *C07K 16/241* (2013.01); *C07K 2317/41* (2013.01); *C12N 2510/02* (2013.01)

(58) Field of Classification Search
CPC ...... C12N 5/10; C12N 5/0018; C12N 5/1002; A61K 2039/505
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,927,762 A | 5/1990 | Darfler |
| 4,933,435 A | 6/1990 | Ngo |

(Continued)

FOREIGN PATENT DOCUMENTS

| | | |
|---|---|---|
| CN | 1299370 A | 6/2001 |
| CN | 1563090 A | 1/2005 |

(Continued)

OTHER PUBLICATIONS

Burteau et al., (In Vitro Cell Dev Biol—Animal. Jul./Aug. 2003. 39:291-296).*

(Continued)

*Primary Examiner* — Cherie M Stanfield
(74) *Attorney, Agent, or Firm* — McCarter & English, LLP; Maria Laccotripe Zacharakis; Maneesh Gulati

(57) ABSTRACT

The instant invention relates to the field of protein production, and in particular to compositions and processes for controlling and limiting the heterogeneity of proteins expressed in host cells.

41 Claims, 60 Drawing Sheets

Example 1: Effect of yeast, soy, or wheat hydrolysate addition to CDM GIA-1 in adalimumab-producing CHO cell line #1 on (A) Culture growth, (B) Culture viability, and (C) Harvest titer Example 1: Effect of yeast, soy, or wheat hydrolysate addition to CDM GIA-1 in adalimumab-producing CHO cell line #1 on (A) Culture growth, (B) Culture viability, and (C) Harvest titer

(56) References Cited

U.S. PATENT DOCUMENTS

| | | |
|---|---|---|
| 4,968,615 A | 11/1990 | Koszinowski et al. |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A * | 7/2000 | Salfeld et al. ............... 424/133.1 |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 | 2/2008 | Schilling et al. |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 2002/0045207 A1 | 4/2002 | Krummen et al. |
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |

(56) References Cited

U.S. PATENT DOCUMENTS

| | | |
|---|---|---|
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0153846 A1 | 7/2006 | Krause et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |

(56) References Cited

U.S. PATENT DOCUMENTS

| | | |
|---|---|---|
| 2013/0205604 A1 | 8/2013 | Esenwein et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |
| 2014/0314745 A1 | 10/2014 | Rives et al. |
| 2014/0377275 A1 | 12/2014 | Neu et al. |

FOREIGN PATENT DOCUMENTS

| | | | |
|---|---|---|---|
| DE | 3631229 | A1 | 3/1988 |
| EP | 0101681 | A1 | 3/1984 |
| EP | 0173177 | A1 | 3/1986 |
| EP | 0186833 | A2 | 7/1986 |
| EP | 0212489 | A2 | 3/1987 |
| EP | 0351789 | A2 | 1/1990 |
| EP | 0366043 | A1 | 5/1990 |
| EP | 0460426 | B1 | 12/1991 |
| EP | 0481791 | A2 | 4/1992 |
| EP | 0492448 | A1 | 7/1992 |
| EP | 0523949 | A1 | 1/1993 |
| EP | 0612251 | A1 | 8/1994 |
| EP | 0614984 | A2 | 9/1994 |
| EP | 0659766 | A1 | 6/1995 |
| EP | 0746398 | A1 | 12/1996 |
| EP | 0764719 | A2 | 3/1997 |
| EP | 0956873 | A2 | 11/1999 |
| EP | 0956875 | A2 | 11/1999 |
| EP | 1075488 | A1 | 2/2001 |
| EP | 1174148 | A1 | 1/2002 |
| EP | 1221476 | A2 | 7/2002 |
| EP | 1254666 | A1 | 11/2002 |
| EP | 1308455 | A2 | 5/2003 |
| EP | 1308456 | A2 | 5/2003 |
| EP | 1418967 | A2 | 5/2004 |
| EP | 1568388 | A1 | 8/2005 |
| EP | 1745141 | A1 | 1/2007 |
| EP | 1851305 | A1 | 11/2007 |
| EP | 2080809 | A1 | 7/2009 |
| EP | 2144929 | A1 | 1/2010 |
| EP | 2152856 | A1 | 2/2010 |
| EP | 2213726 | A1 | 8/2010 |
| EP | 2357250 | A2 | 8/2011 |
| EP | 2495307 | A1 | 9/2012 |
| EP | 2528002 | A2 | 11/2012 |
| EP | 2574677 | A1 | 4/2013 |
| GB | 2160530 | A | 12/1985 |
| GB | 2279077 | A | 12/1994 |
| JP | 7289288 | A | 11/1995 |
| WO | WO-87/00195 | A1 | 1/1987 |
| WO | WO-90/03430 | A1 | 4/1990 |
| WO | WO-90/05144 | A1 | 5/1990 |
| WO | WO-91/02078 | A1 | 2/1991 |
| WO | WO-91/09967 | A1 | 7/1991 |
| WO | WO-92/01047 | A1 | 1/1992 |
| WO | WO-92/11383 | A1 | 7/1992 |
| WO | WO-92/16553 | A1 | 10/1992 |
| WO | WO-93/06213 | A1 | 4/1993 |
| WO | WO-94/02602 | A1 | 2/1994 |
| WO | WO-94/08619 | A1 | 4/1994 |
| WO | WO-94/25585 | A1 | 11/1994 |
| WO | WO-94/26910 | A1 | 11/1994 |
| WO | WO-94/29347 | A1 | 12/1994 |
| WO | WO-9511317 | A1 | 4/1995 |
| WO | WO-95/23813 | A1 | 9/1995 |
| WO | WO-96/33208 | A1 | 10/1996 |
| WO | WO-96/33735 | A1 | 10/1996 |
| WO | WO-96/34096 | A1 | 10/1996 |
| WO | WO-199704801 | A1 | 2/1997 |
| WO | WO-97/13852 | A1 | 4/1997 |
| WO | WO-97/29131 | A1 | 8/1997 |
| WO | WO-98/23645 | A1 | 6/1998 |
| WO | WO-98/24883 | A2 | 6/1998 |
| WO | WO-98/24884 | A1 | 6/1998 |
| WO | WO-98/24893 | A2 | 6/1998 |
| WO | WO-9823645 | A1 | 6/1998 |
| WO | WO-98/50433 | A2 | 11/1998 |
| WO | WO-9856418 | A1 | 12/1998 |
| WO | WO-99/32605 | A1 | 7/1999 |
| WO | WO-99/57134 | A1 | 11/1999 |
| WO | WO-99/57246 | A1 | 11/1999 |
| WO | WO-0003000 | A2 | 1/2000 |
| WO | WO-01-44442 | A1 | 6/2001 |
| WO | WO-0147554 | A1 | 7/2001 |
| WO | WO-01-59069 | A1 | 8/2001 |
| WO | WO-0177362 | A1 | 10/2001 |
| WO | WO-02/12502 | A2 | 2/2002 |
| WO | WO-0212501 | A2 | 2/2002 |
| WO | WO-03/045995 | A2 | 6/2003 |
| WO | WO-03/059935 | A2 | 7/2003 |
| WO | WO-03/066662 | A2 | 8/2003 |
| WO | WO-2004008100 | A2 | 1/2004 |
| WO | WO-2004/058944 | A2 | 7/2004 |
| WO | WO-2004058800 | A2 | 7/2004 |
| WO | WO-2004/097006 | A1 | 11/2004 |
| WO | WO-2005042569 | A1 | 5/2005 |
| WO | WO-2005/082483 | A1 | 9/2005 |
| WO | WO-2006/043895 | A1 | 4/2006 |
| WO | WO-2006045438 | A1 | 5/2006 |
| WO | WO-2006/099308 | A2 | 9/2006 |
| WO | WO-2006/110277 | A1 | 10/2006 |
| WO | WO-2007/087384 | A2 | 8/2007 |
| WO | WO-2007/117490 | A2 | 10/2007 |
| WO | WO-2008/033517 | A2 | 3/2008 |
| WO | WO-2008-057240 | A2 | 5/2008 |
| WO | WO-2008068879 | A1 | 6/2008 |
| WO | WO-2008087184 | A2 | 7/2008 |
| WO | WO-2008121616 | A2 | 10/2008 |
| WO | WO-2008135498 | A2 | 11/2008 |
| WO | WO-2009/027041 | A1 | 1/2009 |
| WO | WO-2009023562 | A2 | 2/2009 |
| WO | WO-2009058769 | A1 | 5/2009 |
| WO | WO-2009/073569 | A2 | 6/2009 |
| WO | WO-2009135656 | A1 | 11/2009 |
| WO | WO-2010036443 | A1 | 4/2010 |
| WO | WO-2010/043703 | A1 | 4/2010 |
| WO | WO-2010122460 | A1 | 10/2010 |
| WO | WO-2010/129469 | A1 | 11/2010 |
| WO | WO-2010/127069 | A1 | 11/2010 |
| WO | WO-2011005773 | A2 | 1/2011 |
| WO | WO-2011009623 | A1 | 1/2011 |
| WO | WO-2011-019619 | A1 | 2/2011 |
| WO | WO-2011/015926 | A1 | 2/2011 |
| WO | WO-2011024025 | A1 | 3/2011 |
| WO | WO-2011044180 | A1 | 4/2011 |
| WO | WO-2011/073235 | A1 | 6/2011 |
| WO | WO-2011069056 | A2 | 6/2011 |
| WO | WO-2011098526 | A1 | 8/2011 |
| WO | WO-2011110598 | A1 | 9/2011 |

(56) References Cited

FOREIGN PATENT DOCUMENTS

| WO | WO-2011/133886 A2 | 10/2011 |
|---|---|---|
| WO | WO-2011127322 A1 | 10/2011 |
| WO | WO 2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012050175 A1 | 4/2012 |
| WO | WO-2012051147 A1 | 4/2012 |
| WO | WO-2012/065072 A2 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013-011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |

OTHER PUBLICATIONS

BD Bioscience Product Description for BBL Phytone Peptone (Advanced Processing, Third Edition) (Sep. 23, 2010), (www.bdbiosciences.com/external_files/Doc_Recon_2.0/ab/others/Phytone_Soytone.pdf), (last accessed Jan. 8, 2015).*
Kwon et al., (Enzyme Microb Technol. 2000;26:209-215).*
Andersen et al. (Curr Opin Biotech 1994 5:546-549).*
Goochee et al., (Biotechnology, Dec. 1991 9:1346-1355).*
Parekh et al., (TIBTECH, May 1989 7:117-122).*
Hossler et al., (Glycobiology. 2009;19(9):936-949).*
"Genentech unveils production capacity hikes," in-Pharma Technologist.com Jun. 28, 2005, pp. 1-2.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS.
"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS.
"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS.
"Plaintiffs' Memorandum in Support of Their Motion for Partial Summary Judgment", dated Aug. 1, 2013 and submitted by plaintiff in Civil Action No. 09-40089-FDS.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS.

Abraham, E., et al., "Efficacy and Safety of Monoclonal Antibody to Human Tumor Necrosis Factor α in Patients with Sepsis Syndrome," JAMA, vol. 273(12):934-941 (1995).
Adams. et al. J. Am. Acad. Dermatol 2004;51 :660-2.
Altamirano, C., et al., "Strategies for fed batch cultivation of t-PA producing CHO cells: substitution of glucose and glutamine and rational design of culture medium", J. Biotechn. 110:171-179, 2004.
Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.
Avgerinos et al. (GAb '04 Abstracts—GE Healthcare Life Sciences, France Oct 3-5, 2004, pp. 15-16 published 2005).
Azevedo et al., "Integrated Process for the Purification of Antibodies Combining Aqueous Two-Phase Extraction, Hydrophobic Interaction Chromatography and Size-Exclusion Chromatography", Journal of Chromatography (2008) 1213(2): 154-161.
Ballez, J.S. et al., "Plant protein hydrolysates support CHO-320 cells proliferation and recombinant IFN-[gamma] production in suspension and inside microcarriers in protein-free media", Cytotechnology 44:3, 103-114, 2004.
Barbuto, J. et al. "Production of Neutralizing Antibodies to Tumor Necrosis Factor by Human Tumor-Infiltrating B Lymphocytes" Proc. Am. Assoc. Cancer Res,. 34:487, Abstr. 2904 (1993).
Biblia, T.A. et al., "In Pursuit of the Optimal Fed-Batch Process for Monoclonal Antibody Production", Biotechnol. Prog 11(1):1-13, Jan.-Feb. 1995.
Birch, Jr. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Boekstegers, P., et al., "Repeated administration of a F(ab')2 fragment of an anti-tumor necrosis factor alpha monoclonal antibody in patients with severe sepsis: effects on the cardiovascular system and cytokine levels," Shock, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" Cell. Immunol., 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" Cell. Immunol., 152:569-81 (1993).
Brekke, O. et al., "Therapeutic Antibodies for Human Diseases at the Dawn of the Twenty-first Century," Nature, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. *;455-458 (1997).
Bruggemann, M., Neuberger, M.S., "Strategies for expressing human antibody repertoires in transgenic mice," Immunol. Today 17:391-397 (1996).
Cai B, et al. "C-Terminal Lysine Processing of Human Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.

(56) References Cited

OTHER PUBLICATIONS

Carter et al., "Humanization of an anti-p185HER2 antibody for human cancer therapy," Proc. Nat. Acad. Sci 89:4285-4289 (1992).

Chang KH, et al., "N-Acetylcysteine Increases the Biosynthesis of Recombinant EPO in Apoptotic Chinese Hamster Ovary Cells", Free Radic Res. 30(2):85-91, 1999.

Charter, Edward A., "A New Process for the Separation and Purification of Egg Yolk; Antibodies," BASc., The University of British Columbia; A Thesis; Apr. 1993.

Choo et al. "High-level production of a monoclonal antibody in murine myeloma cells by perfusion culture using a gravity settler" Biotechnology Progress, vol. 23, No. 1, Jan. 1, 2007, 225-231.

Chow, A. et al. "Effect of monoclonal antibody on human tumor necrosis factor (TNF MAb) on TNFα, IL-1β, and IL-6 levels in patients with sepsis syndrome" Clinical Research, 42:2 299A (1994).

Chua, FKF et al., "Hyper-stimulation of monoclonal antibody production by high osmolarity stress in eRDF medium", J. Biotechnology 37(3):265-275, Nov. 15, 1994.

Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.

Chung et al., "Utilization of Lysozyme Charge Ladders to Examine the Effects of Protein Surface; Charge Distribution on Binding Affinity in Ion Exchange Systems," Langmuir 26(2): 759-768 (2010).

Chung et al., "Cetuximab-Induced Anaphylaxis and IgE Specific for Galactose-α-1, 3-Galactose", N. Engl. J. Med., 358:11, pp. 1109-1117 (2008).

Cleland, J. et al., "A Specific Molar Ratio of Stabilizer to Protein is Required for Storage Stability of a Lyophilized Monoclonal Antibody," Journal of Pharmaceutical Sciences, vol. 90(3):310-321 (2001).

Clincke, M. et al., "Effect of surfactant pluronic F-68 on CHO cell growth, metabolism, production, and glycosylation of human recombinant INF-γ in mild operating conditions," Biotechnol. Prog. 27(1): 181-190, 2011.

Cohen, J., et al., "Intersept: An international, multicenter, placebo-controlled trial of monoclonal anitbody to human tumor necrosis factor-α in patients with sepsis," Crit Care Med, vol. 24(9):1431-1440 (1996).

Cox, J. et al., "A directory of human germ-line Vκ segments reveals a strong bias in their usage" Eur. J. Immunol., 24(2):827-36 (1994).

Cromwell (GAB'04 Abstracts—GE Healthcare Life Sciences, Franc Oct. 3-5, 2004, pp. 17-18 published 2005).

Daugherty, et al. Formulation and Delivery Issues for Monoclonal Antibody Therapeutics. Advanced Drug Delivery Reviews, 2006. vol. 58, pp. 686-706.

Davies et al., "Antibody VH domains as small recognition units." Biotechnology, 13:475-479 (1995).

Department of Surgery, University of Toronto, Annual Report (1998-1999)(348 pages).

DePhillips et al., "Determinants of protein retention characteristics on cation-exchange adsorbents,"; Journal of Chromatograph A, 933:57-72 (2001).

deZongotita et al., "Phosphate feeding improves high-cell-concentration NS0 myeloma cell culture performance for monoclonal antibody production" Biotechnology and Bioengineering. 2000, 69: 566-576.

Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.

Dolezal, et al., "Escherichia coli Expression of a Bifunctional Fab-peptide Epitope Reagent for the Rapid Diagnosis of HIV-1 and HIV-2", Immunotechnology, 1:197-209 (1995).

Doring, E., "Identification and Characterization of a TNFa Antagonist Derived from a Monoclonal Antibody" (1994) Mol. Immunol .31(14): 1059-1067.

Elliot et al., "Repeated therapy with monoclonal antibody to tumour necrosis factor α (cA2) in patients with rheumatoid arthritis" (1994) Lancet, 344:1125-1127.

Elliot, "Treatment of rheumatoid arthritis with chimeric monoclonal antibodies to tumor necrosis factor α" (1993) Arthritis & Rheumatism, 36(12):1681-1690.

Erbitux (cetuximab) label, Revised Aug. 2013.

Ewert et al., "Biophysical Properties of Human Antibody Variable Domains," J. Mol. Biol. 324: 531-553 (2003).

Exhibit dated Aug. 1, 2013 and cited by defendant in Civil Action No. 09-40089-FDS providing the Jun. 23, 2009 trial transcript of the PM session in the matter of Centocor, et al. v. Abbott Laboratories.

Exhibit dated Aug. 1, 2013 and cited by defendant in Civil Action No. 09-40089-FDS providing the trial transcript in the matter of Abbott Laboratories, et al. v. The Mathilda and Terrance Kennedy Institute, S.D.N.Y.

Exhibit dated Aug. 1, 2013 and cited by plaintiff in Civil Action No. 09-40089-FDS providing excerpts from the File History of U.S. Appl. No. 12/578,487.

Exhibit dated Aug. 1, 2013 and cited by defendant in Civil Action No. 09-40089-FDS providing the Jun. 24, 2009 trial transcript of the AM session in the matter of Centocor, et al. v. Abbott Laboratories, E.D. TX.

Exhibit dated Aug. 1, 2013 and cited by defendant in Civil Action No. 09-40089-FDS providing the Sep. 20, 2012 Day 8 trial transcript in the matter of Abbott v. Centocor Ortho Biotech Inc., D. MA.

Exhibit dated Aug. 1, 2013 and cited by plaintiff in Civil Action No. 09-40089-FDS providing Declaration by Jochen Salfeld, dated Jan. 17, 2013.

FDA Package insert for Adalimumab, Sep. 26, 2003, pp. 1-18.

Feldmann, "Anti-TNF-alpha Therapy of Rheumatoid Arthritis: What Have We Learned?" (2001) Annu. Rev. Immunol., 19:163-196.

Figini, "In Vitro assembly of Repertoires of Antibody Chains on the Surface of Phage by Renaturation" (1994) J. Mol. Biol., 239:68-78.

Fishwild et al., "High-avidity human IgG kappa monoclonal antibodies from a novel strain of minilocus transgenic mice" (1996) Nature Biotechnology, 14:845-851.

Fomsgaard, "Auto-antibodies to Tumor Necrosis Factor α in Healthy Humans and Patients with Inflammatory Diseases and Gram-Negative Bacterial Infections" (1989) Scand. J. Immunol. 30:219-23.

Foote, J., "Antibody framework residues affecting the conformation of the hypervariable loops" (1992) J. Mol. Biol., 224(2):487-499.

Freitag et al., "Displacement chromatography in biotechnological downstream processing," J. Chromatography, (1995) 691(1):101-112.

Gagnon et al., "A Systematic Approach to the Purification of Monoclonal Antibodies," LC-GC 11 (1):26-34 (1993).

Gatto, B. "Biologics targeted at TNF: design, production and challenges", Reumatismo 58(2):94-103, 2006.

Genbank Entry for CHO Cathepsin L., EGW13555, Aug. 25, 2011, pp. 1-2.

Ghaderi, et al., "Implications of the Presence of N-glycolylneuraminic acid in Recombinant Therapeutic Glycoproteins", Nature Biotechnology, 28(8):863-868 (2010).

Ghaderi, et al., "Production platforms for biotherapeutic glycoproteins. Occurrence, impact, and challenges of non-human sialylation", Biotechnology and Genetic Engineering Reviews, 28:147-176 (2012).

Gonzalez et al. "Purification of Lactic Acid from Fermentation Broths by Ion-Exchange Resins" Ind. Eng. Chem. Res. 45:3243 (2006).

Graf et al., "Ion exchange resins for the purification of monoclonal antibodies from animal cell culture" Bioseparation 4 (1) :7-20 (Feb. 1994). ;4 (1) :7-20 (Feb. 1994).

Gram et al., "In vitro selection and affinity maturation of antibodies from a naive combinatorial immunoglobulin library" (1992) PNAS, 89:3576-3580.

Gramer et al., "Glycosidase Activities of the 293 and NS0 Cell Lines, and of an Antibody-Producing Hybridoma Cell Line", Biotechnology and Bioengineering, 43:423-428 (1994).

Green et al., "Antigen-specific human monoclonal antibodies from mice engineered with human Ig heavy and light chain YACs" (1994) Nature Genetics, 7:13-21.

(56) References Cited

OTHER PUBLICATIONS

Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grunberg, J. et al., "High-Yield Production of Recombinant Antibody Fragments in HEK-293 Cells Using Sodium Butyrate", BioTechniques 34(5):968-972, May 2003.
Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Harlow and Lane, Antibodies A Laboratory Manual, Purification of Antibodies by using a; Deae-matrix (Batch), Storing and Purifying Antibodies; Chapter 8: 302-303 (1988).
Harris et al. "Processing of C-terminal lysine and argnine residues of proteins isolated from mammalian cell culture" Journal of Chromatography, (1995) 705; 129-123.
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor -alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(11):484-490 (2003).
Hoogenboom et al., "By-passing immunisation : Human antibodies from synthetic repertoires of germline VH gene segments rearranged in vitro" (1992) *J. Mol. Biol.*, 227:381-388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler P. et al., "Improvement of mammalian cell culture performance through surfactant enabled concentrated feed media," Biotechnol. Prog. 29(4): 1023-1033, 2013.
www.cygnustechnologies.com/product_detail/host-cell-protein-antibodies/anti-cho-h...CYGNUS Technologies, Anti-CHO HCP (Apr. 18, 2012).
Huang et al. "Effects of anti-TNF monoclonal antibody infusion in patients with hairy cell leukaemia" (1992) *Br. J. Haematol.*, 81(2):231-234.
Hui et al., "Recovery and purification process development for monoclonal antibody production," MABS (2010) 2(5):480-499.
Humira (adalimumab) label, Revised Sep. 2013.

Huse, "Generation of a large combinatorial library of the immunoglobulin repertoire in phage lambda" (1989) *Science*, 246:1275-81.
International Preliminary Report on Patentability for Application No. PCT/US07/08359, dated Dec. 12, 2011.
International Preliminary Report on Patentability for Application No. PCT/US2011/060388, dated May 30, 2012.
International Search Report and Written Opinion for Application No. PCT/US2008/085066, dated May 12, 2009.
International Search Report and Written Opinion for Application No. PCT/US2010/033387, dated Aug. 7, 2012.
International Search Report and Written Opinion for Application No. PCT/US2013/031380, dated Feb. 5, 2014.
International Search Report and Written Opinion for Application No. PCT/US2013/041954, dated Dec. 17, 2013.
International Search Report and Written Opinion for Application No. PCT/US2013/041958, dated Dec. 17, 2013.
International Search Report and Written Opinion for Application No. PCT/US2013/065720, dated Dec. 16, 2013.
International Search Report and Written Opinion for Application No. PCT/US2013/065797, dated Nov. 26, 2013.
International Search Report for Application No. PCT/IB03/04502, dated May 26, 2004.
International Search Report for Application No. PCT/US2011/060388 dated May 30, 2012.
International Search Report for Application No. PCT/US2013/031352, Dated Apr. 25, 2013.
International Search Report for Application No. PCT/US2013/031389, Dated Jun. 3, 2013.
International Search Report for Application No. PCT/US2013/031485, Dated Jun. 25, 2013.
International Search Report for Application No. PCT/US2013/031681, Dated Jun. 14, 2013.
Invitation to Pay Additional Fees for International Application No. PCT/US2013/031380, Dated Nov. 28, 2013.
Jakobovits, A., "Production of fully human antibodies by transgenic mice" (1995) *Curr. Op. Biotechnol.*, 6:561-566.
Jespers, "Guiding the Selection of Human Antibodies from Phage Display Repertoires to a Single Epitope of an Antigen" (1994) *Bio/Technology*, 12:899-903.
Johnson et al. (Archives of Biochemistry and Biophysics 444 (2005) 7-14).
Kalyanpur, M., "Downstream Processing in the Biotechnology Industry" Molecular Biotechnology, vol. 22:87-98 (2002).
Karampetsou et al. (Q J Med 2010; 103:917-928).
Kaschak et al: "Characterization of the basic charge variants of a human IgG1: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor -alpha monoclonal antibody" (2000) *Ann. Rheum. Dis.*, 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgG1: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Knight et al., "Construction and initial characterization of a mouse-human chimeric anti-TNF antibody" (1993) *Mol. Immunol.*, 30(16):1443-1453.
Kopaciewicz et al., "Retention Model for High-Performance Ion-Exchange Chromatography,"; Journal of Chromatography, 266:3-21 (1983).

(56) References Cited

OTHER PUBLICATIONS

Lerner, "Antibodies without immunization" (1992) *Science*, 258:1313-1314.

Lewis, "Use of alanine scanning mutagenesis to improve the affinity of an anti gp120 (HIV) antibody" (1994) *J. Cell. Biochem.*, 18D:215.

Li, F. et al., "Current Therapeutic Antibody Production and Process Optimization" BioProcessing Journal, vol. 4(5):23-30 (2005).

Lifely et al., "Glycosylation and Biological Activity of CAMPATH-1H Expressed in Different Cell Lines and Grown Under Different Culture Conditions", *Glycobiology*, 5(8):813-822 (1995).

Logan, John S. "Transgenic Animals: Beyond 'Funny Milk'", *Current Opinion in Biotechnology*, 4:591-595 (1993).

Lonberg et al., "Antigen-specific human antibodies from mice comprising four distinct genetic modifications" (1994) *Nature*, 368:856-859.

Lonberg et al., "Human Antibodies from Transgenic Mice" (1995) *Int. Rev. Immunol.*, 13:65-93.

Low, "Mimicking Somatic Hypermutation: Affinity Maturation of Antibodies Displayed on Bacteriophage Using a Bacterial Mutator Strain" (1996) *J. Mol. Biol.*, 260:359-368.

Low, Nigel: thesis extract (1996) *Cambridge University*.

Luo et al., "Understanding of C-terminal lysine variants in antibody production using mammalian cells" Abstract of papers, ACS, Anaheim, CA, US, Mar. 2011.

Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.

Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.

Ma, et al., "Generation and Assembly of Secretory Antibodies in Plants", *Science*, 268:716-719 (1995).

Maeda, et al., "Analysis of Nonhuman N-Glycans as the Minor Constituents in Recombinant Monoclonal Antibody Pharmaceuticals", *Anal. Chem.*, 84:2373-2379 (2012).

Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".

Marks et al., "Human antibody fragments specific for human blood group antigens from a phage display library" (1993) *Bio/Technology*, 11:1145-1150.

Marks et al., "Molecular evolution of proteins on filamentous phage. Mimicking the strategy of the immune system" (1992) *J Biol. Chem.* 267:16007-16010.

Marks, "By-passing immunization: Human antibodies from V-gene libraries displayed on phage" (1991) *J. Mol. Biol.*, 222:581-597.

Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.

Marks, JD., "By-Passing Immunization: Building High Affinity Human Antibodies by Chain Shuffling" (1992) *Biotechnology*, 10:779-783.

Martin, A.C.R. "Accessing the Kabat antibody sequence database by computer" (1996)*PROTEINS: Structure, Function and Genetics*, 25:130-133.

Martinelle, K. et al., Cells and Culture, Proceedings of the 20th ESACT Meeting v4 819-822, Jun. 17-20, 2007.

Medynski, "Phage Display: All Dressed Up and Ready to Role" (1994) *Bio/Technology*, 12:1134-1136.

Mendez et al., "Functional transplant of megabase human immunoglobulin loci recapitulates human antibody response in mice" (1997) *Nature Genetics*, 15:146-156.

Meuwly, F. et al., "Conversion of a CHO cell culture process from perfusion to fed-batch technology without altering product quality", J.Biotechn. 123:106-116, 2006.

Miller et al. "Characterization of site-specific glycation during process development of a human therapeutic monoclonal antibody" Journal of Pharmaceutical Sciences, vol. 100, No. 7, Jul. 2011, 2543-2550.

Millipore, "Pellicon 2 Filters and Holders," 2003, pp. 1-8.

Moore, A., et al., "Effects of temperature shift on cell cycle, apoptosis and nucleotide pools in CHO cell batch cultures", Cytotechnology, 23:47-54, 1997.

Möller, Monoclonal antibodies to human tumor necrosis factor α: in vitro and vivo application (1990) *Cytokine*, 2(3):162-69.

Neuberger M. et al., "Mice perform a human repertoire" (1997) *Nature*, 386:25-26.

Ngo et al., "Kosmotropes enhance the yield of antibody purified by affinity chromatography using immobilized bacterial immunoglobulin binding proteins," Journal of Immunoassay & Immunochemistry, (2008) 29(1):105-115.

Nilsson, "Antibody engineering" (1995) *Current Opinion in Structural Biology*, 5:450-456.

Nogal, B., Chhiba, K. and Emery, J. C. (2012), Select host cell proteins coelute with monoclonal antibodies in protein a chromatography. Biotechnol Progress, 28: 454-458.

Noguchi et al., "Failure of Human Immunoresponse to N-Glycolylneuraminic Acid Epitope Contained in Recombinant Human Erythropoietin", *Nephron*, 72:599-603 (1996).

Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).

Oh, D-K. et al., "Increased erythritol production in fed-batch cultures of *Torula* sp. by controlling glucose concentration", J. Industrial Microb. & Biotechn. 26(4): 248-252, 2001.

Oh, SKW, et al., "Substantial Overproduction of Antibodies by Applying Osmotic Pressure and Sodium Butyrate", Biotechn. Bioengin. 42(5):601-610, 1993.

Osbourn, "From rodent reagents to human therapeutics using antibody guided selection" (2005) *Methods*, 36(1):61-68.

Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.

Perchiacca et al., "Aggregation-resistance domain antibodies engineered with charged mutations; near the edges of the complementarity-determining regions," Protein Engineering Design & Selection, 25:10 (591-601) 2012.

Pietersz et al., "In vitro and in vivo Antitumor Activity of a Chimeric anti-CD19 Antibody", *Cancer Immunol. Immunother.*, 41:53-60 (1995).

Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.

Potter et al., "Antibody Production in the Baculovirus Expression System", *Intern. Rev. Immunol.*, 10:103-112 (1993).

Poul et al., "Design of Cassette Baculovirus Vectors for the Production of Therapeutic Antibodies in Insect Cells", *Immunotechnology*, 1:189-196 (1995).

Queen, C., "A humanized antibody that binds to the interleukin 2 receptor" (1989) *Proc. Natl. Acad. Sci. USA*, 86(24):10029-10033.

Rader et al. "A phage display approach to rapid antibody humanization: Designed combinatorial V gene libraries" (1998) *Proc Natl Acad Sci USA*, 95:8910-8915.

Raju, TS. "Glycosylation Variations with Expression Systems and Their Impact on Biological Activity of Therapeutic Immunoglobulins", *BioProcess International.*, 44-53 (2003).

Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.

Reichert JM., et al., "Monoclonal antibody successes in the clinic", Nature Biotech. 23(9):1073-1078, 2005.

Reinhart, "Assessment of the safety and efficacy of the monoclonal anti-tumor necrosis factor antibody-fragment, MAK 195F, in

(56) References Cited

OTHER PUBLICATIONS patients with sepsis and septic shock: a multicenter, randomized, placebo-controlled, dose-ranging study" (1996) *Crit. Care Med.*, 24(5):733-742.

Rheinwald JG, et al., "Growth of Cultured Mammalian Cells on Secondary Glucose Sources", Cell, 287-293, 1974.

Ridder et al., "Generation of Rabbit Monoclonal Antibody Fragments from a Combinatorial Phage Display Library and Their Production in Yeast *Pichia pastoris*", *Biotechnology*, 13:255-260 (1995).

Riechmann, "Phage display and selection of a site-directed randomized single-chain antibody Fv fragment for its affinity improvement" (1993) *Biochemistry*, 32(34):8848-8855.

Routier, F. H. et al.: "The glycosylation pattern of a humanized IgGl antibody(D1.3) expressed in CHO cells", Glycoconjugate Journal, Chapman & Hall, GB, vol. 14, No. 2, Jan. 1, 1997, pp. 201-207.

Rube et al. (Int. J. Radiation Oncology Biol. Phys., vol. 56, No. 5, pp. 1414-1425,2003).

Rudikoff et al., "Single amino acid substitution altering antigen-binding specificity" (1982) *Proc. Natl. Acad. Sci. USA*, 70:1979-1983.

Salfeld, "Development of a Fully Human Antibody to TNF by Phage Display Technology," IBC Conference, *Antibody Engineering*, San Diego (Dec. 1996), pp. 1-36.

Sandadi, S. et al., "Heuristic Optimization of Antibody Production by Chinese Hamster Ovary Cells", Biotech. Progress, American Institute of Chem. Engineers: 21(5): 1537-1542, 2005.

Sandhu, J. "Protein engineering of antibodies" (1992) *Critical Reviews in Biotechnology*, 12:437-462.

Santora et al., "Characterization of recombinant human monoclonal tissue necrosis factor-alpha antibody using cation exchange HPLC and capillary isoelectric focusing," Analytical Biochemistry, (1999) 275:98-108.

Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.

Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.

Schiestl et al. "Acceptable changes in quality attributes of glycosylated biopharmaceuticals" Nature Biotechnology, 29(4), 310-312 (2011).

Schwieterman, "Immunosuppression in Combination with Monoclonal Antibodies" in Biologic Agents in Autoimmune Disease (Mar. 2-4, 1995).

Senczuk et al. "Hydrophobic interaction chromatography in dual salt system increases protein binding capacity" Biotechnology and Bioengineering, 103(5), 930-935 (2009).

Seresht et al., "The impact of phosphate scarcity on pharmaceutical protein production in *S. cerevisiae*: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", *Anal. Biochem.*, 247(1):102-110 (1997).

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shih, "Effects of Anions on the Deamidation of Soy Protein". Journal of Food Science. 1991, 56: 452-454.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.

Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.

Tan et al. (Biotechnol. Appl. Biochem. (1999) 30, 59-64).

Taylor et al.,"Human immunoglobulin transgenes undergo rearrangement, somatic mutation and class switching in mice that lack endogenous IgM" (1994) *Int. Immunol.*, 6:579-591.

Teichmann, S. Declaration dated Dec. 7, 2010 from opposition proceedings in EP 0929578.

The MW Calculator available at the Sequence Manipulation Suite (see bioinformatics.org/sms2/index.html), downloaded Feb. 25, 2014.

The pI Calculator available at the Sequence Manipulation Suite (see ://bioinformatics.org/sms2/index.html>), downloaded Feb. 25, 2014, p. 1).

The Statement on a Nonproprietary Name Adopted by the USAN Council for Adalimumab, p. 1, downloaded on May 19, 2011 from http://www.ama-assn.org/resources/doc/usan/adalimumab.doc.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjugate Journal 21 :343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Lent PL, et al. "The impact of protein size and charge on its retention in articular cartilage" J Rheumatol. Aug. 1987;14(4):798-805.

(56) References Cited

OTHER PUBLICATIONS

Varasteh et al. Optimization of Anti-Rh D Immunoglobulin Stability in the Lyphiliization Process. Iranian Journal of Basic Medical Sciences, Spring 2008, vol. 11, No. 1. pp. 55-61.

Vaughan, "Human antibodies by design" (1998) *Nature Biotechnology*, 16:535-539.

Wagner et al., "Antibodies generated from human immunoglobulin miniloci in transgenic mice" (1994) *Nucl. Acids Res*. 22:1389-1393.

Wagner et al., "The diversity of antigen-specific monoclonal antibodies from transgenic mice bearing human immunoglobulin gene miniloci" (1994) *Eur. J. Immunol*., 24:2672-2681.

Ward, "Binding activities of a repertoire of single immunoglobulin variable domains secreted from *Escherichia coli*" (1989) *Nature*, 341:544-546.

Wedemayer et al., "Structural insights into the evolution of an antibody combining site" (1997) *Science*, 276:1665-1669.

Wiendl et al. (BioDrugs. 2002;16(3):183-200).

Williams et al., "Kinetic analysis by stopped-flow radiationless energy transfer studies: effect of anions on the activity of carboxypeptidase A". Biochemistry. 1986, 25, 94-100.

Winter, "Humanized antibodies" (1993) *Immunol. Today*, 14(6):243-246.

Winter, "Making antibodies by phage display technology" (1994) *Annu. Rev. Immunol*., 12:433-455.

Wurm, FM, "Production of recombinant protein therapeutics in cultivated mammalian cells", Nature Biotechnology 22(11):1393-1398, 2004.

Yigzaw et al., "Exploitation of the adsorptive properties of depth filters for host cell protein removal during monoclonal antibody purification," Biotechnology Progress, (2006) 22(1):288-296.

Yumioka et al., "Screening of effective column rinse solvent for Protein-A chromatography," Protein Expression and Purification, (2010) 70(2): 218-223.

Zatarain-Rios E and Mannik M, "Charge-charge interactions between articular cartilage and cationic antibodies, antigens, and immune complexes," Arthritis Rheum. Nov. 1987;30(11):1265-73.

Zhang et al., "Isolation and characterization of charge variants using cation exchange displacement chromatography," 1218(31): 5079-5086, 2011.

Zou et al., "Dominant expression of a 1.3 Mb human Ig kappa locus replacing mouse light chain production" (1996) *FASEB J*., 10:1227-1232.

United States Food and Drug Administration (FDA) Biological Licensing Application File No. 125057 (Adalimumab) (Dec. 31, 2002) (Last Accessed Mar. 4, 2015 at www.fda.gov/Drugs/DevelopmentApprovalProcess/HowDrugsareDevelopedandApproved/ApprovalApplications/TherapeuticBiologicApplications/ucm080610.htm>), 1 page.

Ahmed, M. U.et al.; N-(Carboxyethyl)lysine, a product of the chemical modification of proteins by methylglyoxal, increases with age in human lens proteins; Biochem. J. 1997, 324, 565-570.

Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.

Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.

Ahmed, N.; Thornalley, P. J.; Advanced glycation endproducts: what is their relevance to diabetic complications?; Diabetes, Obes. Metab. 2007, 9, 233-245.

Alfaro, J. F.; Chemo-Enzymatic Detection of Protein Isoaspartate Using Protein Isoaspartate Methyltransferase and Hydrazine Trapping; Anal. Chem. 2008, 80, 3882-3889.

Alfaro, J. F.; Synthesis of LuxS Inhibitors Targeting Bacterial Cell-Cell Communication; Org. Lett. 2004, 6, 3043-3046.

Andersen DC, Goochee CF. The effect of cell-culture conditions on the oligosaccharide structures of secreted glycoproteins. Curr Opin Biotechnol. Oct. 1994;5(5):546-9.

Awdeh, Z.L., A.R. Williamson, and B.A. Askonas, One cell-one immunoglobulin. Origin of limited heterogeneity of myeloma proteins. Biochem J, 1970. 116(2): p. 241-8.

BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf www.bdbiosciences.com/external_files/Doc_Recon_2.0/ab/others/Phytone_Soytone.pdf>), (last accessed Jan. 8, 2015), 4 pages.

Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).

Biastoff, S.; et al.; Colorimetric Activity Measurement of a Recombinant Putrescine N-Methyltransferase from *Datura stramonium*; Planta Med. 2006, 72, 1136.

Burteau et al. (in Vitro Cell Dev Biol—Animal, Jul. / Aug. 2003. 39-291-296).

Chang, T. & Wu, L., Methylglyoxal, oxidative streee, and hypertension, Can. J. Physiol. Pharmacol. 84: 1229-1238 (2006).

Chaplen, F.W.R., et al., Effect of endogenous methylgiyoxal on Chinese hamster ovary celis grown in culture Cytotechnology 1996, vol. 22, Issue 1-3, Abstract and references, 6 pages.

Chaplen, F.W.R., Incidence and potentiai implications of the toxic metabolite methyiglyoxai in cell culture: A review, C\I1otechnology 26: 173-183, 1998.

Chaplen, FWR; A dissertation entitled Analysis of Methylglyoxal Metabolism in Mammalian Cell Culture; Univ. of Wisconsin-Madison 1996, 218 pages.

Chelius, D. et al.; Identification and Characterization of Deamidation Sites in the Conserved Regions of Human Immunoglobulin Gamma Antibodies, Anal. Chem. 2005, 77,6004-6011.

Chumsae, C., et al., Comparison of methionine oxidation in thermal stability and chemically stressed samples of a fully human monoclonal antibody. Journal of Chromatography B, 2007. 850(1-2): p. 285-294.

Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.

Cordoba, A.J., et al., Non-enzymatic hinge region fragmentation of antibodies in solution. Journal of Chromatography B, 2005. 818(2): p. 115-121.

Crowell, C.K., et al., Amino acid and manganese supplementation modulates the glycosylation state of erythropoietin in a CHO culture system. Biotechnology and bioengineering, Feb. 15, 2007; 96(3):538-549.

Dai, S.; An Integrated Proteomic Analysis of Major Isoaspartyl-Containing Proteins in the Urine of Wild Type and Protein Llsoaspartate O-Methyltransferase-Deficient Mice; Anal. Chem. 2013, 85, 2423-2430.

Dobo, A. & Kaltashov, I. A.; Detection of Multiple Protein Conformational Ensembles in Solution via Deconvolution of Charge-State Distributions in ESI MS; Anal. Chem. 2001,73, 4763-4773.

Ellison, Jay W. et al., "The Nucleotide Sequence of a Human Immunoglobulin Cγ1 Gene," Nucleic Acids Research, vol. 10, No. 13 (1982), 9 pages.

Emery, P. "Adalimumab therapy: Clinical findings and implications for integration into clinical guidelines for rheumatoid arthritis." *Drugs of Today*, 41(3): p. 155-153. (2005).

European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.

Fleisher B., Mechanism of glycosylation in the Golgi apparatus. J Histochem Cytochem, Aug. 1983; 31(8):1033-1040.

Gauthier, M. A.& Klok, H.-A. Arginine-Specific Modification of Proteins with Polyethylene Glycol Biomacromolecules; 2011, 12, 482-493.

Gaza-Bulseco, G., et al., Characterization of the glycosylation state of a recombinant monoclonal antibody using weak cation exchange

(56) References Cited

OTHER PUBLICATIONS chromatography and mass spectrometry. J Chromatogr B Analyt Technol Biomed Life Sci, 2008. 862(1-2): p. 155-60. Epub Dec. 8, 2007.
Goochee CF The Oligosaccharides of Glycoproteins: Bioprocess Factors Affecting Oligosaccharide Structure and their Effect on Glycoprotein Properties. Nature Biotechnology Dec. 1991 1346-1355.
Goswami et al., "Developments and Challenges for mAb-Based Therapeutics," *Antibodies*, 2:452-500, 2013.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.
Harding et al., "Class switching in human immunoglobulin transgenic mice" (1995) *Ann. NY Acad. Sci*., 764:536-547.
Harlow et al., Eds ("Antibodies: A Laboratory Manual" 1988. Cold Spring Harbor Laboratory Press, Chapter 7, pp. 245, 247,and 253).
Harris, R.J., et al., Identification of multiple sources of charge heterogeneity in a recombinant antibody. Journal of Chromatography B: Biomedical Sciences and Applications, 2001. 752(2): p. 233-245.
Harris, Reed J. et al., "Structural Characterization of a Recombinant CD4-IgG Hybrid Molecule," Eur. J. Biochem. 194:611-620 (1990).
Hills, A.E. et al., Metabolic control of recombinant monoclonal antibody N-glycosylation in GS-NS0 cells, Biotechnology and Bioengineering, Oct. 20, 2001; 75(2):239-251.
Hipkiss, A.; Can the beneficial effects of methionine restriction in rats be explained in part by decreased methylglyoxal generation resulting from suppressed carbohydrate metabolism?; Biogerontology 2012, 13, 633-636.
Hossler et al., "Optimal and consistent protein glycosylation in mammalian cell culture", Glycobiology; (2009), 19(9):936-949.
Huang, L., et al., In Vivo Deamidation Characterization of Monoclonal Antibody by LC/MS/MS. Analytical Chemistry, 2005. 77(5): p. 1432-1439.
HyClone™ CDM4CHO Catalog listing (last accessed Nov. 17, 2014).
International Preliminary Report on Patentability for Application No. PCT/US2013/031352 dated Nov. 25, 2014, pp. 1-10.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for PCT/US2012/035266, dated Feb. 7, 2013 (corresponds to U.S. Appl. No. 13/547,020), 4 pages.
International Search Report for Application No. PCT/US2014/026606, Dated Dec. 8, 2014, 8 pages.
International Search Report for Application No. PCT/US2014/026636, Dated Jul. 29, 2014, 5 pages.
Jack, M.; Wright, D.; The Role of Advanced Glycation Endproducts and Glyoxalase I in Diabetic Peripheral Sensory Neuropathy; Transl. Res. 2012, 159, 355-365.
Jakubowski, H., Protein N-homocysteinylation: implications for atherosclerosis. Biomedicine & amp; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jefferis, R., Glycosylation of Recombinant Antibody Therapeutics. Biotechnology Progress, 2005.21(1): p. 11-16.
Johnson, K.A., et al., Cation exchange HPLC and mass spectrometry reveal C-terminal amidation of an IgG1 heavy chain. Analytical Biochemistry, 2007. 360(1): p. 75-83.
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Kingkeohoi, S. & Chaplen, F.W.R., Analysis of methylglyoxal metabolism in CHO celis grown in culture, Cytotechnology (2005) 48:1-13.
Kwon et al., "Production of lactic acid by *Lactobacillus rhamnosus* with vitamin-suppremented soybean hydrolysate", Enzyme Microb Technol. (2000), 26:209-215.
Leusch, "Failure to demonstrate TNFα-specific autoantibodies in human sera by ELISA and Western blot" (1991) *J. Immunol. Methods*, 139:145-47.
Li, Feng, et al., "Cell Culture Processes for Monoclonal Antibody Production," mAbs 2:5, 466-479 (Sep.-Oct. 2010).
Liu, H., et al., Heterogeneity of monoclonal antibodies. Journal of Pharmaceutical Sciences, 2008. 97(7): p. 2426-2447.
Liu, H., Gaza-Bulseco, G., & Lundell, E., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, M, et al.; Discovery of Undefined Protein Cross-Linking Chemistry: A Comprehensive Methodology Utilizing 18O- Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methyiglyoxai under physioiogical conditions. A kinetic and mechanistic study with N alpha-acetylarginine, N alpha-acetylcysteine, and N alpha-acetyilysine, and bovine serum albumin, Dec. 23, 1994, The Journal of Biological Chemistry, 269, 32299-32305.
Manning, M., et al., *Stability of Protein Pharmaceuticals: An Update*. Pharmaceutical Research, 2010.27(4): p. 544-575.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
Mizuochi, T., et al., Structural and numerical variations of the carbohydrate moiety of immunoglobulin G. J Immunol, 1982. 129(5): p. 2016-20.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Ni, W.; Analysis of Isoaspartic Acid by Selective Proteolysis with Asp-N and Electron Transfer Dissociation Mass Spectrometry; Anal. Chem. 2010, 82,7485-7491.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation-what affect high mannose 5 glycoform", Biotechnology and Bioengineering vol. 108, No. 10 Oct. 2011, pp. 2348-2358.
Paoli, T. et al., a Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trends in Biotechnology.
Parekh, R.B., et al., Association of rheumatoid arthritis and primary osteoarthritis with changes in the glycosylation pattern of total serum IgG. Nature, 1985. 316(6027): p. 452-7.

(56) References Cited

OTHER PUBLICATIONS

PCT/US2013/069702 International Search Report & Written Opinion mailed Jan. 31, 2014, 13 pages.

Perkins, M.; et. Al. Determination of the Origin of Charge Heterogeneity in a Murine Monoclonal Antibody; M. Pharm. Res. 2000, 17, 1110-1117.

Quan, C., et al., A study in glycation of a therapeutic recombinant humanized monoclonal antibody: Where it is, how it got there, and how it affects charge-based behavior. Analytical Biochemistry, 2008. 373(2): p. 179-191.

Rabbani, N.; Thornalley, P. J.; Glyoxalase in diabetes, obesity and related disorders; Semin. Cell Dev. Biol. 2011, 22, 309-317.

Ren, D., et al., Reversed-phase liquid chromatography-mass spectrometry of site-specific chemical modifications in intact immunoglobulin molecules and their fragments. Journal of Chromatography A, 2008. 1179(2): p. 198-204.

Roy, B.M., et al., Toxic concentrations of exogenously supplied methylglyoxal in hybridoma cell culture, Cytotechnology (2004) 46:97-107.

Saxena, R. K. et al.; Microbial production and applications of 1,2-propanediol; Indian J. Microbiol. 2010,50,2-11.

Shen, Amy Y. et al., "Recombinant DNA Technology and Cell Line Development," from "Cell Culture Techology for Pharmaceutical and Cell-Based Therapies," CRC Press, 1995, 15-40.

Sigma Catalog "RPMI1640" (last accessed Jan. 22, 2015), 3 pages.

Sigma MSDS for RMPI1640 (last accessed Jan. 22, 2015), 6 pages.

TESS database "HYCLONE" Trademark #76244963. Filing date Apr. 23, 2001. Live mark. Last accessed Jan. 21, 2015.

TESS database "HYCLONE" Trademark #85769283. Filing date Sep. 30, 2012. Live mark. Last accessed Jan. 21, 2015.

The Kennedy Institute of Rheumatology, 1995 Annual Scientific Report, "Anti-TNF trials and studies of mechanisms of action".

Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.

Vasilli, P., Annu. Rev. Immunol. 10:411-452 (1992); and Tracey, K. J. and Cerami, A. Annu. Rev. Med. 45:491-503 (1994).

Vlasak, J. & Ionescu, R., *Heterogeneity of Monoclonal Antibodies Revealed by Charge-Sensitive Methods*. Current Pharmaceutical Biotechnology, 2008. 9(6): p. 468-481.

Walsh, et al.: "Post-translational modifications in the context of therapeutic proteins", Nature Biotechnology, vol. 24, No. 10, Oct. 2006, pp. 1241-1252.

Wang, Z.; et al. Desulfurization of Cysteine-Containing Peptides Resulting from Sample Preparation for Protein Characterization by MS; Rapid Commun. Mass Spectrom. 2010, 24, 267-275.

Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.

Williams, A. et al., Ion-Exchange Chromatography, Oct. 1998, Supplement 44, pp. 10-10-1-10-10-30.

Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.

Yuk, I.H. et al., Controlling Glycation of Recombinant Antibody in Fed Batch Cell Cultures, Nov. 2011, Biotechnology and Bioengineering, vol. 108, No. 11 pp. 2600-2610.

Zang, T.; et al.; Chemical Methods for the Detection of Protein N-Homocysteinylation via Selective Reactions with Aldehydes; Anal. Chem. 2009, 81, 9065-9071.

Zhang, B., et al., Unveiling a Glycation Hot Spot in a Recombinant Humanized Monoclonal Antibody. Analytical Chemistry, 2008. 80(7): p. 2379-2390.

Zhang, T.; Identification and Characterization of Buried Unpaired Cysteines in a Recombinant Monoclonal IgG1 Antibody; Anal. Chem. 2012, 84, 7112-7123.

Zhang, W. and Czupryn, M.J., Free Sulfhydryl in Recombinant Monoclonal Antibodies. Biotechnology Progress, 2002. 18(3): p. 509-513.

Zhao, G.; Chemical Synthesis of S-Ribosyl-L-homocysteine and Activity Assay as a LuxS Substrate; Bioorg. Med. Chem. Lett. 2003,13,3897-3900.

Zhou, Z. et al.; An Antibody-Catalyzed Allylic Sulfoxide-Sulfenate Rearrangement; J. Org. Chem. 1999,64,8334-8341.

Zhou, Z. S. et al. An Antibody-Catalyzed Selenoxide Elimination; J. Am. Chem. Soc. 1997, 119, 3623-3624.

Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.

Anonymous, "SACHEM Displacement Chromatography," Aug. 29, 2012, Retrieved from the internet: <www.displacementchromatography.com>, retrieved on Jul. 30, 2014.

Averginos, Gab '04 Abstracts—GE Healthcare Life Sciences, "HUMIRA manufacturing: challenges and the path taken", France, Oct. 3-5, 2004, published 2005, pp. 14-16.

Barnes et al., "Stability of Protein Production from Recombinant Mammalian Cells," Biotechnology and Bioengineering, 81:6, Mar. 20, 2003, pp. 631-639.

Byun, et al. Archives of Biochemistry and Biophysics, "Transport of anti-IL-6 binding fragments into cartilage and the effects of injury," 532 (2013), pp. 15-22.

Du et al., "Chromatographic analysis of the acidic and basic species of recombinant monoclonal antibodies" MAbs, Sep.-Oct. 2012; 4(5):578-85.

Feng et al., "Cell Culture Processes for Monoclonal Antibody Production," mAbs, 2:5, 466-477, Sep./Oct. 2010.

Folk et al., "Carboxypeptidase B, Purification and Characterization of the Porcine Enzyme," J. Biological Chem, 1960, 235:2272-2277.

Gramer M J et al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.

Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.

Hossler et al.; "Improvement of mammalian cell culture performance through surfactant enabled concentrated feed media"; Biotechnology Progress; 29(4):1023-1033 (2013).

Humira (adalimumab) prescribing information, Dec. 20, 2002, pp. 1-16.

ICH Topic Q6B "Specifications:Test Procedures and Acceptance Criteria for Biotechnological/Biological Products," Sep. 1999, pp. 1-17.

International Search Report and Written Opinion from PCT/US2013/065749 dated Mar. 18, 2014, pp. 1-18.

International Search Report and Written Opinion from PCT/US2014/024151 dated Aug. 7, 2014, pp. 1-16.

International Search Report from PCT/US2014/024256 dated Jul. 30, 2014, pp. 1-15.

Invitation to Pay Additional Fees for International Application No. PCT/US2013/065749, Dated May 27, 2014, pp. 1-8.

Invitation to Pay Additional Fees for International Application No. PCT/US2014/026606, Dated Jul. 8, 2014, pp. 1-8.

Jayme et al.; "Media formulation options and manufacturing process controls to safeguard against introduction of animal origin contaminants in animal cell culture"; Cytotechnology; 33:27-36 (2000).

Sakai et al.; "Use of nonionic surfactants for effective supply of phosphatidic acid in serum-free culture of Chinese hamster ovary cells"; Journal of Bioscience and Bioengineering; 92(3):256-261 (2001).

Sundaram et al., "An innovative approach for the characterization of the isoforms of a monoclonal antibody product," Mabs, 3(6):505-512, 2011.

(56) References Cited

OTHER PUBLICATIONS

Tharmalingam et al.; "Pluronic Enhances the Robustness and Reduces the Cell Attachment of Mammalian Cells"; Molecular Biotechnology; 39(2):167-177 (2008).

Wolff et al., "The Kinetics of Carboxypeptidase B Activity," J. Biological Chem, 1962, 237:3094-3099.

Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.

Worthington Biochemical Corporation, porcine pancreas carboxypeptidase B, one page, Feb. 25, 2012.

* cited by examiner

Example 1: Effect of yeast, soy, or wheat hydrolysate addition to CDM GIA-1 in adalimumab-producing CHO cell line #1 on (A) Culture growth, (B) Culture viability, and (C) Harvest titer Example 1: Effect of yeast, soy, or wheat hydrolysate addition to CDM GIA-1 in adalimumab-producing CHO cell line #1 on (A) Culture growth, (B) Culture viability, and (C) Harvest titer Example 1: Effect of yeast, soy, or wheat hydrolysate addition to CDM GIA-1 in adalimumab-producing CHO cell line #1 on (A) Culture growth, (B) Culture viability, and (C) Harvest titer Example 1: Effect of yeast, soy, or wheat hydrolysate addition to CDM GIA-1 in adalimumab-producing CHO cell line #1 on (A) NGA2F+NGA2F-GlcNac and (B) NA1F+NA2F.

Example 2: Effect of combined supplementation of yeast and soy hydrolysates to CD media from multiple suppliers in adalimumab-producing CHO cellline #1 on
(A) Culture growth, (B) Viability, and (C) Harvest titer Example 2: Effect of combined supplementation of yeast and soy hydrolysates to CD media from multiple suppliers in adalimumab-producing CHO cell line #1 on (A) NGA2F+NGA2F-GlcNac and (B) NA1F+NA2F Example 3: Effect of supplementing (A) yeast, (B) soy, or (C) wheat hydrolysate from multiple vendors to CDM GIA-1 on culture growth in CHO cell line #1

Example 3: Effect of supplementing (A) yeast, (B) soy, or (C) wheat hydrolysate from multiple vendors to CDM GIA-1 on culture viability in CHO cell line #1

Example 3: Effect of supplementing yeast, soy, or wheat hydrolysate from multiple vendors to CDM GIA-1 on harvest titer in CHO cell line #1

Example 3: Effect of supplementing yeast, soy, or wheat hydrolysate from multiple vendors to CDM GIA-1 in CHO cell line #1 on (A) NGA2F+NGA2F-GlcNac and (B) NA1F+NA2F Example 4: Viable Cell Density and Viability in Hydrolysate Study #1 (Note: Error bar represent one standard deviation).

Example 4: Viable Cell Density and Viability in Hydrolysate Study #2 (Note: Error bar represents one standard deviation).

| Condition (no. of runs) | %NGA2F+ (NGA2F-GlcNAc) | % NA1F+NA2F | %Man5+Man6 |
|---|---|---|---|
| Control: Y/P =1.55 (n=5) | 75.87 ± 1.04 | 17.54 ± 0.91 | 6.59 ± 0.39 |
| Y/P = 0.67 (n=5) | 74.31 ± 0.73 | 18.32 ± 0.41 | 7.35 ± 0.63 |
| Y/P = 0.25 (n=5) | 72.75 ± 0.91 | 19.07 ± 0.54 | 8.29 ± 0.94 |

Figure 11. Example 4: Glycosylation Profile in Hydrolysate Study 1 (Note: "±" represents one standard deviation)

| Condition (no. of runs) | %NGA2F+ (NGA2F-GlcNAc) | % NA1F+NA2F | %Man5+Man6 |
|---|---|---|---|
| Control: Y/P =1.55 (n=6) | 77.49 ± 0.34 | 15.55 ± 0.62 | 6.95 ± 0.30 |
| Y/P = 0.67 (n=6) | 75.40 ± 0.14 | 17.97 ± 0.18 | 6.64 ± 0.13 |

Figure 12. Example 4: Glycosylation Profile in Hydrolysate Study 2 (Note: "+" represents one standard deviation)

Example 5: Effect of asparagine and gluta mine in 3L bioreactor batch culture in hydrolysate based medium with adalimumab-producing CHO cell line #1on (A) Culture growth, (B) Culture viability, and (C) Harvest titer when asparagine and/or glutamine was added on day7.

Example 5: Effect of asparagine and glutamine in 3L bioreactor batch culture in hydrolysate based medium with adalimumab-producing CHO cell line #1 on (A) NGA2F+NGA2F-GlcNac and (B) NA1F+NA2F when asparagine and/or glutamine was added on day7

Example 5: Effect of asparagine in 3L bioreactor batch culture in hydrolysate based medium with adalimumab-producing CHO cell line #1 on A) Culture growth, (B) Culture viability, and (C) Harvest titer when asparagine was added on day7

Example 5: Effect of asparagine in 3L bioreactor batch culture in hydrolysate based medium with adalimumab-producing CHO cell line #1 on (A) NGA2F+NGA2F-GlcNac and (B) NA1F+NA2F when asparagine was added on day7

Example 5: Effect of asparagine in 3L bioreactor batch culture in hydrolysate based medium with adalimumab-producing CHO cell line #1 on A) Culture growth, (B) Culture viability, and (C) Harvest titer when asparagine was added on day0

Example 5: Effect of asparagine in 3L Bioreactor catch culture in hydrolysate based medium with adalimumab-producing CHO cell line #1 on (A) NGA2F+NGA2F-GlcNac and (B) NA1F+NA2F when asparagine was added on day0

Example 6: Effect of yeast, soy, or wheat hydrolysate addition to CDM Irvine IS CHO-CD in adalimumab-producing CHO cell line #1 on (A) Culture growth, (B) Culture viability, and (C) Harvest titer Example 6: Effect of yeast, soy, or wheat hydrolysates addition to CDM Irvine IS CHO-CD in adalimumab-producing CHO cell line #1 on oligosaccharides profile (A) NGA2F+NGA2F-GlcNac and (B) NA1F+NA2F Example 7: Effect of yeast, soy, or wheat hydrolysate addition to CDM GIA-1 in adalimumab-producing CHO cell line #2 on (A) Culture growth, (B) Culture viability, and (C) Harvest titer Example 7: Effect of yeast, soy, or wheat hydrolysate addition to CDM GIA-1 in adalimumab-producing CHO cell line #2 on (A) NGA2F+NGA2F- GlcNac and (B) NA1F+NA2F Example 8: Effect of yeast, soy, or wheat hydrolysate addition to CDM GIA-1 in adalimumab-producing CHO cell line #3 on (A) Culture growth, (B) Culture viability, and (C) Harvest titer

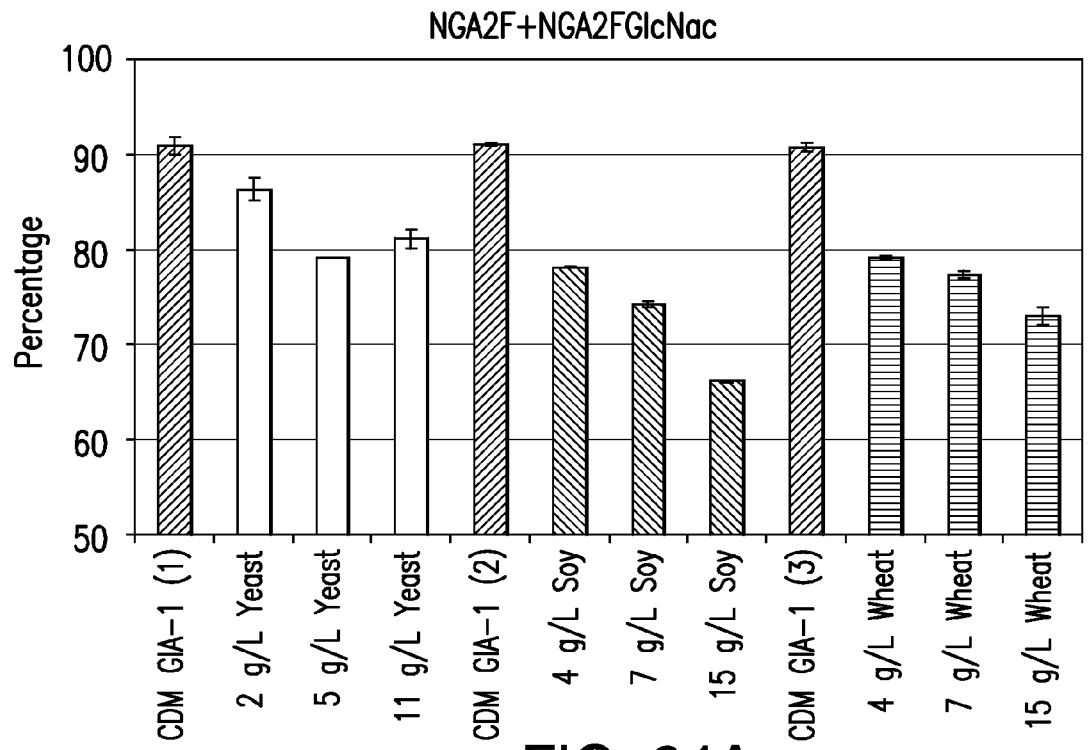
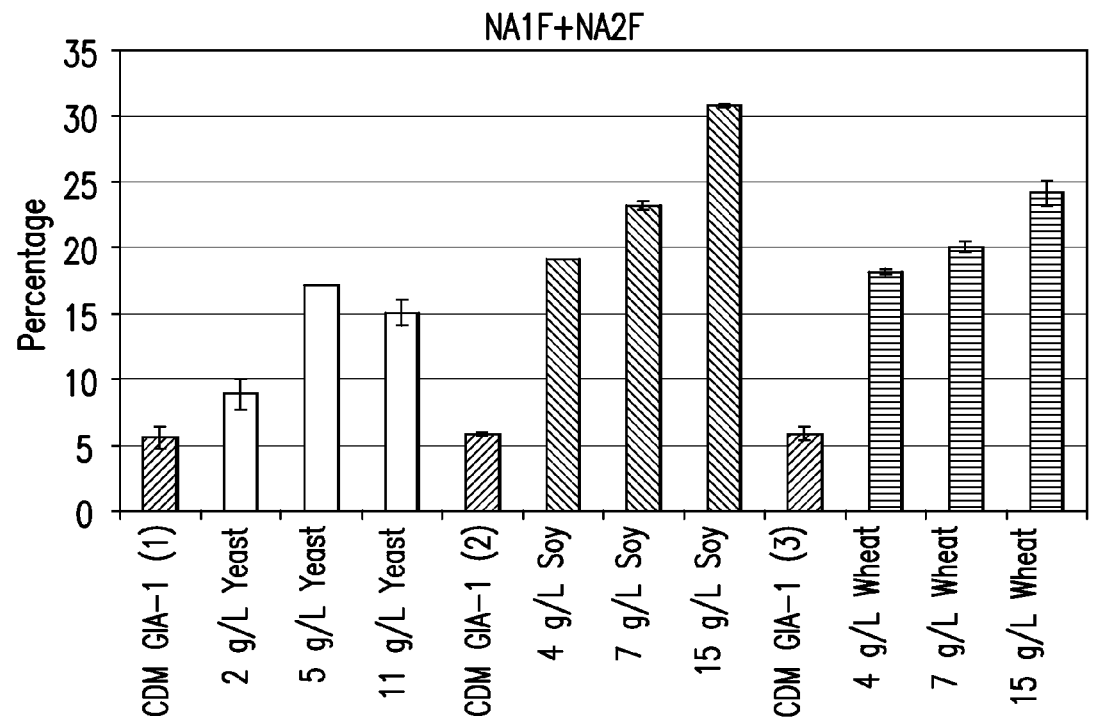
Example 8: Effect of yeast, soy, or wheat hydrolysate addition to CDM GIA−1 in adalimumab−producing CHO cell line #3 on (A) NGA2F+NGA2F−GlcNac and (B) NA1F+NA2F
FIG. 24B Example 9: Effect of yeast, soy, or wheat hydrolysate addition to CDM GIA-1 in CHO cell line producing mAb #1 (A) Culture growth, (B) Culture viability, and (C) Harvest titer Example 9: Effect of yeast, soy, or wheat hydrolysate addition to CDM GIA-1 in CHO cell line producing mAb #1 on (A) NGA2F+NGA2F-GlcNac and (B) NA1F+NA2F Example 10: Effect of yeast, soy, or wheat hydrolysate addition to CDM GIA-1 in CHO cell line producing mAb #2 on (A) Culture growth, (B) Culture viability, and (C) Harvest titer Example 10: Effect of yeast, soy, or wheat hydrolysate addition to CDM GIA-1 in CHO cell line producing mAb #2 on (A) NGA2F + NGA2F-GlcNac and (B) NA1F + NA2F Example 11: Effect of combined supplementation of yeast, soy and/or wheat hydrolysates to CDM GIA 1 in adalimumab-producing CHO cell line #1 on
(A) Culture growth, (B) Viability, and (C) Harvest titer Example 11: Effect of combined supplementation of yeast, soy, and/or wheat hydrolysates to CDM GIA-1 in adalimumab-producing CHO cell line #1 on (A) NGA2F+NGA2F-GlcNac and (B) NA1F+NA2F Example 12: Effect of asparagine in shake flask batch culture in CDM GIA −1 medium with adalimumab-producing CHO cell line #1 on A) Culture growth, (B) Culture viability, and (C) Harvest titer when asparagine was added on day6

Example 12: Effect of asparagine in shake flask batch culture in CDM GIA-1 medium with adalimumab-producing CHO cell line #1 on (A) NGA2F+NGA2F-GlcNac and (B) NA1F+NA2F when asparagine was added on day6

Example 13: Effect of asparagine in shake flask batch culture in CDM GIA-1 medium with adalimumab-producing CHO cell line #3 on A) Culture growth, (B) Culture viability, and (C) Harvest titer when asparagine was added on day6

Example 13: Effect of asparagine in shake flask batch culture in CDM GIA-1 medium with adalimumab _producing CHO cell line #3 on (A) NGA2F+NGA2F-Glc Nac and (B) NA1F+NA2F when asparagine was added on day6

Example 14: Effect of asparagine in shake flask batch culture in CDM GIA
-1 medium with CHO cell line producing mAb #2
on A) Culture growth, (B) Culture viability, and (C)
Harvest titer when Asparagine was supplemented during
medium preparation.

Example 14: Effect of asparagine in shake flask batch culture in CDM GIA
−1 medium with CHO cell line producing mAb #2 on (A) NGA2F+NGA2F
−GlcNac and (B) NA1F+NA2F and Mannose Type when asparagine was
supplemented during medium preparation.

Example 14: Effect of asparagine in shake flask batch culture in CDM GIA-1 medium with CHO cell line producing mAb #2 on A) Culture growth, (B) Culture viability, and (C) Harvest titer when Asparagine was added on day 5.

Example 14: Effect of asparagine in shake flask batch culture in CDM GIA-1 medium with CHO cell line producing mAb #2 on (A) NGA2F+NGA2F-GlcNac and (B) NA1F+NA2F and Mannose Type when asparagine was added on day 5.

Figure 39.    Experimental design for Example 1

| Experiment Block # | Hydrolysate Name | Hydrolysate Vendor / Catalog Number | Concentration in adaptation media (g/kg) | Concentration in production media (g/kg) |
|---|---|---|---|---|
| I | Bacto TC Yeastolate | BD Biosciences / 255772 | 2 | 2, 5, 11 |
|  | BBL Phytone Peptone | BD Biosciences / 211096 | 2 | 2, 4, 7, 10, 15 |
|  | Wheat Peptone E1 | Organotechnie / 19559 | 2 | 2, 4, 7, 10, 15 |
| II | BBL Phytone Peptone | BD Biosciences / 211096 | 2 | 10, 15 |
|  | Wheat Peptone E1 | Organotechnie / 19559 | 2 | 10, 15 |

Figure 40.    Experimental design for Example 2

| Media/Vendor/Catalog Number | Hydrolysates/Vendor/Catalog Number | Concentration in adaptation media (g/kg) | Concentration in production media (g/kg) |
|---|---|---|---|
| OptiCHO / Life Sciences Gibco/12681-011 GIA-1 / Life Sciences Gibco / Custom formulation CDM4CHO / HyClone / SH30558.02 IS CHO-CD / Irvine Scientific / 91119 | Bacto TC Yeastolate / BD Biosciences / 255772 BBL Phytone Peptone / BD Biosciences / 211096 | 4.0 (TC Yeastolate) 2.6 (Phytone Peptone) | 10.7 (TC Yeastolate) 6.9 (Phytone Peptone) |

Figure 41. Experimental design for Example 3

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 5, 11 |
| HyPep Yeast Extract | Sheffield/Kerry Biosciences | 2 | 5, 11 |
| UF Yeast Hydrolysate | Irvine Scientific / 292804 | 2 | 5, 11 |
| BBL Phytone Peptone | BD Biosciences / 211096 | 2 | 4, 7 |
| HyPep 1510 | Sheffield/Kerry Biosciences / 5x59053 | 2 | 4, 7 |
| SE50 MAF-UF | DMV International / SE50 MAF-UF | 2 | 4, 7 |
| UF Soy Hydrolysate | Irvine Scientific / 96857 | 2 | 4, 7 |
| Wheat Peptone E1 | Organotechnie / 19559 | 2 | 4, 7 |
| HyPep 4601 | Sheffield/Kerry Biosciences / 5z10419 | 2 | 4, 7 |
| Proyield WGE80M Wheat | DMV International / WGE80M | 2 | 4, 7 |

Figure 42. Experimental design for Example 6

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5 |
| BBL Phytone Peptone | BD Biosciences / 211096 | 2 | 4, 7 |
| Wheat Peptone E1 | Organotechnie / 19559 | 2 | 4, 7 |

Figure 43. Experimental design for Example 7

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 4, 7, 15 |
| Wheat Peptone E1 | Organotechnie / 19559 | 2 | 4, 7, 10 |

Figure 44. Experimental design for Example 8

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 4, 7, 15 |
| Wheat Peptone E1 | Organotechnie / 19559 | 2 | 4, 7, 15 |

Figure 45. Experimental design for Example 9

| Hydrolysate Name | Hydrolysate Vendor and Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 2, 4, 7 |
| Wheat Peptone E1 | Organotechnie / 19559 | 2 | 2, 4, 7 |

Figure 46. Experimental design for Example 10

| Hydrolysate Name | Hydrolysate Vendor / Catalog Number | Concentration in adaptation media (g/kg) | Concentration in production media (g/kg) |
|---|---|---|---|
| Bacto TC Yeastolate | BD Biosciences / 255772 | 2 | 2, 5, 11 |
| BBL Phytone Peptone | BD Biosciences / 211096 | 2 | 2, 4, 7 |
| Wheat Peptone E1 | Organotechnie / 19559 | 2 | 2, 4, 7 |

Figure 47. Experimental design for Example 11 (adaptation stage)

| Experimental ID | Bacto TC Yeastolate (BD Biosciences / 255772) (g/L) | BBL Phytone Peptone (BD Biosciences / 211096) (g/L) | Wheat Peptone E1 (Organotechnie / 19559) (g/L) |
|---|---|---|---|
| 1 (control) | 0 | 0 | 0 |
| 2 | 2 | 0 | 0 |
| 3 | 0 | 2 | 0 |
| 4 | 0 | 0 | 2 |
| 5 | 2 | 2 | 0 |
| 6 | 2 | 0 | 2 |
| 7 | 0 | 2 | 2 |
| 8 | 2 | 2 | 2 |

Figure 48. Experimental design for Example 11 (production stage)

| Experimental ID | Bacto TC Yeastolate (BD Biosciences / 255772) (g/L) | BBL Phytone Peptone (BD Biosciences / 211096) (g/L) | Wheat Peptone E1 (Organotechnie / 19559) (g/L) |
|---|---|---|---|
| 1 (control) | 0 | 0 | 0 |
| 2 | 5 | 0 | 0 |
| 3 | 0 | 4 | 0 |
| 4 | 0 | 0 | 4 |
| 5 | 5 | 4 | 0 |
| 6 | 5 | 0 | 4 |
| 7 | 0 | 4 | 4 |
| 8 | 5 | 4 | 4 |

METHODS TO CONTROL PROTEIN HETEROGENEITY

CROSS REFERENCE TO RELATED APPLICATIONS

The present application claims priority to U.S. Provisional Application No. 61/696,219, filed on Sep. 2, 2012, the disclosure of which is incorporated by reference herein in its entirety.

1. INTRODUCTION

The instant invention relates to the field of protein production, and in particular to compositions and processes for controlling and limiting the heterogeneity of proteins expressed in host cells.

2. BACKGROUND OF THE INVENTION

The production of proteins for biopharmaceutical applications typically involves the use of cell cultures that are known to produce proteins exhibiting varying levels of heterogeneity. The basis for such heterogeneity includes, but is not limited to, the presence of distinct glycosylation substitution patterns. For example, such heterogeneity can be observed in increases in the fraction of proteins substituted with agalactosyl fucosylated biantennary oligosaccharides NGA2F+NGA2F-GlcNAc and decreases in the fraction of proteins substituted with galactose-containing fucosylated biantennary oligosaccharides NA1F+NA2F. Such heterogeneity can be assayed by releasing oligosaccharides present on the protein of interest via enzymatic digestion with N-glycanase. Once the glycans are released, the free reducing end of each glycan can be labeled by reductive amination with a fluorescent tag. The resulting labeled glycans are separated by normal-phase HPLC(NP-HPLC) and detected by a fluorescence detector for quantitation.

Technological advances in recombinant protein production analysis have provided unique opportunities for identifying the extent of heterogeneity exhibited by a particular protein population, particularly in the context of large-scale production of recombinant proteins. Although such advances have allowed for the robust characterization of protein heterogeneity, there remains a need in the art to identify culture conditions and production methods that allow for control over the development of such heterogeneity. Control of protein heterogeneity is particularly advantageous in the context of cell culture processes used for commercially produced recombinant bio-therapeutics as such heterogeneity has the potential to impact therapeutic utility. The instant invention addresses this need by providing compositions and processes to control protein heterogeneity.

3. SUMMARY OF THE INVENTION

The present invention is directed to compositions and methods that control (modulate or limit) protein heterogeneity arising in a population of proteins, e.g., in the context of recombinant protein production.

In certain embodiments, the heterogeneity corresponds to the glycosylation state of individual members of a population of proteins. In certain embodiments, control is exerted over the type of glycosylation substitutions present on individual members of a population of proteins in certain embodiments, control is exerted over the extent of glycosylation substitutions present on individual members of a population of proteins. In certain embodiments, control is exerted over both the type and extent of glycosylation substitutions present on individual members of a population of proteins. In certain embodiments, such control results in a decrease in the amount of NGA2F+NGA2F-GlcNac oligosaccharides and/or an increase in the amount of NA1F+NA2F oligosaccharides linked to the protein of interest. In certain embodiments, such control results in an increase in the amount of NGA2F+NGA2F-GlcNac oligosaccharides and/or a decrease in the amount of NA1F+NA2F oligosaccharides linked to the protein of interest.

In certain embodiments, control over protein glycosylation heterogeneity is exerted by employing specific hydrolysates during production of the protein of interest, for example, but not by way of limitation, in adaptation cultures performed in media supplemented with hydrolysates. In certain embodiments, control over protein glycosylation heterogeneity is exerted by maintaining certain yeastolate to phytone ratios during production of the protein of interest. In certain embodiments, control over protein glycosylation heterogeneity is exerted by the addition of asparagine during the production of the protein of interest. In certain embodiments the amount of asparagine present in the cell culture media will range from about 0 mM to about 26 mM.

In certain embodiments, control over the heterogeneity of the protein compositions described herein is exerted by employing one or more of the foregoing methods during the production and purification of the desired proteins, such as antibodies or antigen-binding portions thereof, described herein.

The heterogeneity of the proteins of interest in the resultant sample product can be analyzed using methods well known to those skilled in the art, e.g., weak cation exchange chromatography (WCX), capillary isoelectric focusing (cIEF), size-exclusion chromatography, Poros™ A HPLC Assay, Host Cell Protein ELISA, Protein A ELISA, and western blot analysis.

In yet another embodiment, the invention is directed to one or more pharmaceutical compositions comprising an isolated protein, such as an antibody or antigen-binding portion thereof, and an acceptable carrier. In another aspect, the compositions further comprise one or more pharmaceutically acceptable carriers, diluents, and/or pharmaceutical agents.

4. BRIEF DESCRIPTION OF THE DRAWINGS

FIG. 11 depicts the glycosylation profile in Example 4: Hydrolysate Study #1 in adalimumab-producing CHO cell line 41.

FIG. 12 depicts the glycosylation profile in Example 4: Hydrolysate Study #2 in adalimumab-producing CHO cell line #1.

FIG. 24 depicts the effect of yeast, soy, or wheat hydrolysate addition to CDM GIA-1 in adalimumab-producing CHO cell line #3 on (a) NGA2F+NGA2F-GlcNac and (b) NA1F+NA2F.

Figure 1A:
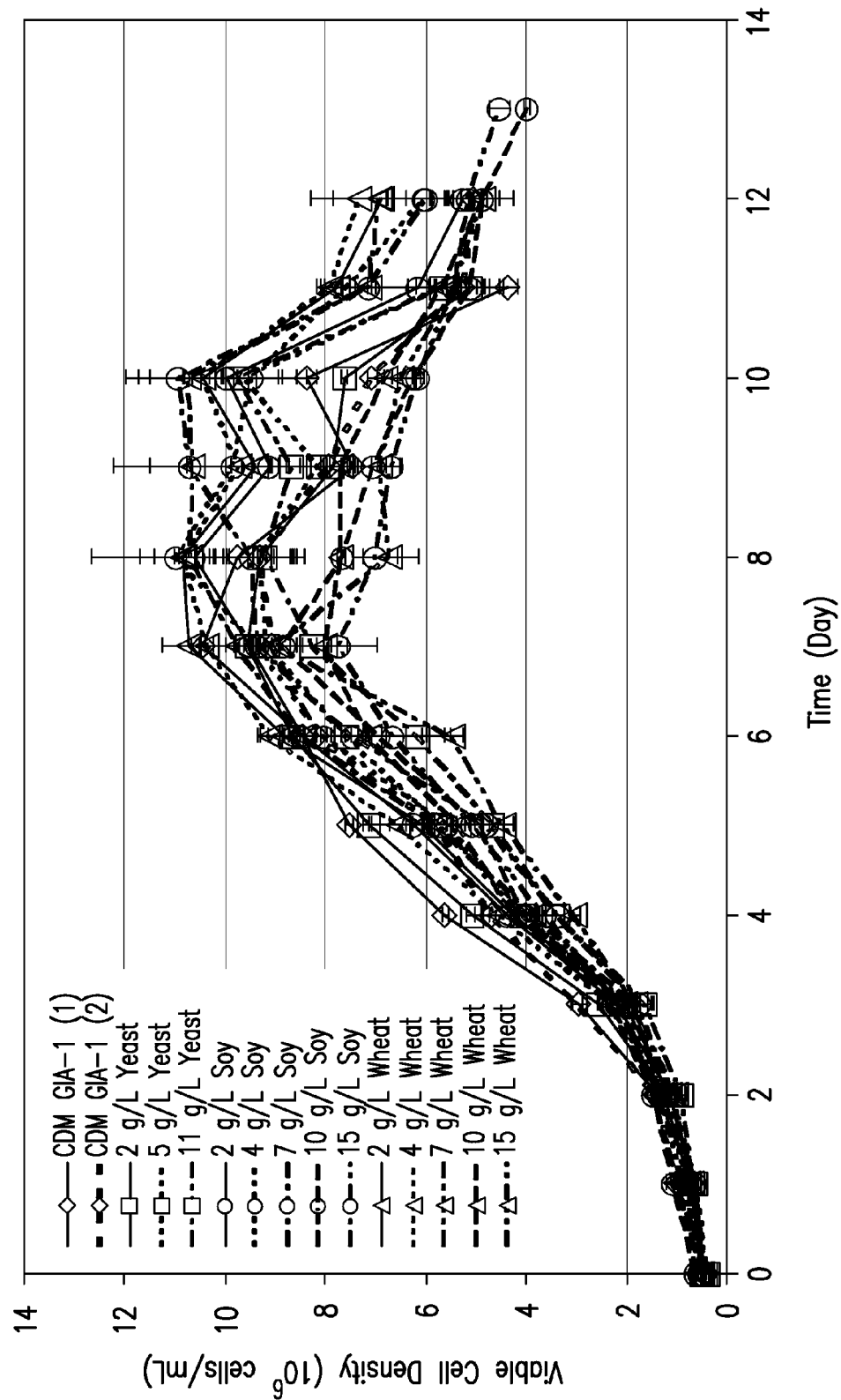
FIG. 1 depicts the effect of yeast, soy, or wheat hydrolysate addition to CDM GIA-1 in adalimumab-producing CHO cell line #1 on (a) Culture growth, (b) Culture viability, and (c) Harvest titer.

FIG. 39 depicts the experimental design for Example 1.
FIG. 40 depicts the experimental design for Example 2.
FIG. 41 depicts the experimental design for Example 3.
FIG. 42 depicts the experimental design for Example 6.
FIG. 43 depicts the experimental design for Example 7.

FIG. 44 depicts the experimental design for Example 8.
FIG. 45 depicts the experimental design for Example 9.
FIG. 46 depicts the experimental design for Example 10.
FIG. 47 depicts the experimental design for Example 11 (adaptation stage).
FIG. 48 depicts the experimental design for Example 11 (production stage).

5. DETAILED DESCRIPTION

For clarity and not by way of limitation, this detailed description is divided into the following sub-portions:
5.1 Definitions; and
5.2 Control of Heterogeneity:
5.2.1 Supplementation of CD Media with Yeast and/or Plant Hydrolysates
5.2.2 Changing Yeast to Plant Hydrolysate Ratio in Cell Culture Medium
5.2.3 Supplementation with Asparagine
5.1 Definitions In order that the present invention may be more readily understood, certain terms are first defined.

As used herein, the term "glycosylation" refers to the addition of a carbohydrate to an amino acid. Such addition commonly, although not exclusively, occurs via a nitrogen of asparagine or arginine ("N-linked" glycosylation) or to the hydroxy oxygen of serine, threonine, tyrosine, hydroxylysine, or hydroxyproline side-chains ("O-linked" glycosylation). In eukaryotes, N-linked glycosylation occurs on the asparagine of the consensus sequence Asn-Xaa-Ser/Thr, in which Xaa is any amino acid except proline (Kornfeld et al., Ann Rev Biochem 54: 631-664 (1985); Kukuruzinska et al, Proc. Natl. Acad, Sci. USA 84: 2145-2149 (1987); Herscovics et al, FASEB J. 7:540-550 (1993); and Orlean, Saccharomyces Vol, 3 (1996)). O-linked glycosylation also takes place at serine or threonine residues (Tanner et al., Biochim. Biophys. Acta. 906: 81-91 (1987); and Hounsell et al, Glycoconj. J. 13: 19-26 (1996)). However, other glycosylation patterns can be formed, e.g., by linking glycosylphosphatidyl-inositol to the carboxyl-terminal carboxyl group of a protein.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., in the case of Adalimumab, hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR), Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al, (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

As used herein, the term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. In certain embodiments the host cell is employed in the context of a cell culture.

As used herein, the term "cell culture" refers to methods and techniques employed to generate and maintain a population of host cells capable of producing a recombinant protein of interest, as well as the methods and techniques for optimizing the production and collection of the protein of interest. For example, once an expression vector has been incorporated into an appropriate host, the host can be maintained under conditions suitable for high level expression of the relevant nucleotide coding sequences, and the collection and purification of the desired recombinant protein. Mammalian cells are preferred for expression and production of the recombinant of the present invention; however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. Other, non-limiting, examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

When using the cell culture techniques of the instant invention, the protein of interest can be produced intracellularly, in the periplasmic space, or directly secreted into the medium. In embodiments where the protein of interest is produced intracellularly, the particulate debris, either host cells or lysed cells (e.g., resulting from homogenization), can be removed by a variety of means, including but not limited to, by centrifugation or ultrafiltration. Where the protein of interest is secreted into the medium, supernatants from such expression systems can be first concentrated using a commercially available protein concentration filter, e.g., an Amicon™ or Millipore Pellicon™ ultrafiltration unit, which can then be subjected to one or more additional purification techniques, including but not limited to affinity chromatography, including protein A affinity chromatography, ion exchange chromatography, such as anion or cation exchange chromatography, and hydrophobic interaction chromatography.

As used herein a "recombinant expression vector" can be any suitable recombinant expression vector, and can be used to transform or transfect any suitable host. For example, one of ordinary skill in the art would appreciate that transformation or transfection is a process by which exogenous nucleic acid such as DNA is introduced into a cell wherein the transformation or transfection process involves contacting the cell with the exogenous nucleic acid such as the recombinant expression vector as described herein. Non-limiting examples of such expression vectors are the pUC series of vectors (Fermentas Life Sciences), the pBluescript series of vectors (Stratagene, LaJolla, Calif.), the pET series of vectors (Novagen, Madison, Wis.), the pGEX series of vectors (Pharmacia Biotech, Uppsala, Sweden), and the pEX series vectors (Clontech, Palo Alto, Calif.).

As used herein, the term "recombinant protein" refers to a protein produced as the result of the transcription and translation of a gene carried on a recombinant expression vector that has been introduced into a host cell. In certain embodiments the recombinant protein is an antibody, preferably a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., a Fc fragment or a Fab fragment).

As used herein, the term "Adalimumab", also known by its trade name Humira® (Abbott Laboratories) refers to a human IgG antibody that binds the human form of tumor necrosis factor alpha. In general, the heavy chain constant domain 2 ($C_H2$) of the Adalimumab IgG-Fc region is glycosylated through covalent attachment of oligosaccharide at asparagine 297 (Asn-297). Adalimumab produced by Chinese hamster ovary (CHO) cells exists in 6 oligosaccharide forms, designated as NGA2F, NGA2F-GlcNAc, NA1F, NA2F, MS and M6. Weak cation-exchange chromatography (WCX) analysis of the antibody has shown that it has three main charged-variants (i.e. Lys 0, Lys 1, and Lys 2). These variants, or "charged isomers," are the result of incomplete posttranslational cleavage of the C-terminal lysine residues. In addition, WCX analysis has show that production of the antibody can result in the accumulation of two acidic species, identified herein as AR1 and AR2.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "control", as used herein, is intended to refer to both limitation as well as to modulation. For example, in certain embodiments, the instant invention provides methods for controlling diversity that decrease the diversity of certain characteristics of protein populations, including, but not limited to, glycosylation patterns. Such decreases in diversity can occur by: (1) promotion of a desired characteristic, such as a favored glycosylation pattern; (2) inhibition of an unwanted characteristic, such as a disfavored glycosylation pattern; or (3) a combination of the foregoing. As used herein, the term "control" also embraces contexts where heterogeneity is modulated, i.e., shifted, from one diverse population to a second population of equal or even greater diversity, where the second population exhibits a distinct profile of the characteristic of interest. For example, in certain embodiments, the methods of the instant invention can be used to modulate the types of oligosaccharide substitutions present on proteins from a first population of substitutions to a second equally diverse, but distinct, population of substitutions.

5.2 Control of Protein Heterogeneity 5.2.1 Supplementation of CD Media with Yeast and/or Plant Hydrolysates It is well known that the pattern of glycoforms that arise in recombinant proteins, including monoclonal antibodies, can be affected by culture conditions during production. (Nam et al., The effects of culture conditions on the glycosylation of secreted human placental alkaline phosphatase produced in Chinese hamster ovary cells. Biotechnol Bioeng. 2008 Aug. 15; 100(6): 1178-92). Consistency in the quality of the glycoproteins is important because glycosylation may impact protein solubility, activity, and circulatory half-life. (Gawlitzek et al., Effect of Different Cell Culture Conditions on the Polypeptide Integrity and N-glycosylation of a Recombinant Model Glycoprotein, Biotechnol. Bioeng. 1995; 46:536-544; and Hayter et al., Glucose-limited Chemostat Culture of Chinese Hamster Ovary Cells Producing Recombinant Human Interferon-γ. Biotechnol. Bioeng. 1992; 39:327-335).

In certain instances, such glycosylation-based heterogeneity can take the form of differences in the galactose composition of N-linked oligosaccharides. For example, a terminal galactose is added to NGA2F by β-galactosyltransferase enzyme in the presence of manganese chloride, to produce NA1F (in the case of an addition of a single terminal galactose) or NA2F (in the case of an addition of two terminal galactose molecules). This galactosyltransferase-mediated reaction employs UDP-galactose as the sugar substrate and $Mn^{2+}$ as a cofactor for galactosyltransferase. Thus, without being bound by theory, it is believed that a change in protein homogeneity taking the form of an increase in the fraction of N-linked oligosaccharide NGA2F and a decrease in the fraction of NA1F+NA2F N-linked oligosaccharides could be caused by either an insufficient amount of the substrate (UDP-galactose), the cofactor for galactosyltransferase ($Mn^{2+}$), or both.

The experiments disclosed herein demonstrate that, in certain embodiments, supplementation of CD cell culture media with yeast and/or plant hydrolysates can modulate product quality of a mAb by, in certain embodiments, decreasing the NGA2F+NGA2F-GlcNac and, in certain embodiments, increasing the NA1F+NA2F oligosaccharides. These results were achieved in multiple CD media available from multiple vendors (Life Sciences Gibco, HyClone, and Irvine Scientific), using yeast and/or plant hydrolysates (for example, but not by way of limitation, soy, wheat, rice, cotton seed, pea, corn, and potato) from multiple vendors (BD Biosciences, Organotechnie, Sheffield/Kerry Biosciences, Irvine Scientific, and DMV International). In experiments where yeast or plant hydrolysates were added individually, a dose-dependent effect in the extent of reduction of NGA2F+NGA2F-GlcNac oligosaccharides (and a corresponding increase in the NA1F+NA2F oligosaccharides) with increasing yeast or plant hydrolysates concentration in culture CD media was observed. For example, but not by way of limitation, yeast hydrolysates can be used to supplement a CD cell culture media at concentrations ranging from about 2 g/L to about 11 g/L to achieve the desired reduction of NGA2F+NGA2F-GlcNac oligosaccharides and a corresponding increase in the NA1F+NA2F oligosaccharides. In certain non-limiting embodiments, yeast hydrolysates can be used to supplement a CD cell culture media at concentrations of about 2 g/L, about 5 g/L, or about 11 g/L. In certain non-limiting embodiments, plant hydrolysates can be used to supplement a CD cell culture media at concentrations ranging from about 2 g/L to about 15 g/L to achieve the desired reduction of NGA2F+NGA2F-GlcNac oligosaccharides and a corresponding increase in the NA1F+NA2F oligosaccharides. In certain non-limiting embodiments, plant hydrolysates can be used to supplement a CD cell culture media at concentrations of about 2 g/L, about 4 g/L, 7 g/L, 10 g/L, or about 15 g/L.

In certain embodiments, the concentration of yeast and/or plant hydrolysates is maintained in such a manner as to reduce the NGA2F+NGA2F-GlcNac sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding. In certain embodiments, the concentration of yeast and/or plant hydrolysates is maintained in such a manner as to increase the NA1F+NA2F sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, control over the glycosylation distribution of proteins produced by cell culture can be exerted by maintaining the appropriate yeast hydrolysate concentration in the cell culture expressing the protein of interest as described herein. Specific culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line 5.2.2 Changing Yeast to Plant Hydrolysate Ratio in Cell Culture Medium The instant disclosure relates to control of the glycosylation distribution in mammalian cell culture processes, including where specific components, such as hydrolyzed yeast and soy-based supplements, are commonly used and are typical constituents of suspension culture media in such processes. These nutrients are important for ensuring both robust cell growth and production of glycoproteins. However, the present invention utilizes these components in such a way to affect the critical quality attributes of the glycoprotein. For example, but not by way of limitation, by adjusting the concentration ratio of these two hydrolysates, yeast and soy (phytone), within the range of about 0.25 to about 1.55, the resultant glycosylation distribution can be modified. As outlined in Example 1, non-limiting embodiments of the present invention include supplements comprising 100% yeast hydrolysate as well as those that are 100% plant hydrolysate. Thus, this disclosure provides a means to modulate glycosylation variations introduced by process inputs, such as raw materials, and other variability inherent in dynamic manufacturing operations. Ultimately, the disclosure enables in-process control of protein glycosylation with respect to desired product specifications.

In certain embodiments, the ratio of these two hydrolysates, yeast and soy (phytone), is maintained in such a manner as to reduce the NGA2F+NGA2F-GlcNac sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding. In certain embodiments, the ratio of these two hydrolysates, yeast and soy (phytone), is maintained in such a manner as to increase the NA1F+NA2F sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, control over the glycosylation distribution of protein produced by cell culture can be exerted by maintaining the appropriate yeast to plant hydrolysate ratio in the cell culture expressing the protein of interest as described herein. Specific culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line 5.2.3 Supplementation with Asparagine The instant disclosure relates to control of the glycosylation distribution in mammalian cell culture processes, including where specific components, such as amino acids and amino acid-based supplements, are commonly used and are typical constituents of suspension culture media. These nutrients are important for ensuring both robust cell growth and production of glycoproteins. However, this present invention utilizes these components, and in particular asparagine and/or glutamine in such a way to affect the critical quality attributes of the glycoprotein. For example, but not by way of limitation, by adjusting the concentration of one or both of these two amino acids the resultant glycosylation distribution can be modified. Thus, this disclosure provides a means to modulate glycosylation variations introduced by process inputs, such as raw materials, and other variability inherent in dynamic manufacturing operations. Ultimately, the disclosure enables in-process control of protein glycosylation with respect to desired product specifications.

The experiments disclosed herein demonstrate that, in certain embodiments, supplementation of cell culture media with asparagine and/or glutamine can modulate product quality of a mAb by, in certain embodiments, increasing the NGA2F+NGA2F-GlcNac and, in certain embodiments, decreasing the NA1F+NA2F oligosaccharides. For example, but not by way of limitation, the percentage of NGA2F+NGA2F-GlcNac can be increased by 2-4% and the percentage of NA1F+NA2F was decreased by 2-5% when 0.4 to 1.6 g/L asparagine is added on either day 0 or days 6 or 7, as outlined in Example 5, below. Similarly, addition of 0.4 g/L glutamine, to the culture run described in Example 5, below, increased the percentage of NGA2F+NGA2F-GlcNac by 1% and lowered the percentage of NA1F+NA2F by 1%. Finally, adding both asparagine and glutamine (0.4 g/L of each), to the cell culture run described in Example 5, below, increased the percentage of NGA2F+NGA2F-GlcNac by 3% and decreased the percentage of NA1F+NA2F by 4%. In addition, the cell growth profile is the same when 0.8 and 1.6 g/L of asparagine was added, but a dose dependent effect on oligosaccharide distribution was observed, indicating that the effect on oligosaccharide distribution was due to the addition of asparagine and not the increased maximum viable cell density or delayed drop in viability. In certain embodiments, the total amount of asparagine in the cell culture media will range from about 0 mM to about 26 mM. In certain embodiments, for example those embodiments where a hydrolysate media is employed, the range of asparagine in the cell culture media will range from about 1.3 mM to about 14.6 mM. In certain embodiments, for example, but not limited to, those embodiments where GIA1 media is employed, the range of asparagine in the cell culture media will range from about 12.3 mM to about 25.7 mM.

In certain embodiments, the concentration of asparagine and/or glutamine is maintained in such a manner as to reduce the NA1F+NA2F sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding. In certain embodiments, the concentration of asparagine and/or glutamine is maintained in such a manner as to increase the NGA2F+NGA2F-GlcNac sum in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, control over the glycosylation distribution of protein produced by cell culture can be exerted by maintaining the appropriate asparagine and/or glutamine concentration in the cell culture expressing the protein of interest as described herein. Specific culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line.

EXAMPLES

Example 1

Control of Heterogeneity by Addition of Hydrolysates to CD Media GIA-1 for Culture of an Adalimumab-Producing CHO Cell Line #1

Control of heterogeneity of therapeutic monoclonal antibodies (mAbs) can aid in ensuring their efficacy, stability, immunogenicity, and biological activity. Media composition has been shown to play a role in product quality of mAbs together with process conditions and choice of cell line. In certain embodiments, the present invention provides methods for fine-tuning the product quality profile of a mAb produced in various Chinese hamster ovary (CHO) cell lines by supplementation of yeast and/or plant hydrolysates to chemically defined (CD) media. In certain embodiments, the resulting mAb product is characterized by having a decreased content of complex agalactosylated glycans NGA2F and NGA2F-GlcNac and increased levels of terminally galactosylated glycans NA1F and NA2F. In certain embodiments, addition of increasing amounts of yeast, soy or wheat hydrolysates from several suppliers to a CD medium resulted in altered product quality profiles in a concentration-dependent manner.

In the studies summarized in this example, the effects on glycosylation resulting from the addition of yeast (Bacto TC Yeastolate: 2, 5, 11 g/L), soy (BBL Phytone Peptone: 2, 4, 7, 10, 15 g/L), or wheat (Wheat Peptone E1: 2, 4, 7, 10, 15 g/L) hydrolysates to CD medium GIA-1 (Life Technologies Gibco; proprietary formulation) in the adalimumab-producing CHO cell line #1 were investigated.

1.1 Materials And Methods

Adaptation and production media were supplemented with Bacto TC Yeastolate, BBL Phytone Peptone, or Wheat Peptone E1 according to the experimental design in FIG. 39. The control cultures were not supplemented with hydrolysates. In addition to hydrolysates, adaptation media was supplemented with 0.876 g/kg L-glutamine and 2.0 mL/kg methotrexate solution, and production media was supplemented with 0.584 g/L L-glutamine. The experiment was designed into two blocks. All media pH was adjusted to approximately 7.1 using 6N hydrochloric acid/5N sodium hydroxide. The media osmolality was adjusted to 290-300 mOsmol/kg with sodium chloride.

The adalimumab-producing cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. At each passage, cultures were inoculated at an initial viable cell density (VCD) of approximately $0.5 \times 10^6$ cells/mL.

Production cultures were initiated in duplicate 500 mL Corning, vented, non-baffled shake flasks each containing 200 mL culture in dry incubators at 35° C., 5% $CO_2$, and 110 RPM. Initial VCD was approximately $0.5 \times 10^6$ cells/mL. A 1.25% (v/v) 40% glucose stock solution was fed when the media glucose concentration was less than 3 g/L.

For all studies described throughout this application, samples were collected daily and measured for cell density and viability using a Cedex cell counter. Retention samples for titer analysis (2×1.5 mL per condition) via Poros A method were collected daily after culture viability fell below 90%. Samples were centrifuged at 12,000 RPM for 5 min and the supernatant was stored at −80° C. until further analysis. The harvest procedure was performed by centrifugation of the culture sample at 3,000 RPM for 30 min followed by storage of the supernatant in 125 mL PETG bottles at −80° C. until protein A purification, oligosaccharide, and WCX-10 analysis.

For the oligosaccharide assay, the oligosaccharides are released from the protein by enzymatic digestion with N-glycanase. Once the glycans are released, the free reducing end of each glycan is labeled by reductive amination with a fluorescent tag, 2-aminobenzamide (2-AB). The resulting labeled glycans are separated by normal-phase HPLC(NP-HPLC) in acetonitrile: 50 mM ammonium formate, pH 4.4, and detected by a fluorescence detector. Quantitation is based on the relative area percent of detected sugars. The relative area percents of the agalactosyl fucosylated biantennary oligosaccharides (NGA2F+[NGA2F-GlcNac]) and the galactose-containing fucosylated biantennary oligosaccharides NA1F+NA2F are reported and discussed.

1.2 Culture Growth and Productivity

Figure 1B:
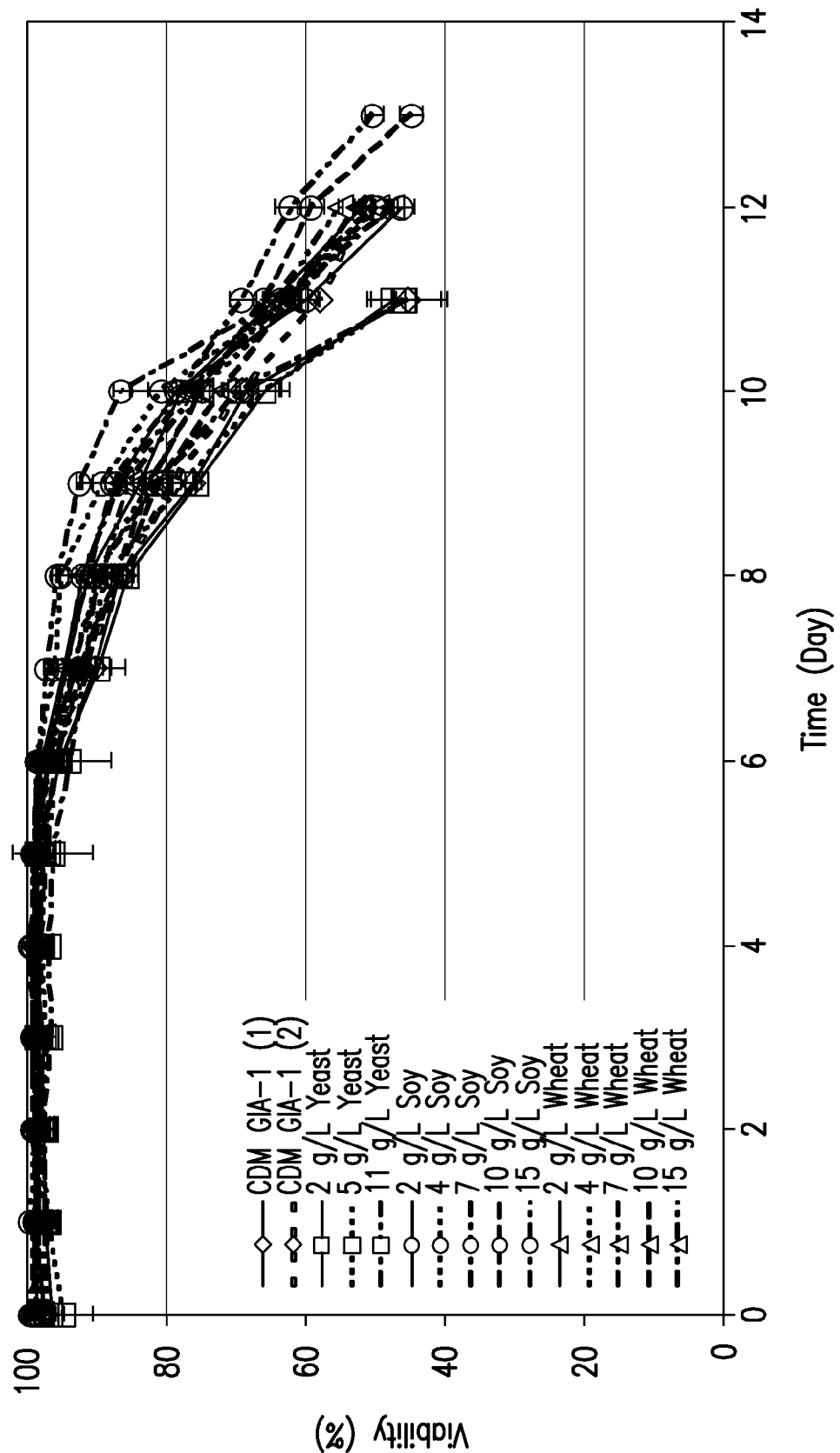
Figure 1C:
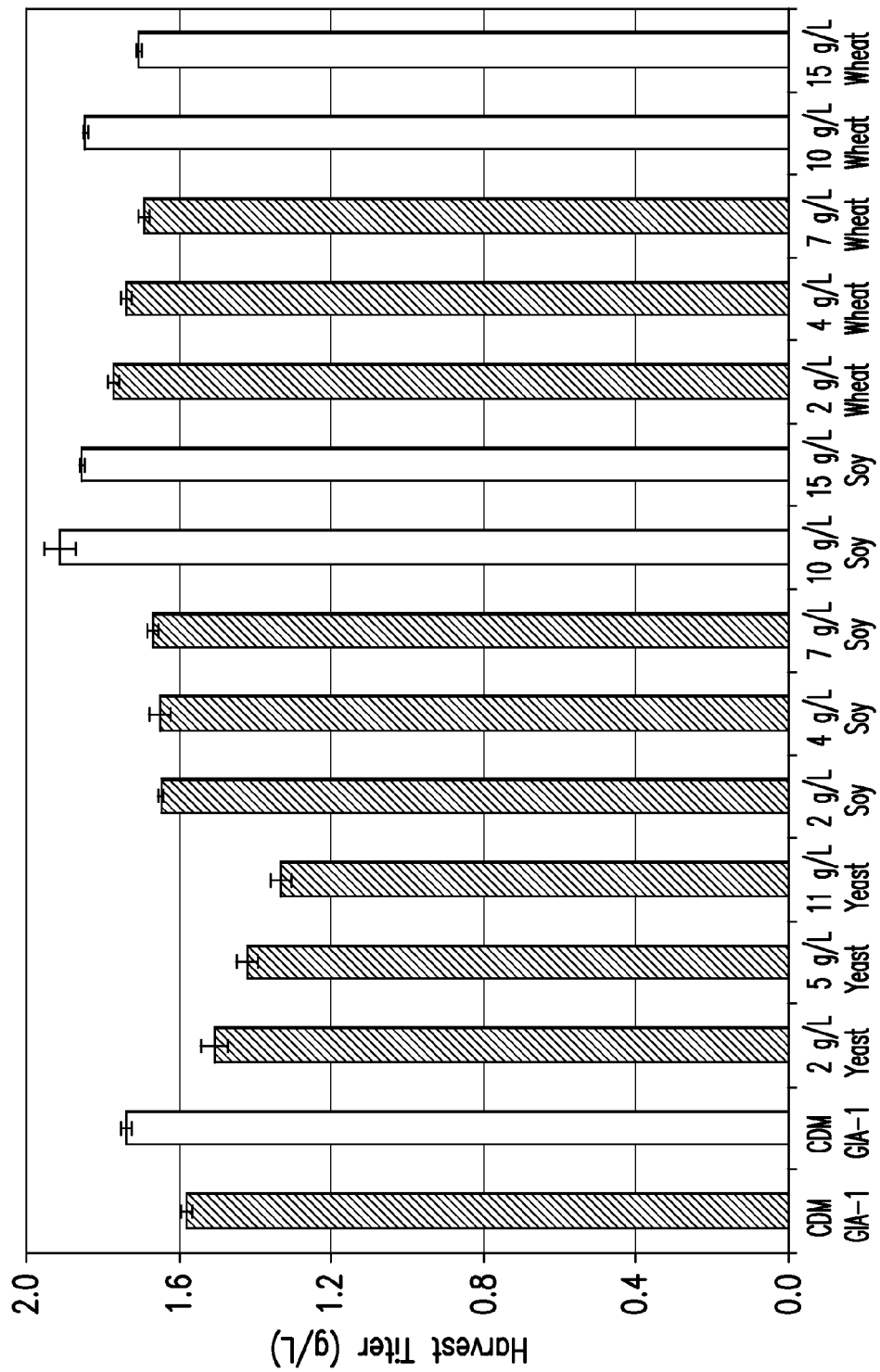

The majority of cultures grew to a similar peak VCD in the range of $9-11 \times 10^6$ cells/mL. Cultures supplemented with 11 g/L yeast hydrolysate BD TC yeastolate experienced slight inhibition of growth (FIG. 1A). Viability profiles were comparable to the control condition with cultures lasting 11 to 13 days (FIG. 1B). Increasing the yeast hydrolysate concentration in CDM media GIA-1 resulted in decreased average productivity compared to the control condition. Cultures supplemented with soy or wheat hydrolysates lasted 12 to 13 days, and experienced slightly increased average titer compared to the control condition (FIG. 1C).

1.3 Oligosaccharide Analysis

Figure 2A:
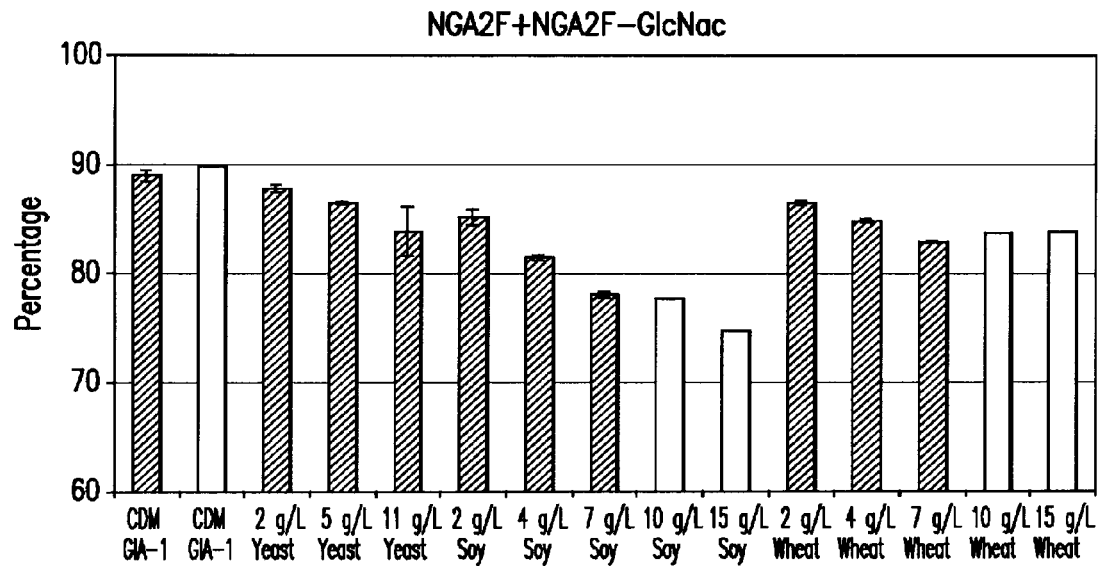
FIG. 2 depicts the effect of yeast, soy, or wheat hydrolysate addition to CDM GIA-1 in adalimumab-producing CHO cell line #1 on (a) NGA2F+NGA2F-GlcNac and (b) NA1F+NA2F.
Figure 2B:
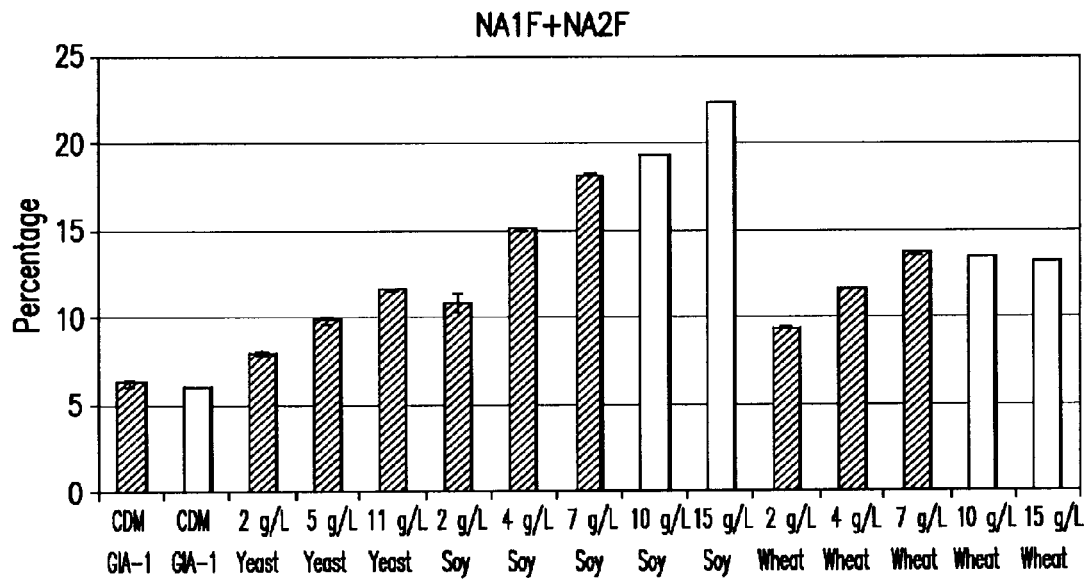

Addition of yeast, soy, or wheat hydrolysates to CD media GIA-1 lowered the percentage of glycans NGA2F+NGA2F-GlcNac by 1-14% and increased the percentage of NA1F+NA2F glycans by 2-12% compared to control condition (NGA2F+NGA2F-GlcNac: 89%; NA1F+NA2F: 6%) (FIGS. 2A-B). A dose-dependent decrease in NGA2F+NGA2F-GlcNac and a corresponding increase in NA1F+NA2F glycans was observed with the addition of yeast, soy, or wheat hydrolysate over the tested range. The highest percentage decrease in NGA2F+NGA2F-GlcNac and corresponding highest increase in NA1F+NA2F glycans was recorded for the condition supplemented with 7 g/L BD BBL phytone peptone (NGA2F+NGA2F-GlcNac: 78%, and NA1F+NA2F: 18%) compared to control.

Example 2

Yeast and Soy Hydrolysates Combined Addition to Multiple Commercially Available CD Media for Culture of an Adalimumab-Producing CHO Cell Line #1

In the study summarized in this example, the effects of combined yeast and soy hydrolysates addition to CD media from multiple suppliers: Life Technologies Gibco (OptiCHO and GIA-1), Irvine Scientific (IS CHO-CD), and HyClone/Thermo Scientific (CDM4-CHO) on product quality in the adalimumab-producing CHO cell line #1 utilized in Example 1 were evaluated.

2.1 Materials and Methods

The liquid or powder formulation media were purchased from multiple vendors (Life Technologies Gibco—OptiCHO and GIA-1; Irvine Scientific—IS CHO-CD; and HyClone/Thermo Scientific—CDM4-CHO), reconstituted per the manufacturers' recommendations, and supplemented with Bacto TC Yeastolate and BBL Phytone Peptone according to the experimental design in FIG. 40. The control cultures for each condition were not supplemented with hydrolysates. All media pH was adjusted to approximately 7.1 using 6N hydrochloric acid/5N sodium hydroxide.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning vented non-baffled shake flasks at an initial VCD of approximately $0.5 \times 10^6$ cells/mL. The shake flask study was run in an extended batch-mode by feeding a glucose solution (1.25% (v/v) of 40% solution) when the media glucose concentration fell below 3 g/L.

2.2 Culture Growth and Productivity

Figure 3A:
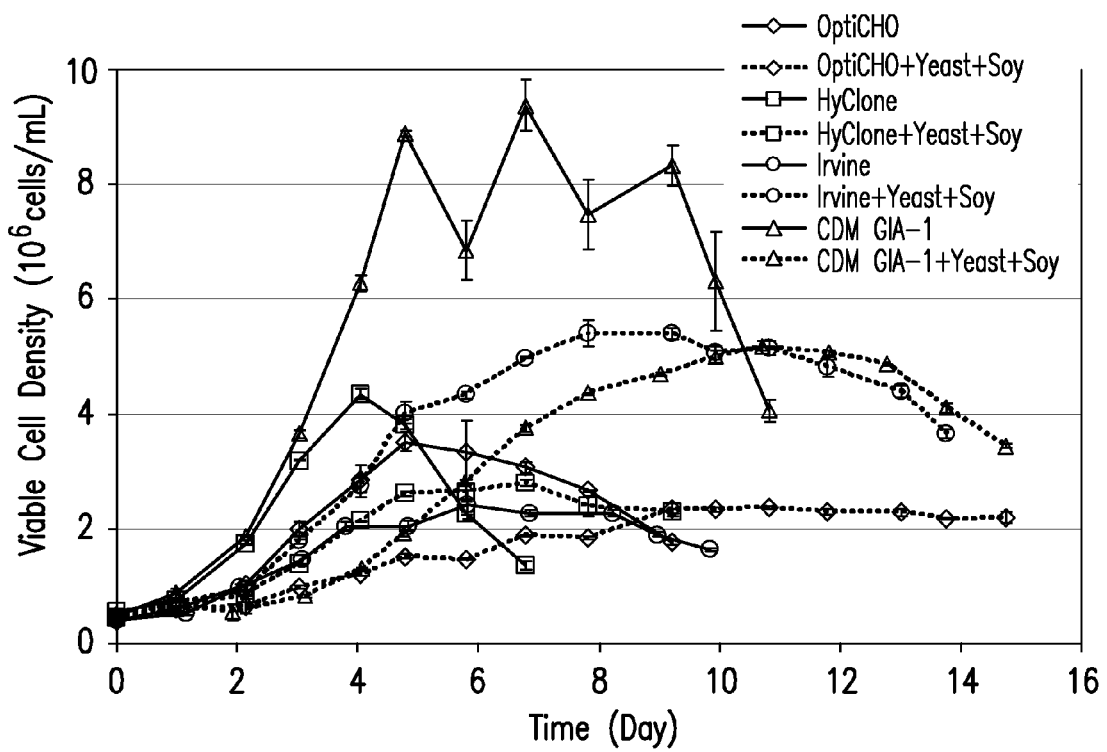
FIG. 3 depicts the effect of combined supplementation of yeast and soy hydrolysates to CD media from multiple suppliers in adalimumab-producing CHO cell line #1 on (a) Culture growth, (b) Culture viability, and (c) Harvest titer.
Figure 3B:
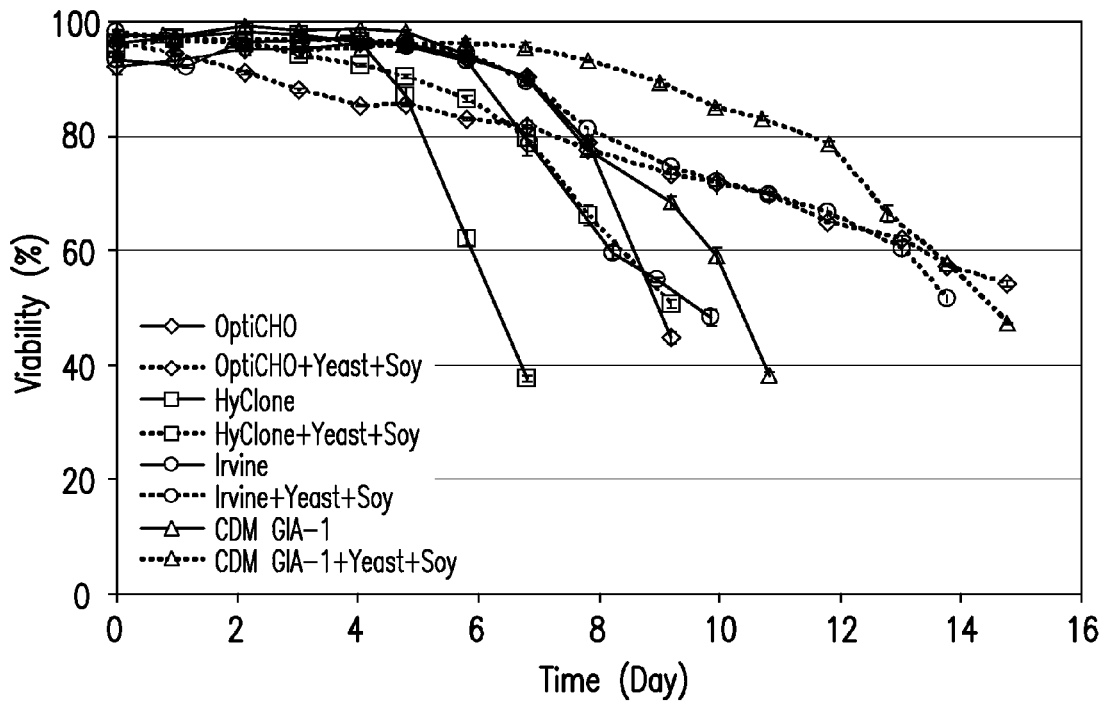
Figure 3C:
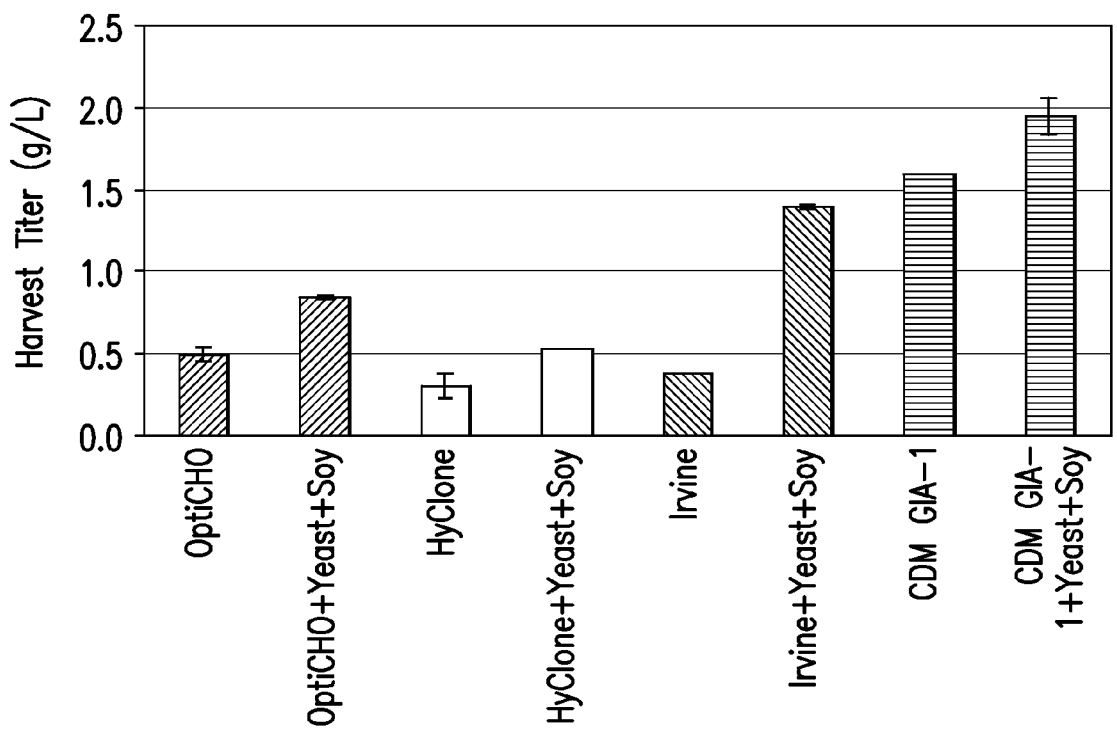

Commercially available CD media supported markedly different culture growth profiles with maximum VCD of $2-9 \times 10^6$ cells/mL and culture duration ranging from 7 to 15 days (FIG. 3A). Addition of yeast and soy hydrolysates to Life Technologies Gibco OptiCHO and GIA-1, and HyClone CDM4-CHO media decreased peak VCD and increased culture length by 2 to 6 days. However, addition of hydrolysates to Irvine IS CHO-CD media increased peak VCD from $2.5 \times 10^6$ cells/mL to $5.4 \times 10^6$ cells/mL. Culture viability declined slower with addition of hydrolysates for all media tested (FIG. 3B). Productivity also varied significantly among cultures; however, the addition of hydrolysates to CD media increased productivity in all cases (FIG. 3C).

2.3 Oligosaccharide Analysis

Figure 4A:
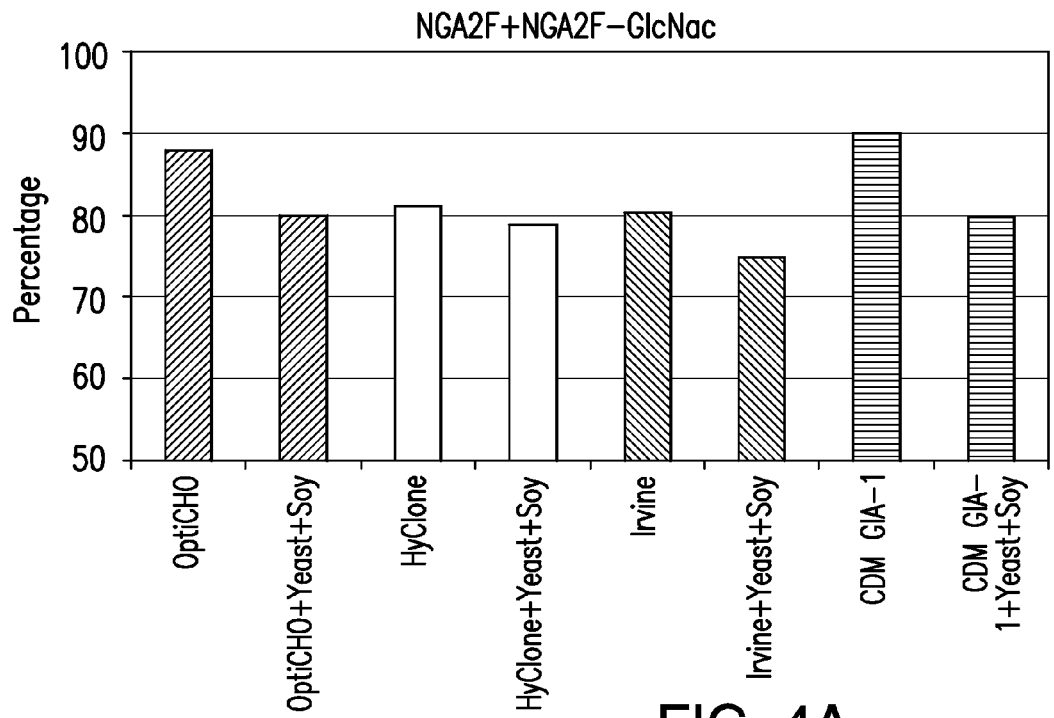
FIG. 4 depicts the effect of combined supplementation of yeast and soy hydrolysates to CD media from multiple suppliers in adalimumab-producing CHO cell line #1 on (a) NGA2F+NGA2F-GlcNac and (b) NA1F+NA2F.
Figure 4B:
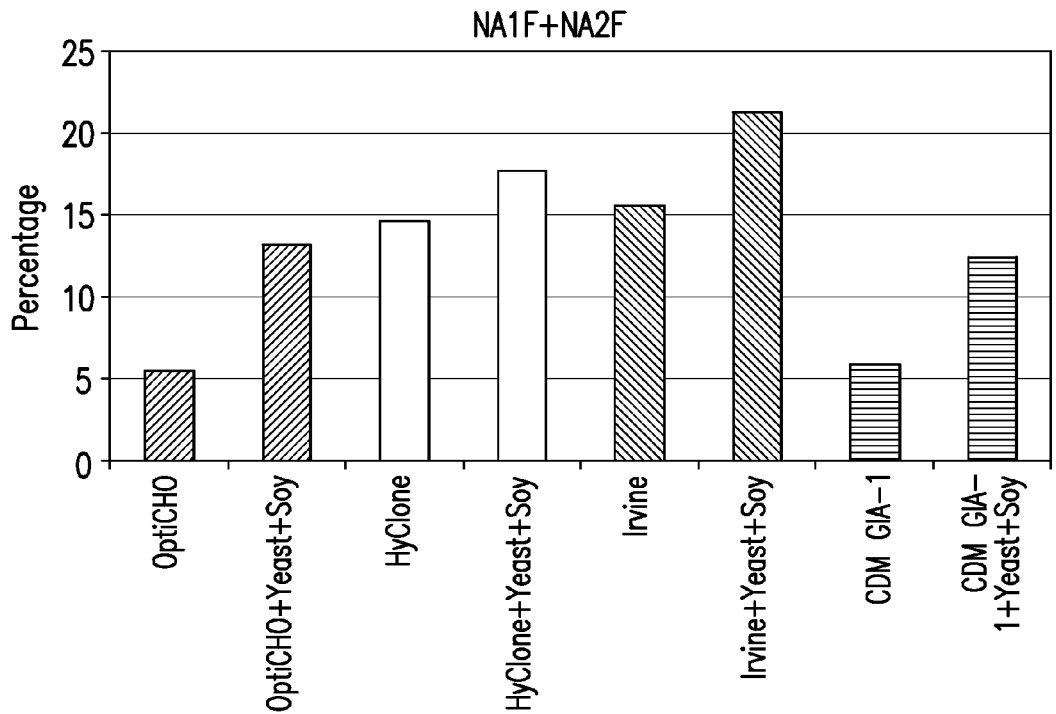
Figure 5A:
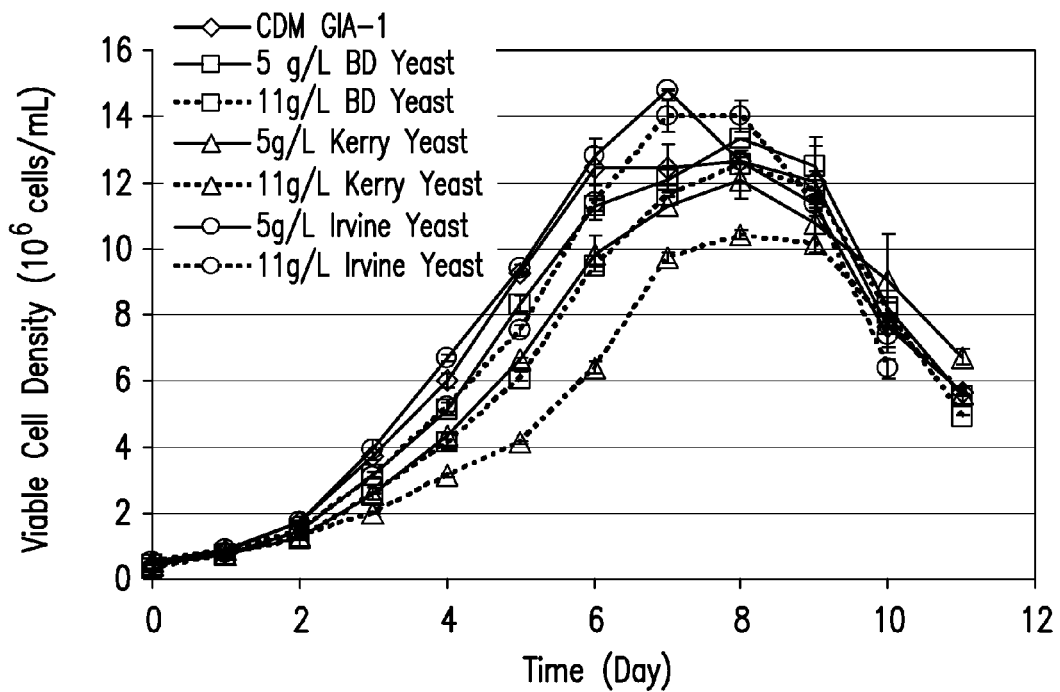
FIG. 5 depicts the effect of supplementing (a) yeast, (b) soy, or (c) wheat hydrolysate from multiple vendors to CDM GIA-1 on culture growth in CHO cell line #1.
Figure 5B:
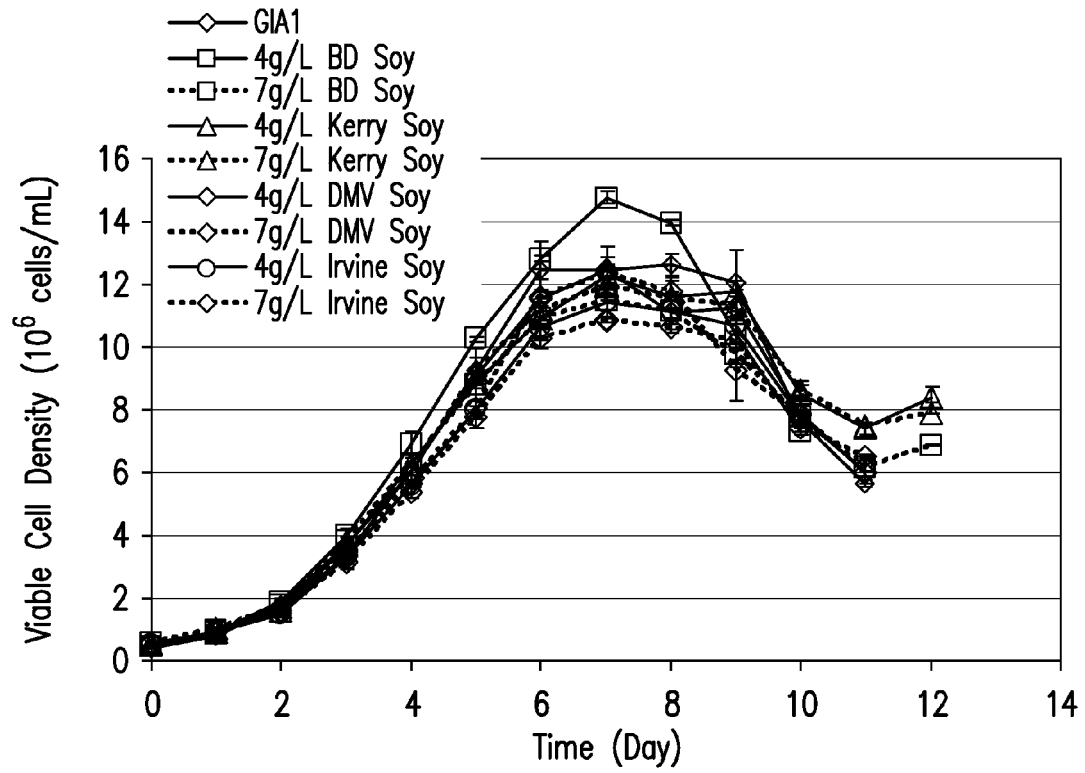
Figure 5C:
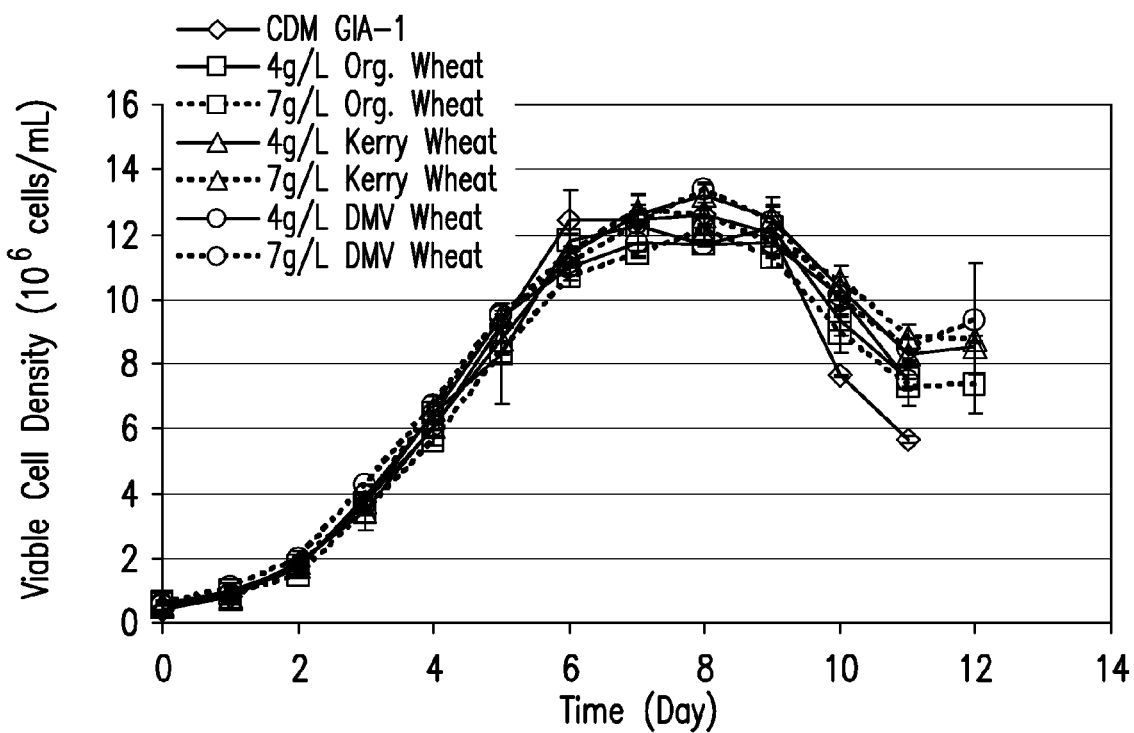
Figure 6A:
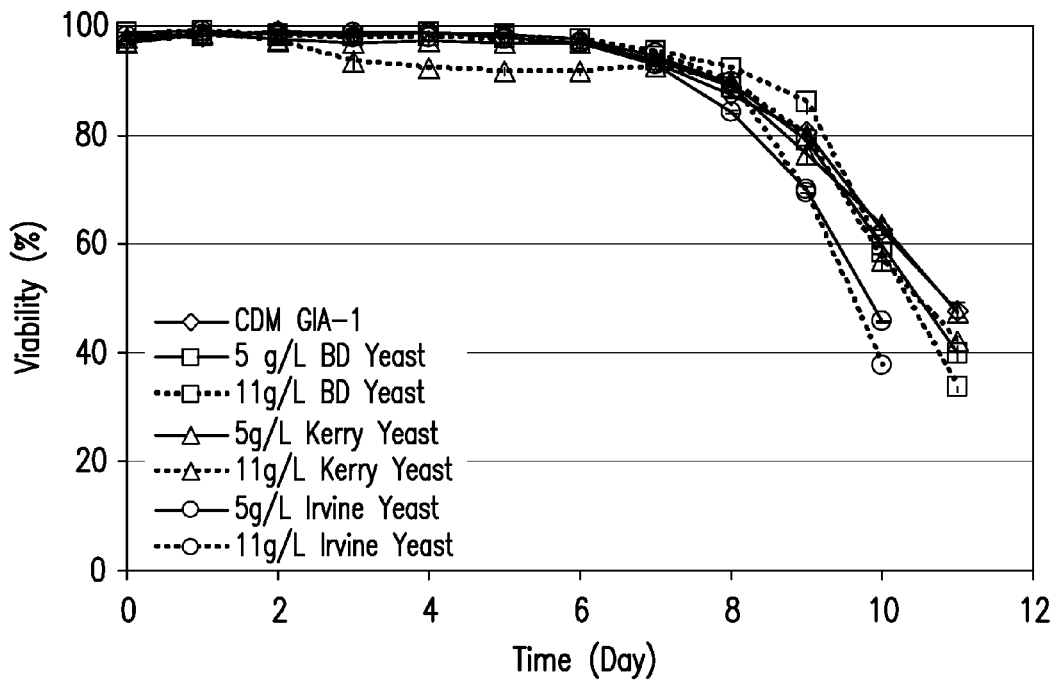
FIG. 6 depicts the effect of supplementing (a) yeast, (b) soy, or (c) wheat hydrolysate from multiple vendors to CDM GIA-1 on culture viability in CHO cell line #1.
Figure 6B:
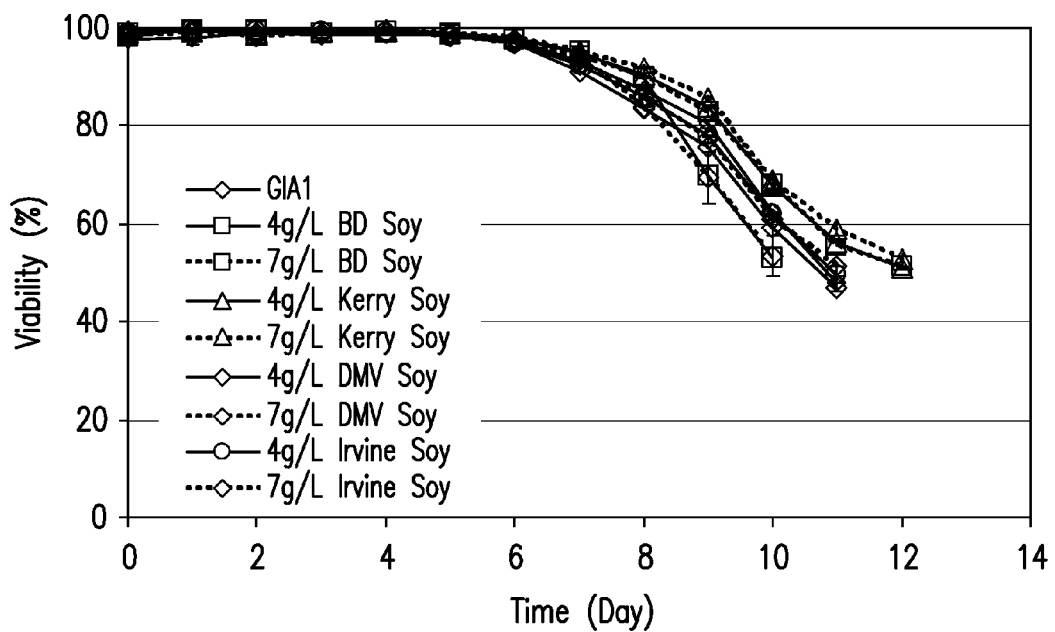
Figure 6C:
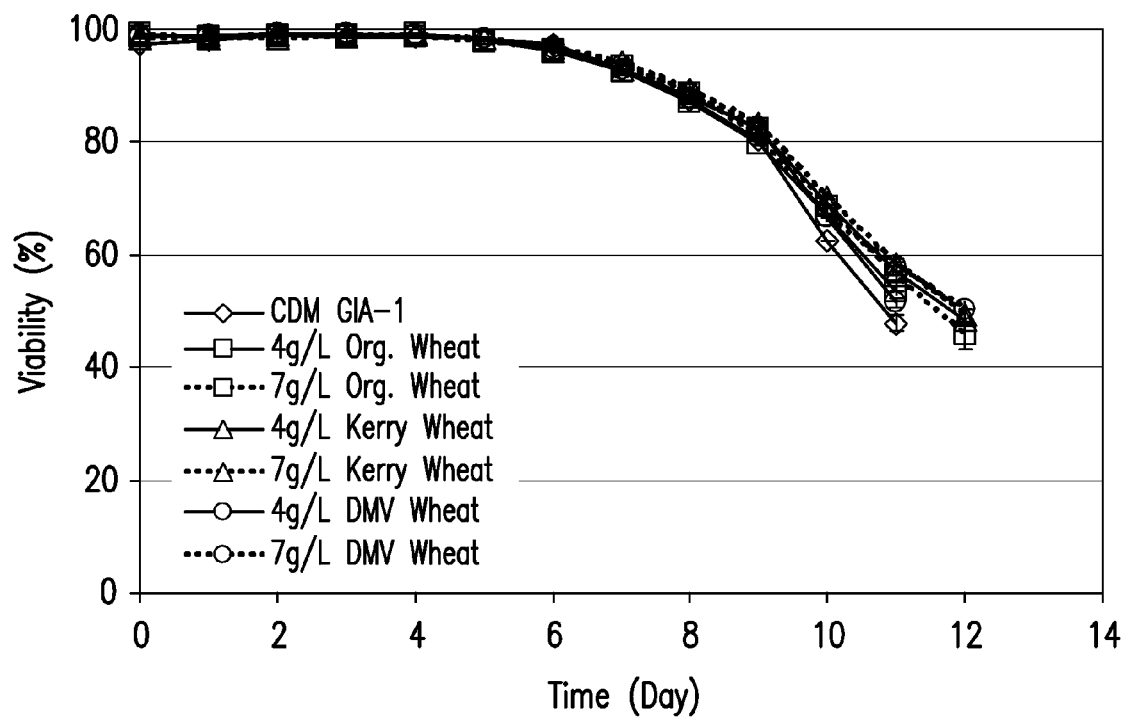

The combined addition of yeast and soy hydrolysates to various commercially available CD media lowered the percentage of NGA2F+NGA2F-GlcNac glycans by 2-10% compared to control (FIG. 4A): from 81% to 79% (HyClone CDM4-CHO); from 80% to 75% (Irvine IS CHO-CD); from 88% to 80% (Life Technologies OptiCHO); from 90% to 80% (Life Technologies GIA-1). The percentage of NA1F+NA2F glycans increased by 3-8% compared to control (FIG. 4B): from 15% to 18% (HyClone CDM4-CHO); from 6% to 12%

(Life Technologies GIA-1); from 16% to 21% (Irvine IS CHO-CD); from 5% to 13% (Life Technologies OptiCHO).

Example 3

Supplementation of Yeast, Soy and Wheat Hydrolysates from Multiple Vendors to CD Media GIA-1 for Culture of an Adalimumab-Producing CHO Cell Line #1

In the study summarized in this example, we investigated the effects on glycosylation resulting from the addition of yeast (5, 11 g/L), soy (4, 7 g/L) or wheat (4, 7 g/L) hydrolysates from multiple vendors (BD Biosciences, Sheffield/Kerry Biosciences, DMV International, Irvine Scientific, and Organotechnie) to CDM GIA-1 in the adalimumab-producing CHO cell line #1.

3.1 Materials and Methods

Adaptation and production media were supplemented with Bacto TC Yeastalate, BBL Phytone Peptone, or Wheat Peptone E1 according to the experimental design in FIG. 41. The control cultures were not supplemented with hydrolysates. All media pH was adjusted to approximately 7.1 using 6N hydrochloric acid/5N sodium hydroxide. The media osmolality was adjusted to 290-300 mOsmol/kg with sodium chloride.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning, vented, non-baffled shake flasks at an initial VCD of approximately $0.5 \times 10^6$ cells/mL. The shake flask study was run in an extended-batch mode by feeding a glucose solution (1.25% (v/v) of 40% solution) when the media glucose concentration fell below 3 g/L.

3.2 Culture Growth and Productivity

Figure 7:
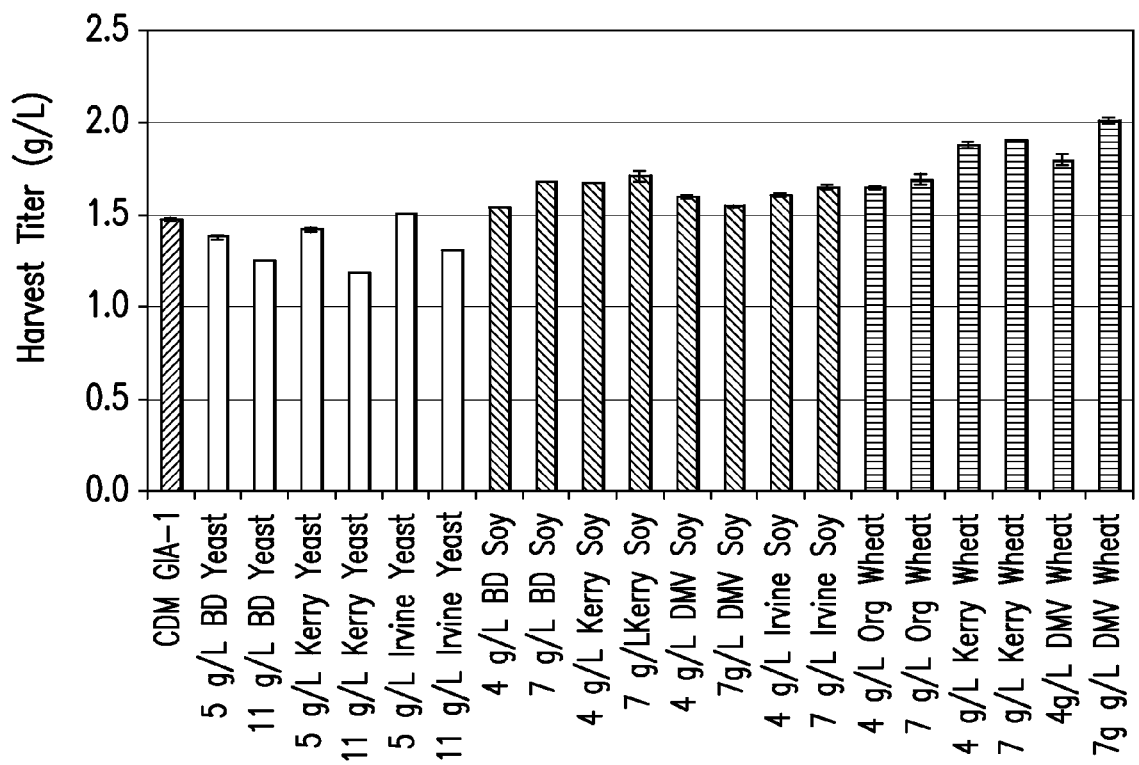
FIG. 7 depicts the effect of supplementing yeast, soy, or wheat hydrolysate from multiple vendors to CDM GIA-1 on harvest titer in CHO cell line #1.

Culture growth and viability profiles were comparable among all test conditions (FIGS. 5A-C, 6A-C) except for 11 g/L BD Bacto TC yeastolate, for which a slight decrease in the growth rate and maximum VCD was observed. Supplementation of CD media GIA-1 with yeast hydrolysates lowered the harvest titer by up to 25% compared to the control, while the harvest titer increased up to 14% and 27% with the addition of soy or wheat hydrolysates, respectively (FIG. 7).

3.3 Oligosaccharide Analysis

Figure 8A:
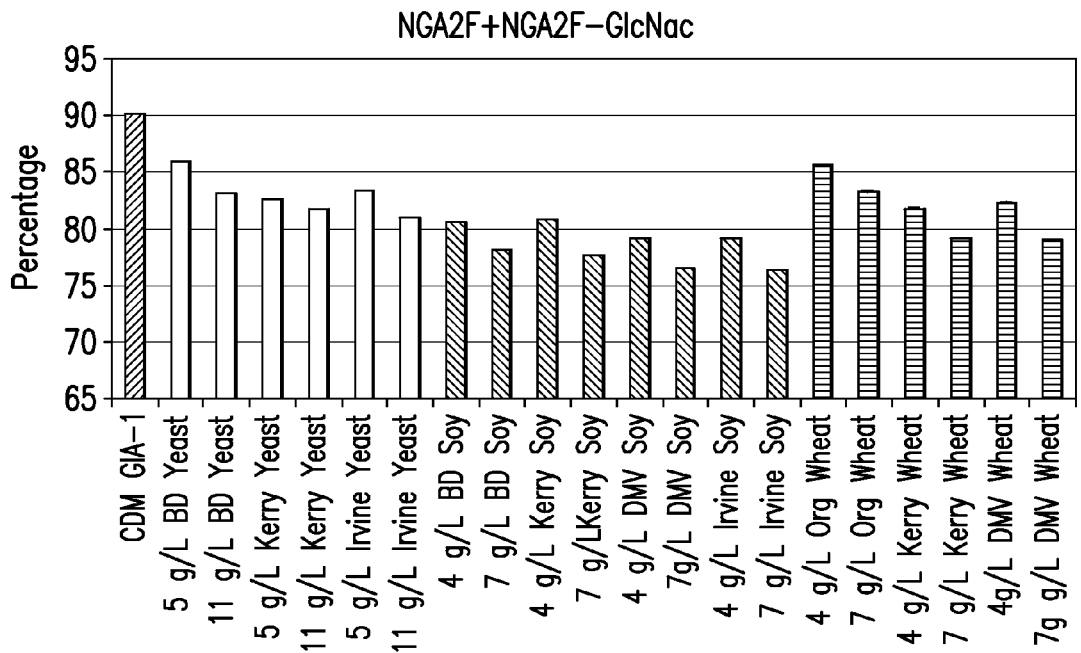
FIG. 8 depicts the effect of supplementing yeast, soy, or wheat hydrolysate from multiple vendors to CDM GIA-1 in CHO cell line #1 on (a) NGA2F+NGA2F-GlcNac and (b) NA1F+NA2F.
Figure 8B:
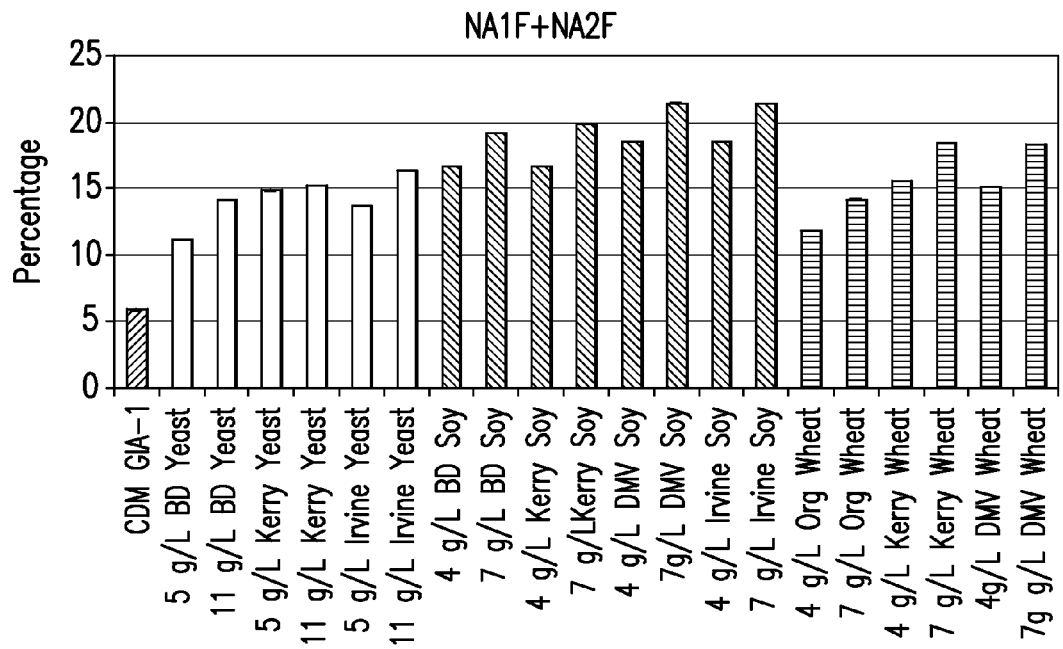

Addition of yeast, soy or wheat hydrolysates to CD media GIA-1 decreased the NGA2F+NGA2F-GlcNac glycans in a dose-dependent manner for all hydrolysate vendors evaluated (FIGS. 8A-B). Addition of yeast hydrolysates to CD media GTA-1 lowered the percentage of NGA2F+NGA2F-GlcNac glycans by 4-9%, and increased the percentage of NA1F+NA2F glycans by 5-10% compared to control (NGA2F+NGA2F-GlcNac: 90%; NA1F+NA2F: 6%). Addition of soy hydrolysates to CD media GIA-1 decreased the NGA2F+NGA2F-GlcNac glycans by 9-14%, and increased the NA1F+NA2F glycans by 11-15% compared to control. Addition of wheat hydrolysates decreased the NGA2F+NGA2F-GlcNac glycans by 4-11%, and increased the NA1F+NA2F glycans by 6-12% compared to control.

Example 4

Control of Heterogeneity by Addition of Reduced Ratio of Yeast to Plant Hydrolysate To identify the role which the ratio of yeast to plant hydrolysate plays in connection with the generation of protein heterogeneity, experiments employing a range of different hydrolysate ratios were undertaken. The cell culture medium employed in each experimental process contains both yeast and soy hydrolysate (phytone). The ratios of yeast to soy hydrolysate (by weight) are 1.55, 0.67 and 0.25. The total weight of yeastolate and soy hydrolysate were not changed in each experimental process. Two distinct yeastolate lots were used in connection with these experiments (see FIGS. 9 & 11 and 10 & 12, respectively). Culture growth, productivity and product quality were assessed. As outlined in FIGS. 9-12, reducing the yeast to soy hydrolysate ratio resulted in altered oligosaccharide profiles.

4.1. Materials and Methods

The CHO cell line #1 was employed in the studies covered here. The production medium used in this experiment contains basal medium PFCHO, Bacto TC yeastolate and phytone peptone. The pH of all media was adjusted to 7.15; and media osmolality was adjusted to 373-403 mOsmol/kg with sodium chloride. For each experiment, 500 mL shakers with 200 mL working volume were employed at the following conditions: 35° C. constant temperature; 5% $CO_2$; and 110 RPM. Cultures were inoculated at an initial viable cell density (VCD) of approximately $0.5 \times 10^6$ cells/mL. Two mL of 40% w/w glucose solution was added to each shaker when the glucose concentration dropped below 2 g/L. The shakers were harvested when the viable cell density decreased to approximately 50%. The harvest broth was centrifuged at 3200 rpm for 30 min at 5° C. to remove cells and the supernatant was stored at −80° C.

Samples were taken daily from each shaker to monitor growth. The following equipment was used to analyze the samples: Cedex cell counter, Radiometer blood gas analyzer, YSI glucose analyzer, and osmometer. The harvest samples stored at −80° C. were later thawed and analyzed for titer with Poros A HPLC method. In addition, the thawed samples were filtered through a 0.2 µm filter, purified by Protein A chromatography, and then oligosaccharide analysis was performed as described in Example 1.

4.2 Cell Growth and Productivity

Figure 9A:
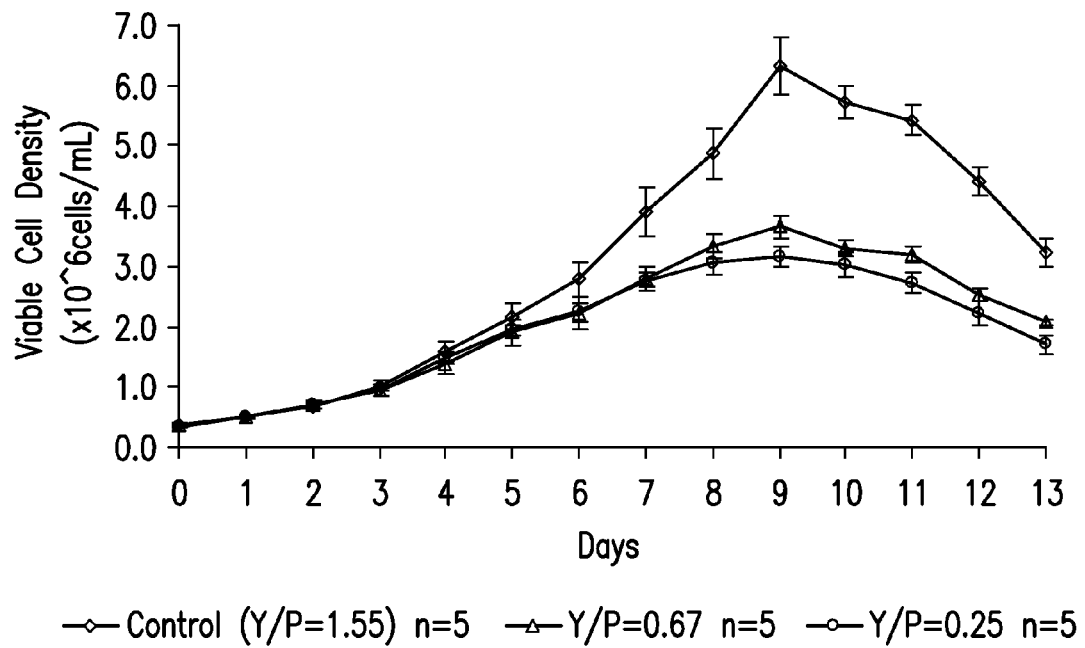
FIG. 9 depicts viable cell density and viability in Example 4: Hydrolysate study #1 using distinct ratios of yeast to soy hydrolysate in adalimumab-producing CHO cell line #1.
Figure 9B:
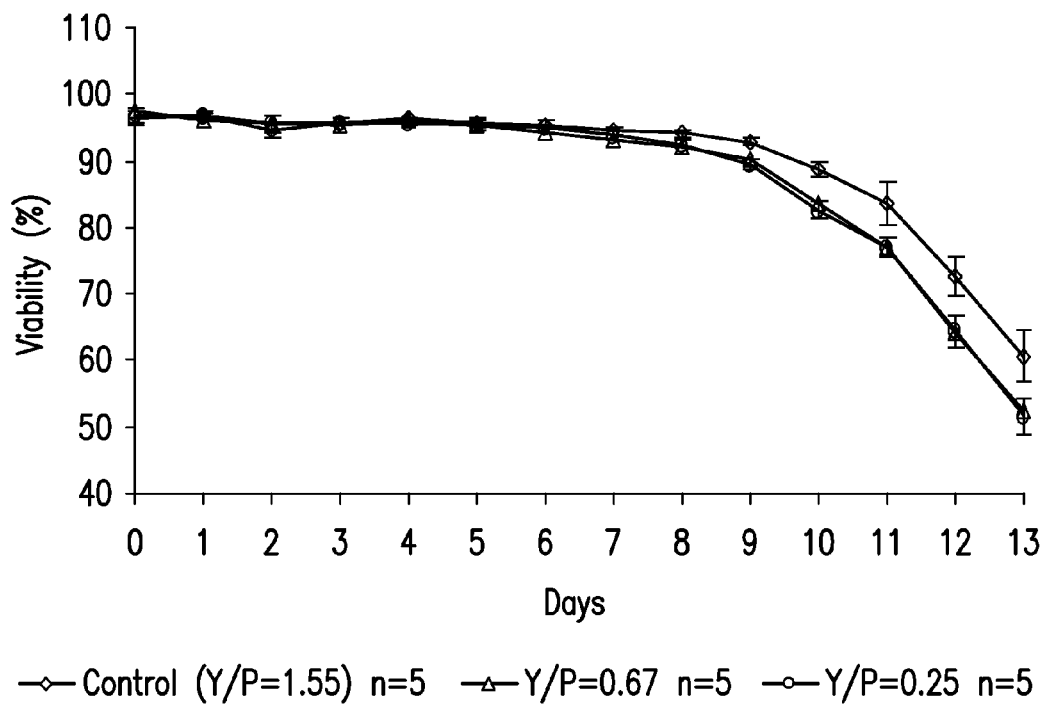
Figure 10A:
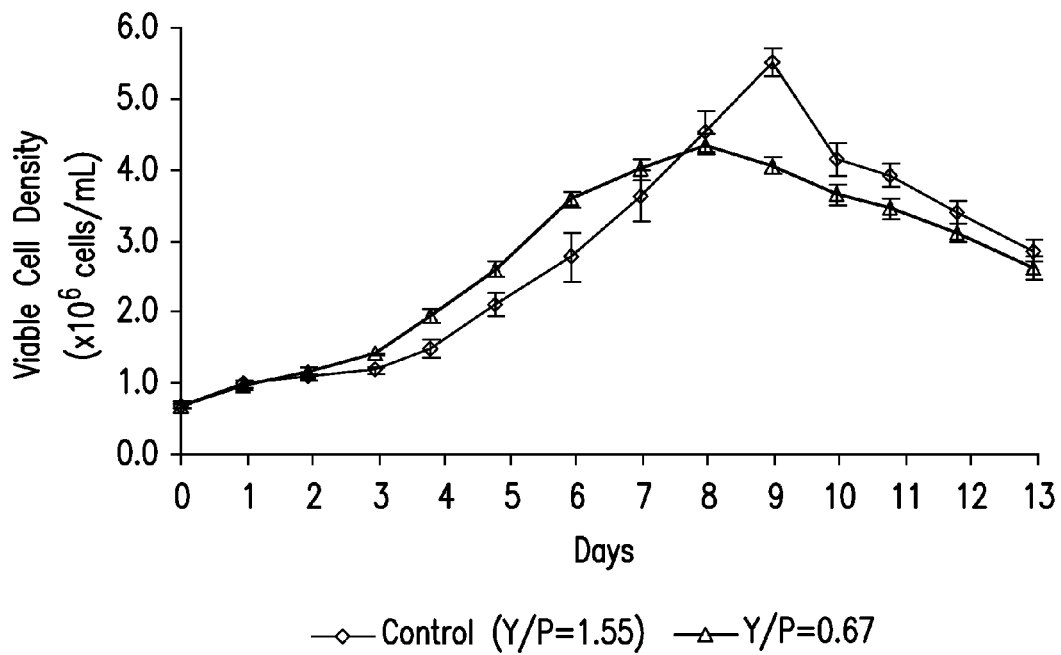
FIG. 10 depicts viable cell density and viability in Example 4: Hydrolysate study #2 using distinct ratios of yeast to soy hydrolysate in adalimumab-producing CHO cell line 41.
Figure 10B:
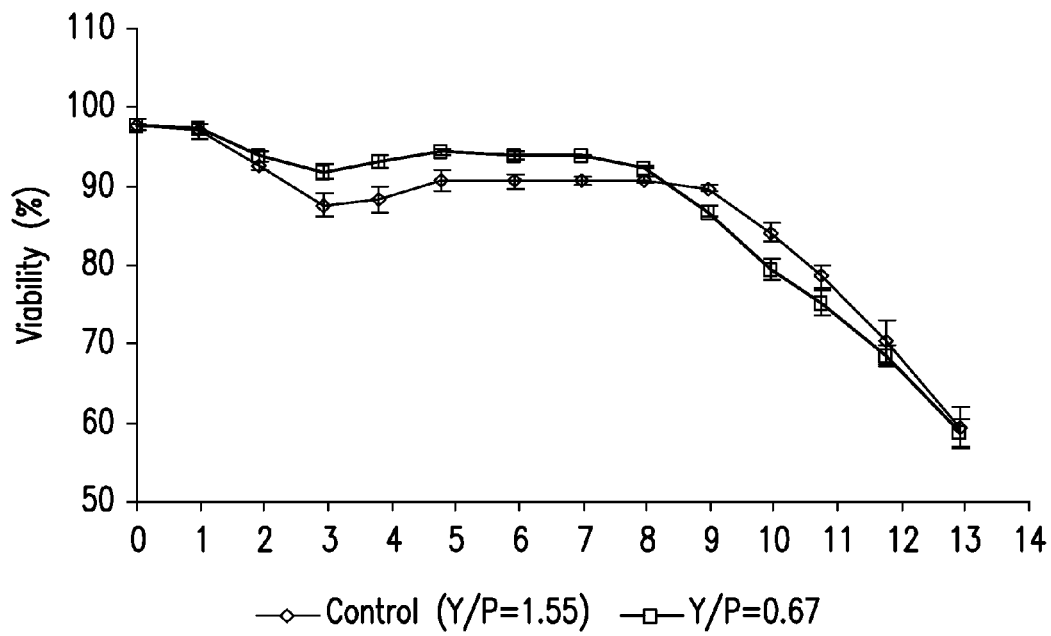

In the first hydrolysate study, the viable cell densities for the reduced ratios of yeastolate to phytone (i.e. Y/P=0.67 and Y/P=0.25) were much lower than the viable cell density for the 1.55 ratio of yeastolate to phytone (FIG. 9). As a result, the IVCC on day 13 (i.e. the harvest day) was significantly lower for the reduced ratio conditions compared to the 1.55 ratio condition, and the titer was also lower (but not statistically significantly—data not shown). The viability profiles were comparable until day 8 (FIG. 9). After day 8, the viability declined faster for the reduced ratio conditions. In hydrolysate study 2, the viable cell density and viability for the 1.55 ratio were slightly lower than those with reduced ratio in the exponential phase, but higher in the decline phase (FIG. 10). However, the titer for the 1.55 ratio shaker was 0.2 g/L lower than the reduced ratio (i.e. Y/P=0.67) (data not shown).

4.3. Oligosaccharide Analysis

Glycosylation profiles for hydrolysate studies 1 and 2 are shown in FIGS. 11 and 12, respectively. Reducing the ratio of yeastolate to phytone reduced the percentage of NGA2F+(NGA2F-GlcNAc) glycan. In hydrolysate study 1, the percentage of NGA2F+(NGA2F-GlcNAc) was significantly reduced for Y/P=0.67 and Y/P=0.25 as compared to Y/P=1.55. The p values were 0.03 and 0.001 for Y/P=0.67 and Y/P=025, respectively. At the same time, the percentage of NA1F+NA2F was increased significantly as the ratio of yeastolate to phytone was reduced.

As shown in FIG. 12 in hydrolysate study 2, the difference in the percentage of NGA2F+(NGA2F-GlcNAc) between Y/P=0.67 and Y/P=1.55 was significant (i.e. p=0.000002). The percentage of NGA2F+(NGA2F-GlcNAc) was lowered from 77.5% in the 1.55 ratio to approximately 75.4% with the reduced ratio.

Therefore, this study successfully demonstrated that reducing the ratio of yeastolate to phytone could alter oligosaccharide profile using two different lots of yeast hydrolysate.

Example 5

Control of Heterogeneity by Supplementation with Asparagine

The present invention relates to methods for modulating the glycosylation profile of a monoclonal antibody (mAb) by varying the concentration of asparagine in cell culture media. Cell culture medium components, such as asparagine, are commonly used and are typical constituents of suspension culture media. These nutrients are important for ensuring both robust cell growth and production of glycoproteins. It has been shown that the cell viability and product titer can be enhanced by the addition of asparagine to a glutamine-free production medium (Genentech, Inc. "Production of Proteins in Glutamine-Free Cell Culture Media" WO2011019619 (2010)). However, the present invention provides methods to modify glycosyaltion distribution by adjusting the concentration of asparagine. Without being bound by theory, it is thought that the effect of asparagine on glycosylation profile of an antibody is through its conversion to glutamine and/or aspartate. Asparagine is the amide donor for glutamine and can be converted to glutamine and/or aspartate (H Huang, Y Yu, X Yi, Y Zhang "Nitrogen metabolism of asparagine and glutamate in Vero cells studied by 1 H/15 N NMR spectroscopy" Applied microbiology and biotechnology 77 (2007) 427-436). Glutamine and aspartate are important intermediates in pyrimidine synthesis; and it is known that enhancing de novo pyrimidine biosynthesis could increase intracellular UTP concentration (Genentech, Inc. "Galacosylation of Recombinant Glycoproteins" US20030211573 (2003)). In addition, studies have suggested that glutamine and aspartate limitation is expected to inhibit amino sugar synthesis (G B Nyberg, R R Balcarcel, B D Follstad, G Stephanopoulos, DI Wang "Metabolic effects on recombinant interferon-gamma glycosylation in continuous culture of Chinese hamster ovary cells" Biotechnology and Bioengineering 62 (1999) 336-47; D C F Wong, K T K Wong, L T Gob, C K Heng, M G S. Yap "Impact of dynamic online fed-batch strategies on metabolism, is productivity and N-glycosylation quality in CHO cell cultures" Biotechnology and Bioengineering 89 (2005) 164-177). Both UTP and amino sugar are required for the synthesis of UDP-GlcNac, which is the substrate for protein glycosylation process. It is also possible that the effect of asparagine on glycosyaltion is via increasing ammonia concentration in the cell culture medium since it is showed that the addition of ammonia in CHO cultures could reduce the extent of glycosylation of synthesized EPO (M. Yang and M. Butler "Effect of Ammonia on the Glycosylation of Human Recombinant Erythropoietin in Culture" Biotechnol. Prog. 16 (2000) 751-759). We have found that ammonia concentration was increased after asparagine addition into the cell culture media.

In the studies summarized in Example 5, we investigated the effects on product quality attributes resulting from the addition of asparagine to hydrolysate based medium in an adalimumab-producing CHO cell line, generically named CHO cell line 141. Two experiments were performed in the instant Example. For the first experiment, glutamine and/or asparagine were added (at an individual concentration of 0.4 g/L) on day 6. For the second experiment, asparagine was added at different dosage (i.e. 0.4 g/L, 0.8 g/L or 1.6 g/L) either on day 0 (before inoculation) or together with the first glucose shot (happened on day 7).

5.1 Materials and Methods

The CHO cell line #11 was employed in the studies covered here. Upon thaw, cells were expanded in a 19-days seed train and then transferred into seed reactors for up to 7 days in growth medium. The cells were then brought to the laboratory and used in the small scale bioreactor experiments. The media used in these experiments contains basal media PFCHO (proprietary formulation), Bacto TC Yeastolate and Phytone Peptone.

Three litter Applikon bioreactors were sterilized and then charged with production medium. At inoculation, cells were aseptically transferred into each bioreactor to reach an initial cell density of $0.5 \times 10^6$ viable cells/mL. After inoculation, the bioreactors were set to the following conditions: pH=7.1, T=35° C., DO=30%, and agitation=200 rpm. The pH was shifted from 7.1 to 6.9 over the first 2.5 days and held at 6.9 for the remainder of the run. The percentage of dissolved oxygen was controlled by sparging a mixture of air and oxygen. The addition of 0.5 N NaOH or sparging of $CO_2$ maintained the pH. When the glucose concentration fell below 2 g/L, approximately 1.25% (v/v) of glucose solution (400 g/kg) was added to the cell culture.

For the first experiment, glutamine and/or asparagine were added (at an individual concentration of 0.4 g/L) together with the first glucose shot (happened on day 6). For the second experiment, asparagine was added at different dosage (i.e. 0.4 g/L, 0.8 g/L or 1.6 g/L) either on day 0 (before inoculation) or together with the first glucose shot (happened on day 7).

Samples were taken daily from each reactor to monitor growth. The following equipment was used to analyze the samples: Cedex cell counter for cell density and viability; Radiometer ABL 5 blood gas analyzer for pH, pCO2 and pO2; YSI 7100 analyzer for glucose and lactate concentration. Some of the daily samples and the harvest samples were centrifuged at 3,000 RPM for 30 min and then the supernatants were stored at −80° C. Later, the thawed harvest samples were filtered through a 0.2 μm filter, purified by Protein A chromatography, and then oligosaccharide analysis was performed and then oligosaccharide analysis was performed as described in Example 1.

5.2 Culture Growth and Productivity

Figure 13A:
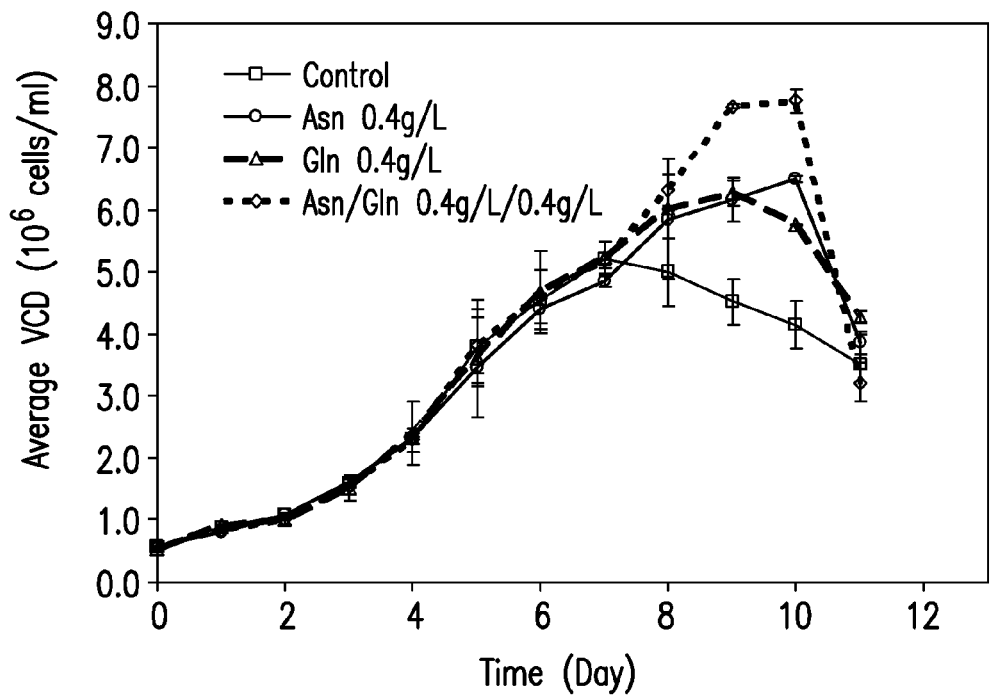
FIG. 13 depicts the effect of supplementation of asparagine and/or glutamine on day 6 to hydrolysate based media in CHO cell line #1 on culture growth (a), culture viability (b) and product titer (c).
Figure 15A:
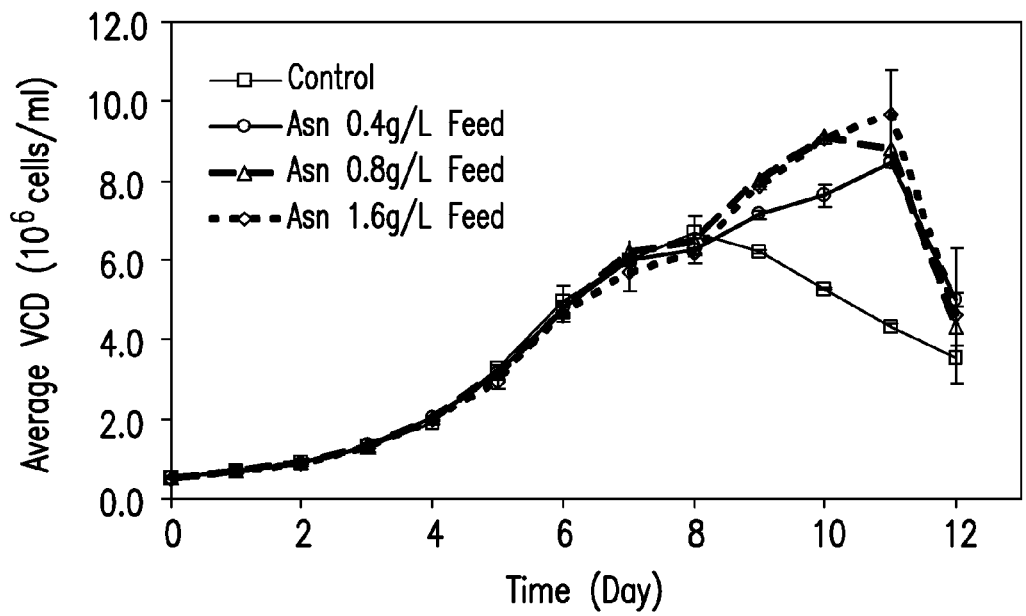
FIG. 15 depicts the dose dependent effect of supplementation of asparagine on Day 7 to hydrolysate based media in adalimumab-producing CHO cell line #1 on culture growth (a) and culture viability (b) and product titer (c).
Figure 17A:
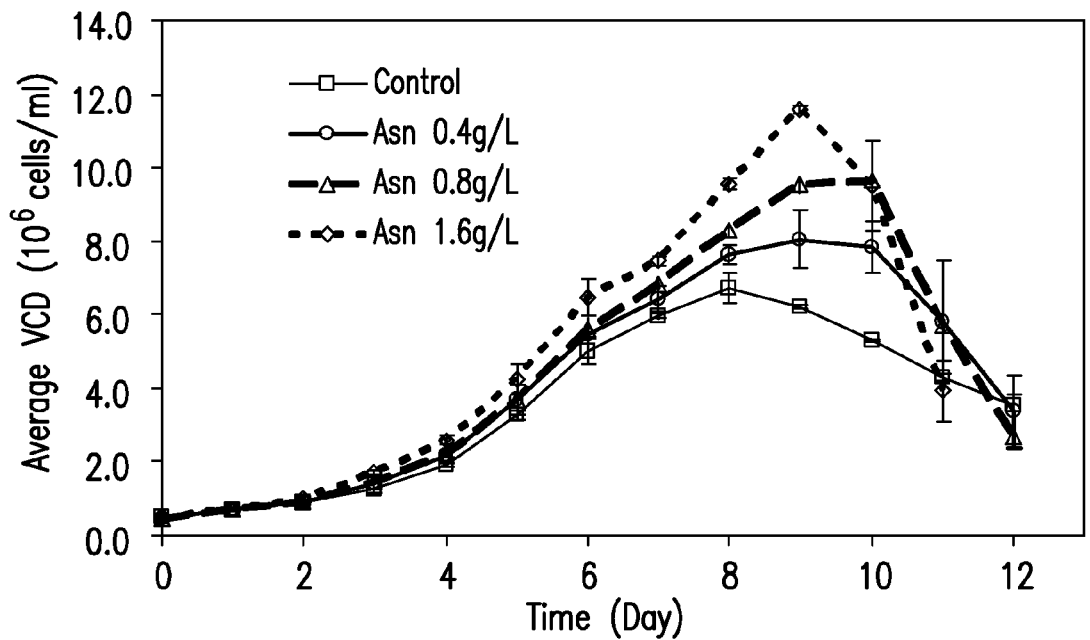
FIG. 17 depicts the dose dependent effect of supplementation of asparagine on Day 0 to hydrolysate based media in adalimumab-producing CHO cell line #1 on culture growth (a) and culture viability (b) and product titer (c).

In both of the experiments performed in 3 L bioreactor in hydrolysate based media with CHO cell line #1 described in the instant Example, the addition of glutamine and/or asparagine together with a glucose shot increased the maximum cell density (FIGS. 13A and 15A, respectively). The increase in cell density is started two days after the addition in both cases. Maximum viable cell density was consistent when 0.4 g/L of glutamine or asparagine was added. Increasing the concentration of asparagine to 0.8 g/L or adding both glutamine and asparagine at a concentration of 0.4 g/L each further increased the maximum viable cell density; however, adding asparagine at a higher concentration than 0.8 g/L (e.g., 1.6 g/L) did not continue to increase the maximum viable cell density. In contrast, when asparagine was added on day 0 (before inoculation), the maximum viable cell density increased in a dose dependent manner, with the maximum viable cell density being reached when 1.6 g/L of asparagine was added on day 0 (FIG. 17A).

Figure 13B:
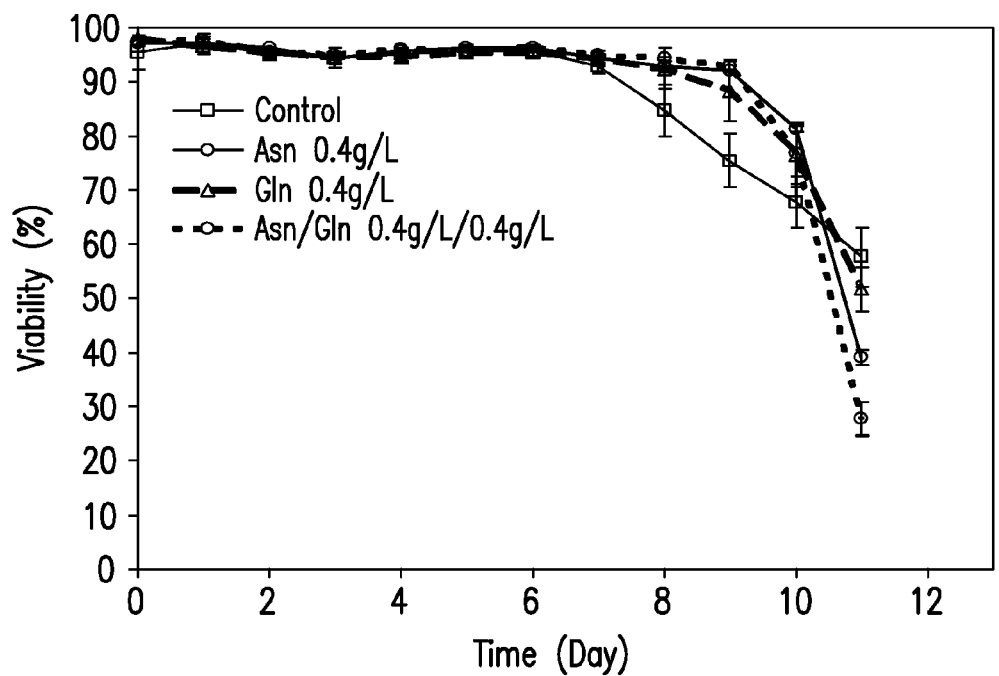
Figure 13C:
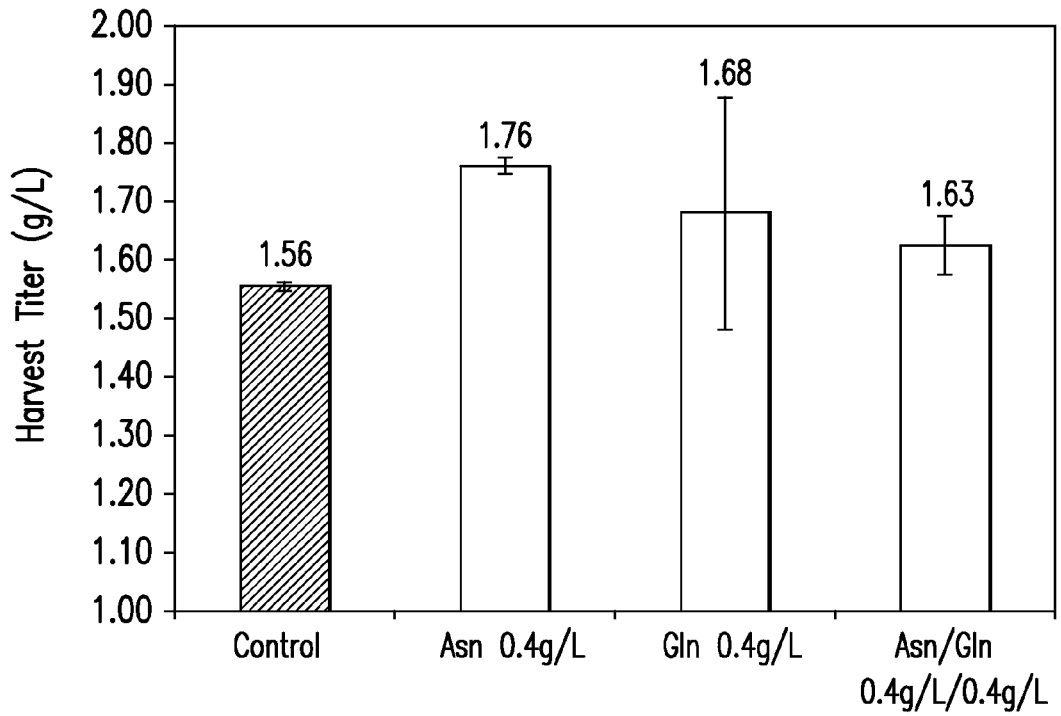
Figure 14A:
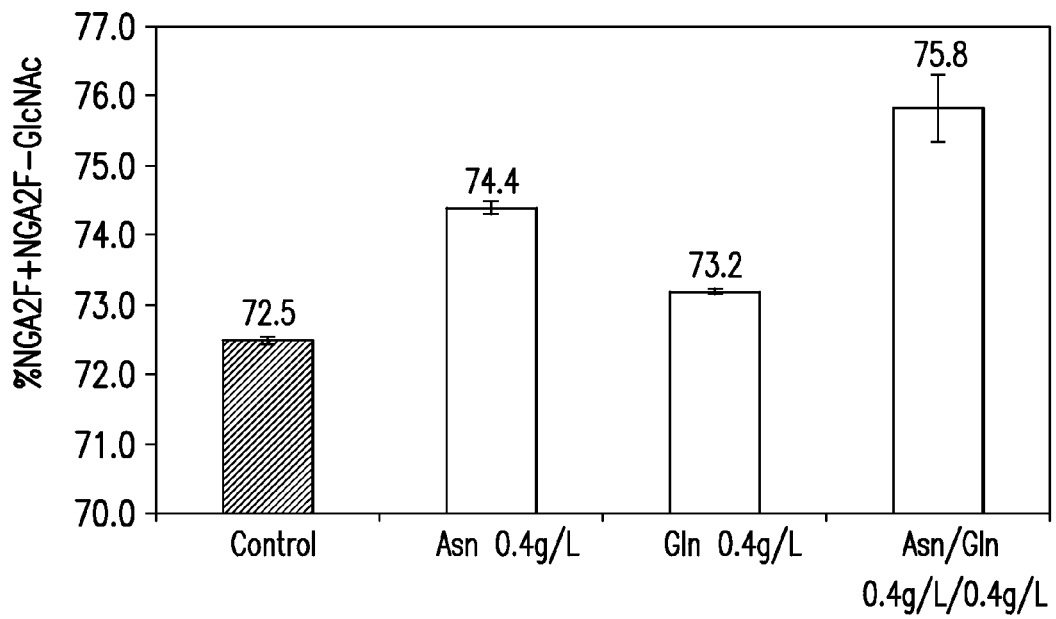
FIG. 14 depicts the effect of supplementation of asparagine and/or glutamine on Day 6 to hydrolysate based media in adalimumab-producing CHO cell line #1 on NGA2F and NGA2F-GlcNac glycans (a) and on NA1F and NA2F glycans (b).
Figure 14B:
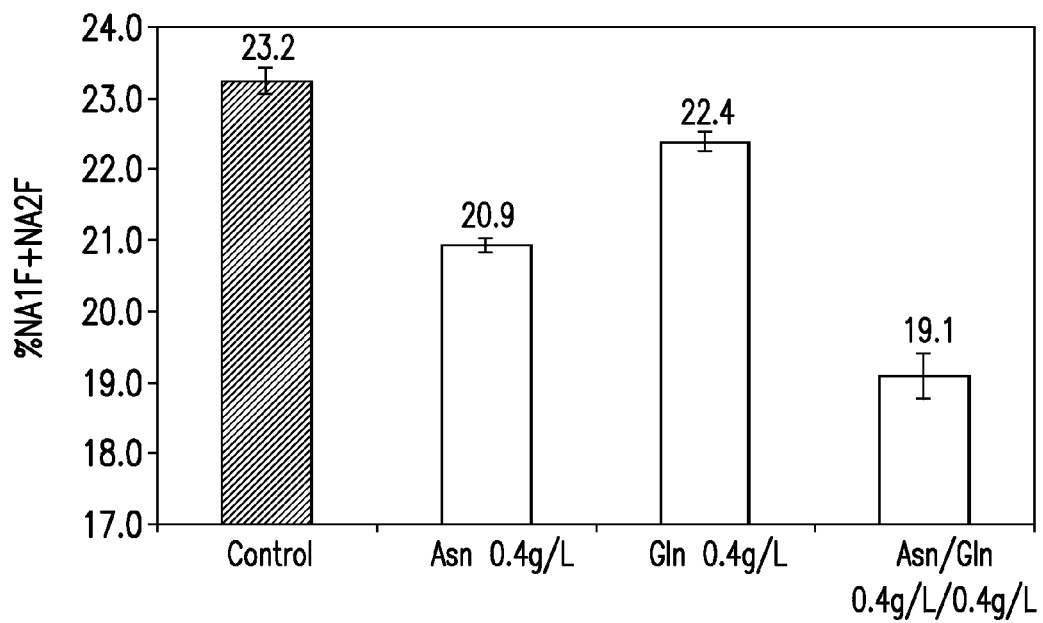
Figure 15B:
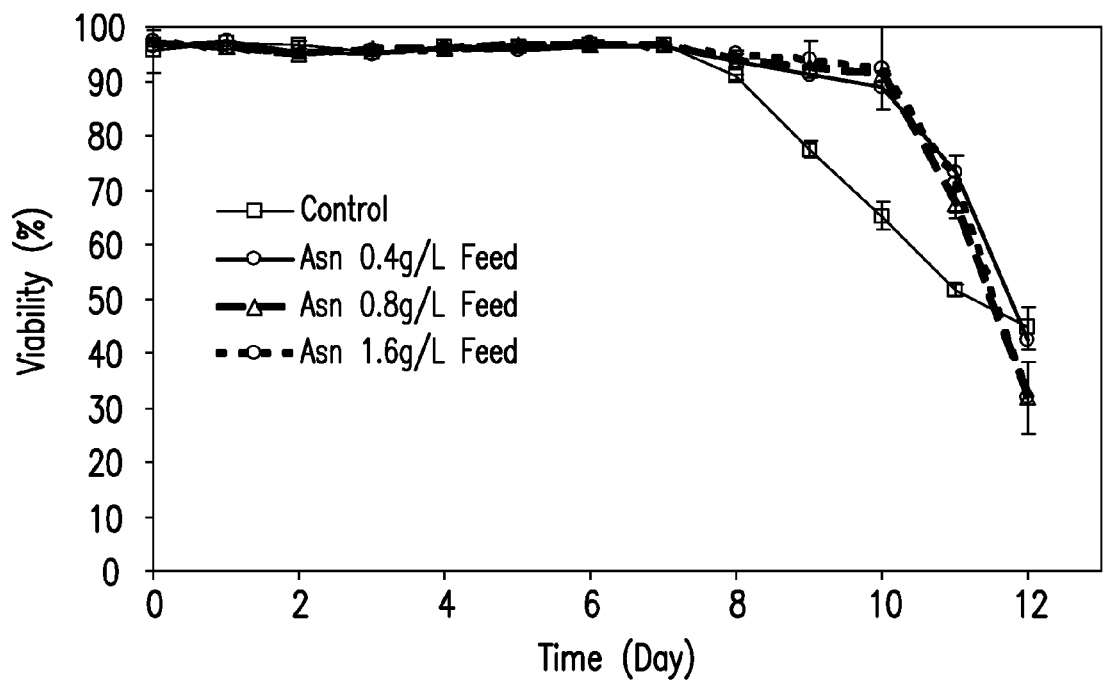
Figure 15C:
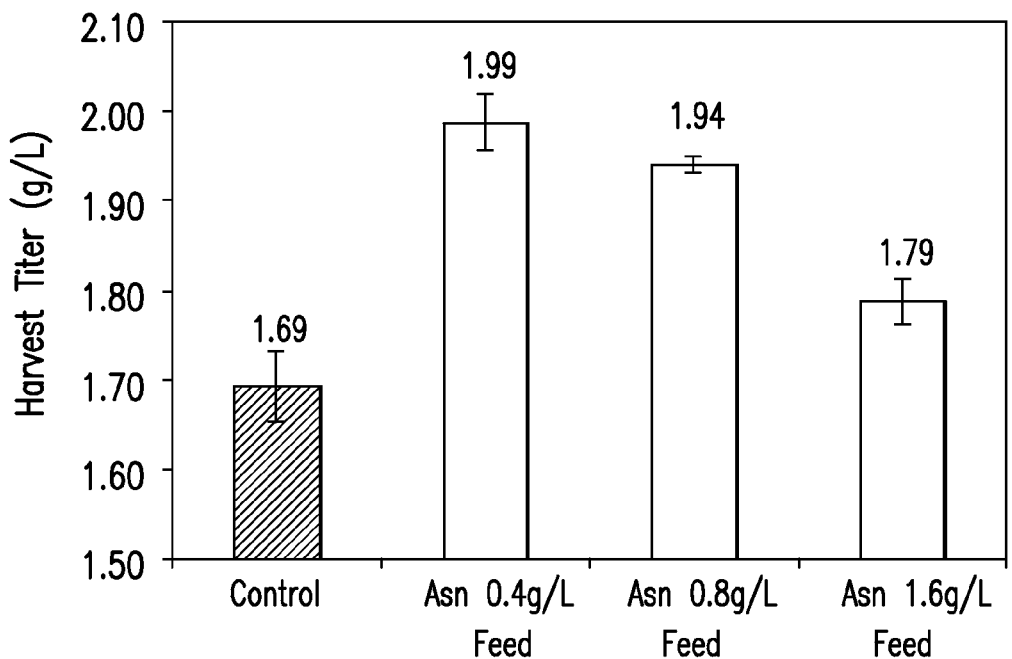
Figure 16A:
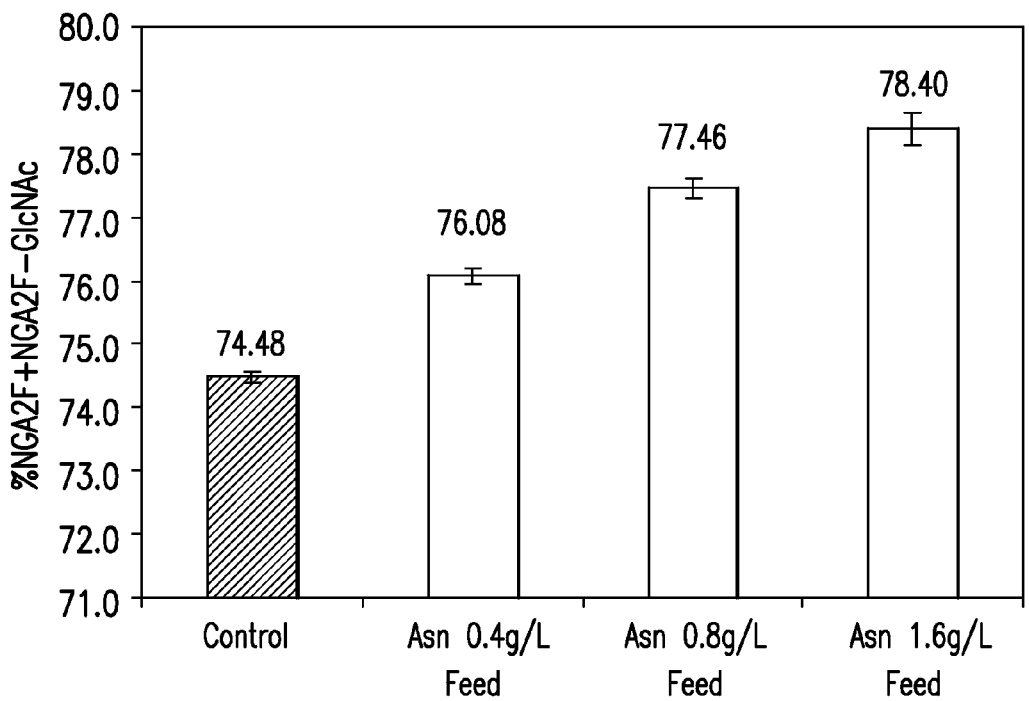
FIG. 16 depicts the dose dependent effect of supplementation of asparagine on Day 7 to hydrolysate based media in adalimumab-producing CHO cell line #1 on NGA2F and NGA2F-GlcNac glycans (a) and on NA1F and NA2F glycans (b).
Figure 16B:
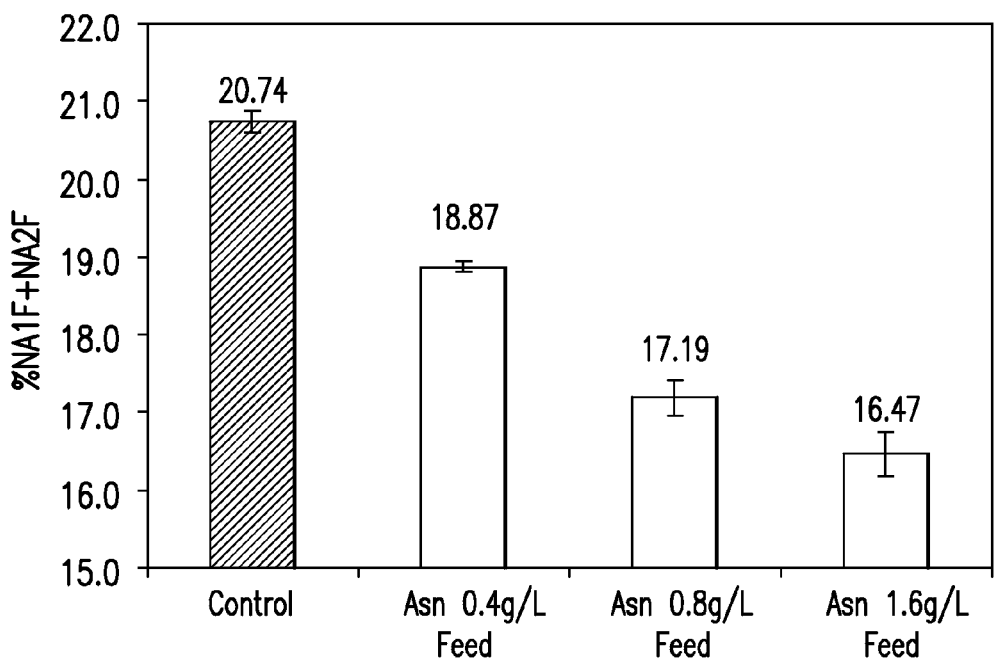
Figure 17B:
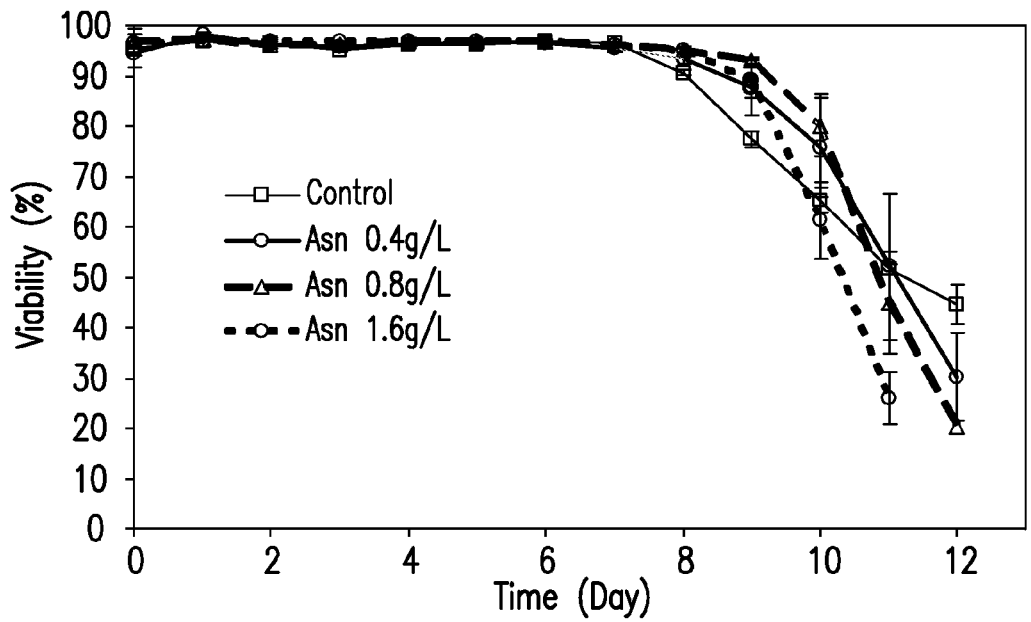
Figure 17C:
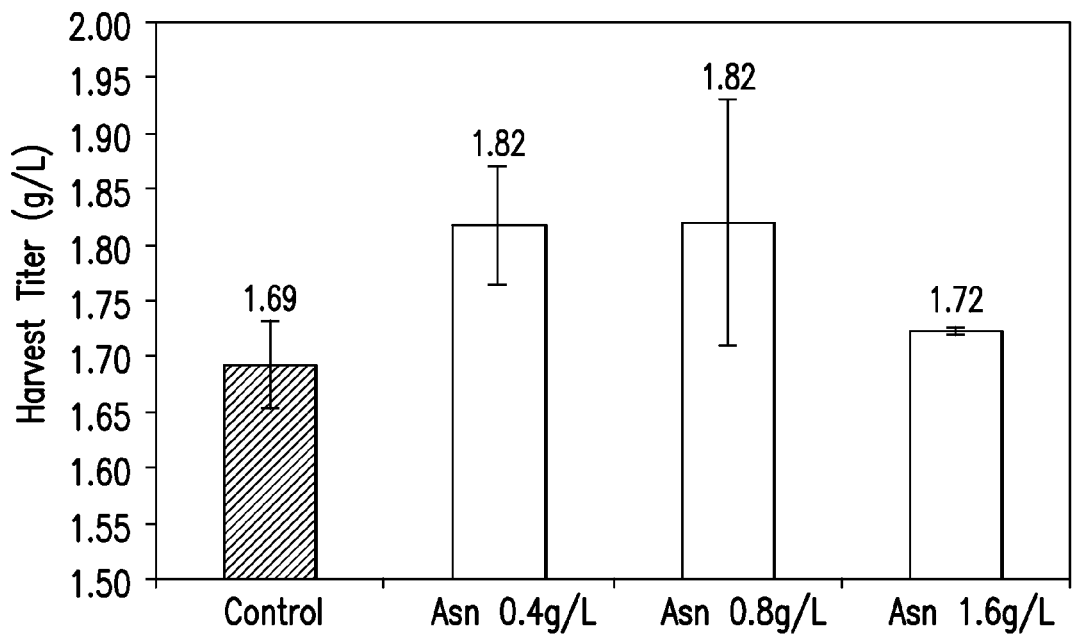
Figure 18A:
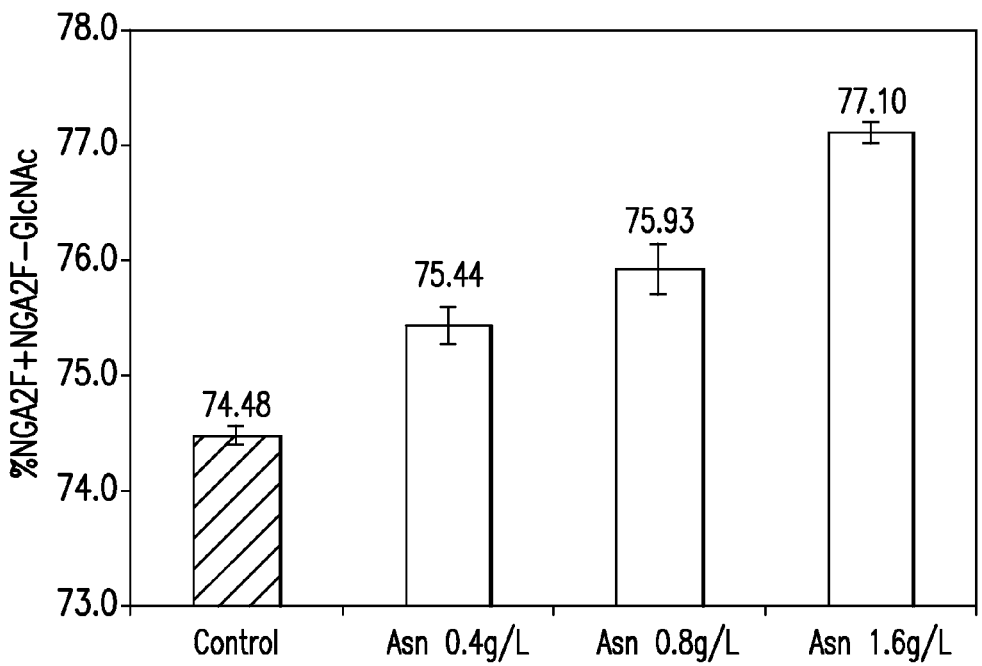
FIG. 18 depicts the dose dependent effect of supplementation of asparagine on Day 0 to hydrolysate based media in adalimumab-producing CHO cell line #1 on NGA2F and NGA2F-GlcNac glycans (a) and on NA1F and NA2F glycans (b).
Figure 18B:
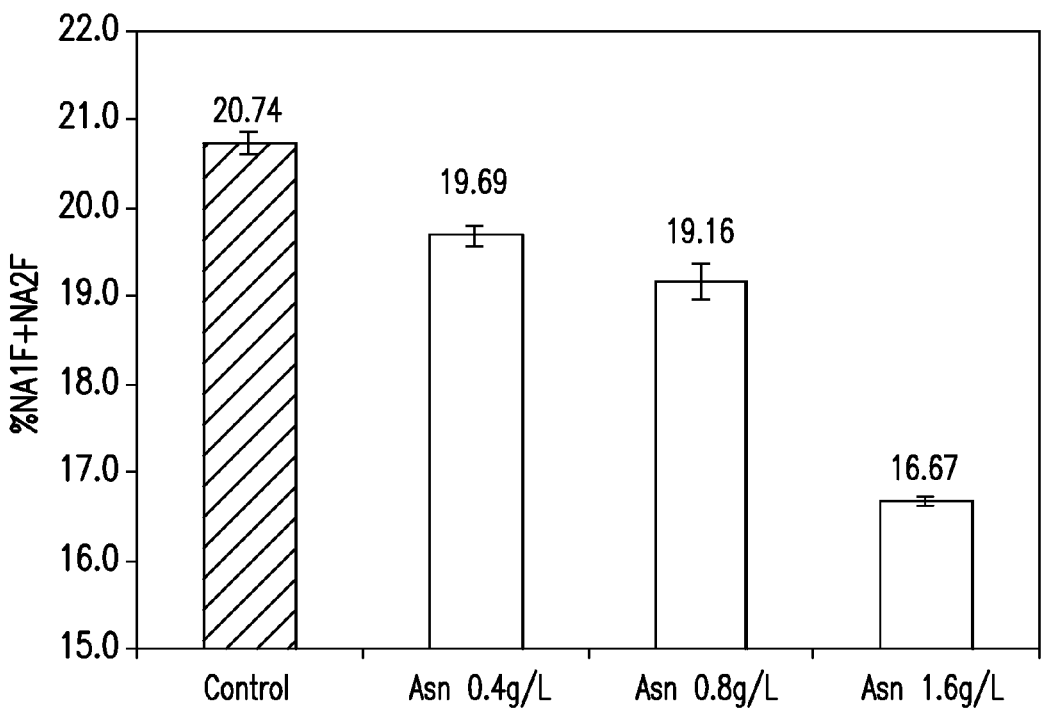

A drop in viability was delayed, as compared to control cultures, in both experiments described in the instant Example for approximately 3 days when glutamine and/or asparagine was added on day 6 or 7 (FIGS. 13B and 15B, respectively). However, the drop in viability accelerated on the last day of the cultures. In contrast, although the drop in viability was delayed when asparagine was added on day 0, the effect of delaying viability decay was not as efficient as when the amino acids were added later (e.g., on day 6 or day 7) as shown in FIG. 17B.

5.3 Oligosaccharide Analysis

The experiments described in the instant Example indicate that oligosaccharide distribution is altered with the addition of asparagine and/or glutamine. The addition of asparagine increased NGA2F+NGA2F-GlcNac in a dose dependent manner. Compared to control, the percentage of NGA2F+NGA2F-GlcNac was increased by 1.0-3.9% and the percentage of NGA2F+NGA2F was decreased by 1.1-4.3% when 0.4 to 1.6 g/L asparagine was added on either day 0 or days 6 or 7 (FIGS. 14A-14B, 16A-16B and 18A-18B). Addition of 0.4 g/L glutamine increased the percentage of NGA2F+NGA2F-GlcNac by 0.7% and lowered the percentage of NA1F+NA2F by 0.9%. Adding both asparagine and glutamine (0.4 g/L of each) increased the percentage of NGA2F+NGA2F-GlcNAc by 3.3% and decreased the percentage of NA1F+NA2F by 4.2%. In addition, the cell growth profile is the same when 0.8 and 1.6 g/L of asparagine was added on day 7 (FIGS. 15A and 15B), but a dose dependent effect on oligosaccharide distribution was observed (FIGS. 16A and 16B), indicating that the effect on oligosaccharide distribution was due to the addition of asparagine and not the increased maximum viable cell density or delayed drop in viability.

Example 6

Yeast, Soy, or Wheat Hydrolysate Addition to Commercially Available CD Media IS CHO-CD for Culture of an Adalimumab-Producing CHO Cell Line #1

In the study summarized in this example, the effects on glycosylation resulting from the addition of yeast, soy or wheat hydrolysates to CD media IS CHO-CD (Irvine Scientific) in the adalimumab-producing CHO cell line #1 utilized in Example 1 were evaluated.

6.1 Materials and Methods

Adaptation and production media (Irvine Scientific IS CHO-CD 91119) were supplemented with Bacto TC Yeastolate, BBL Phytone Peptone, or Wheat Peptone E1 according to the experimental design in FIG. 42. The control cultures were not supplemented with hydrolysates. All media pH was adjusted to approximately 7.1.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning vented non-baffled shake flasks at an initial VCD of approximately $0.5 \times 10^6$ cells/mL. The shake flask study was run in an extended-batch mode by feeding a glucose solution (1.25% (v/v) of 40% solution) when the media glucose concentration fell below 3 g/L.

6.2 Culture Growth and Productivity

Figure 19A:
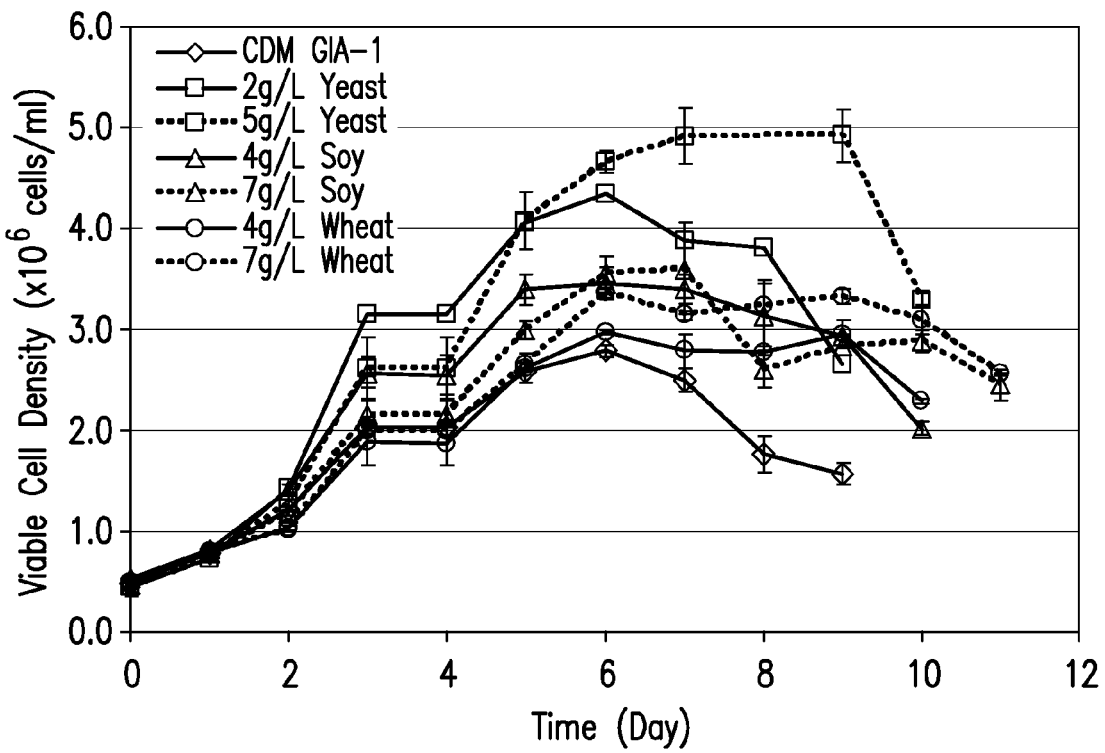
FIG. 19 depicts the effect of yeast, soy, or wheat hydrolysate addition to CDM Irvine IS CHO-CD in adalimumab-producing CHO cell line #1 on (a) Culture growth, (b) Culture viability, and (c) Harvest titer.
Figure 19B:
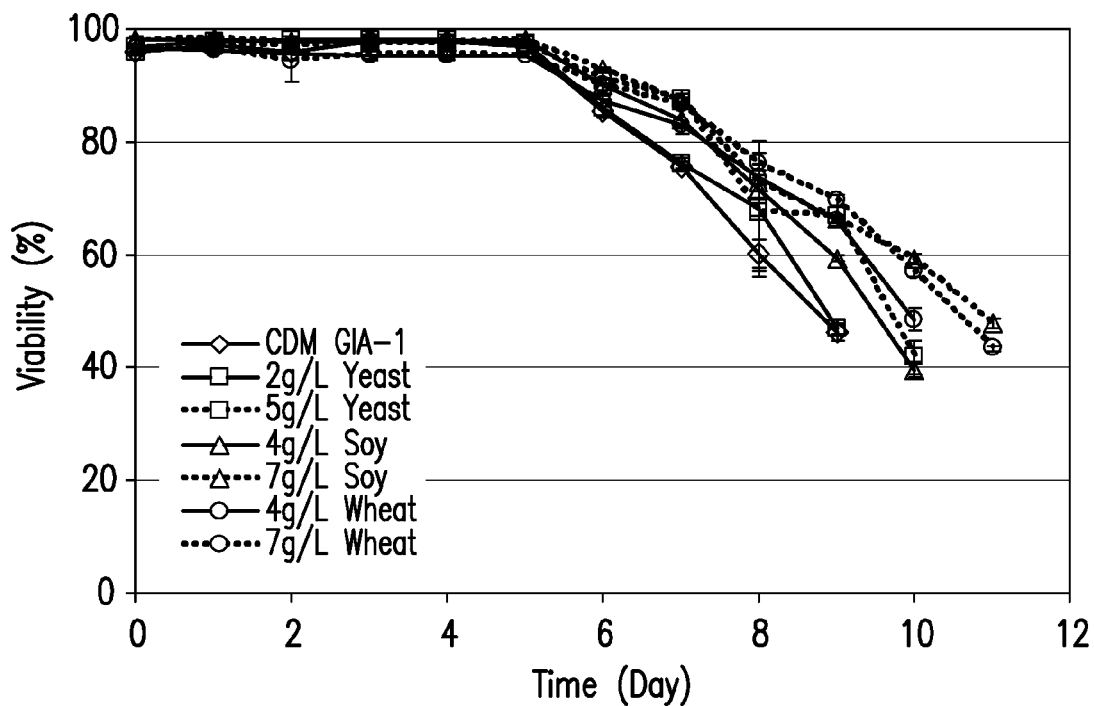
Figure 19C:
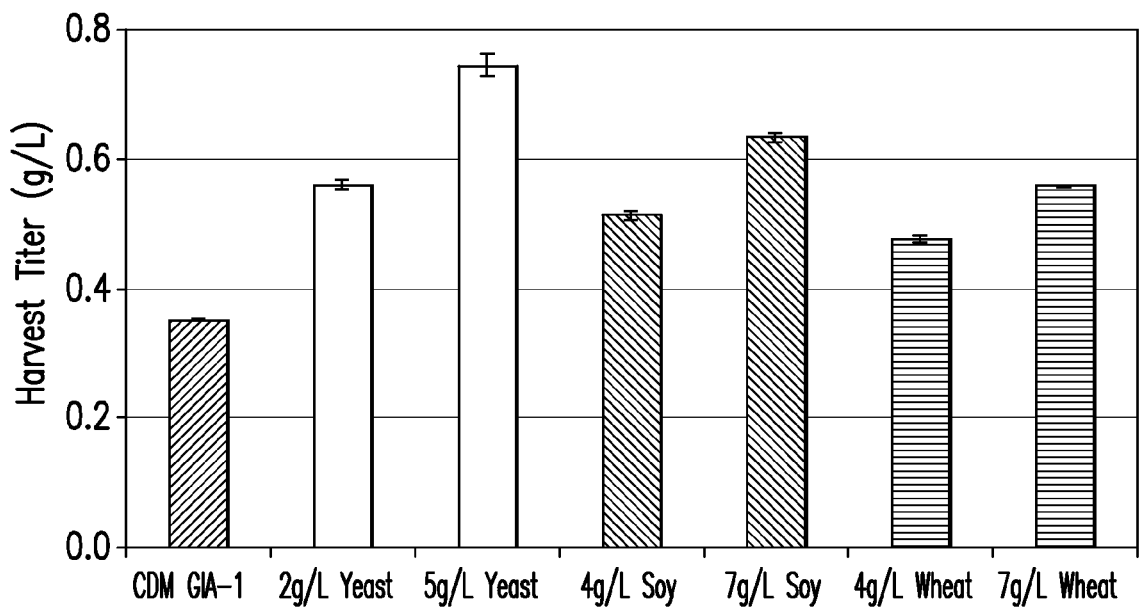

Addition of yeast, soy or wheat hydrolysates to Irvine IS CHO-CD media increased the maximum VCD and culture length for most conditions studied compared to the control (FIG. 19A). The largest increase in maximum VCD was recorded for cultures supplemented with 5 g/L Bacto TC Yeastolate. A concentration-dependent increase in harvest titer was observed for all cultures supplemented with hydrolysates (FIG. 19C).

6.3 Oligosaccharide Analysis

Figure 20A:
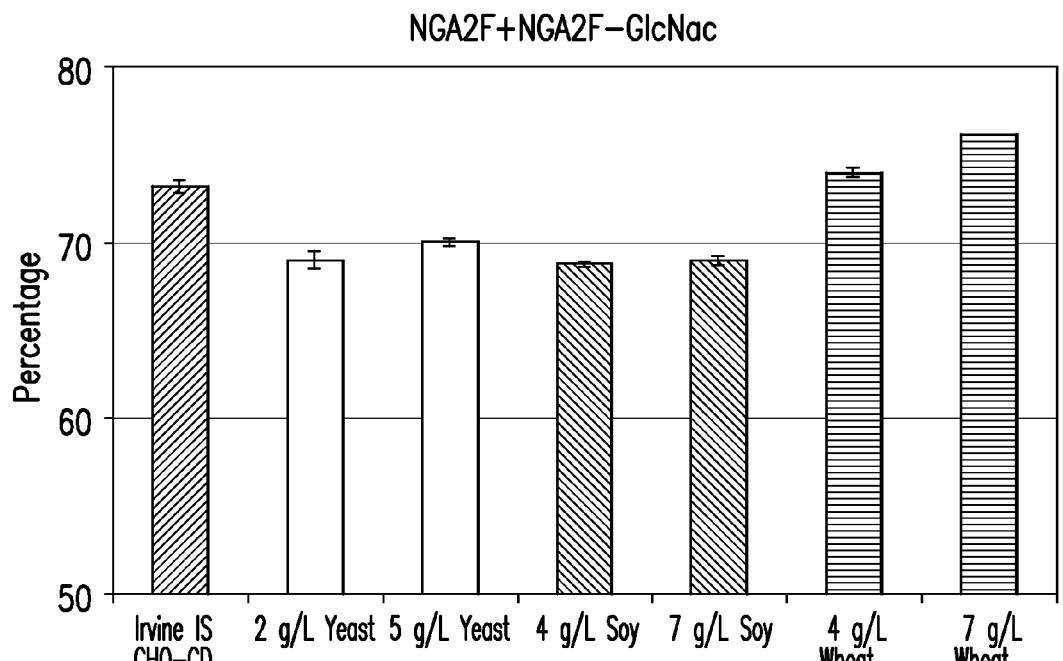
FIG. 20 depicts the effect of yeast, soy, or wheat hydrolysates addition to CDM Irvine IS CHO-CD in adalimumab-producing CHO cell line #1 on oligosaccharides profile (a) NGA2F+NGA2F-GlcNac and (b) NA1F+NA2F.
Figure 20B:
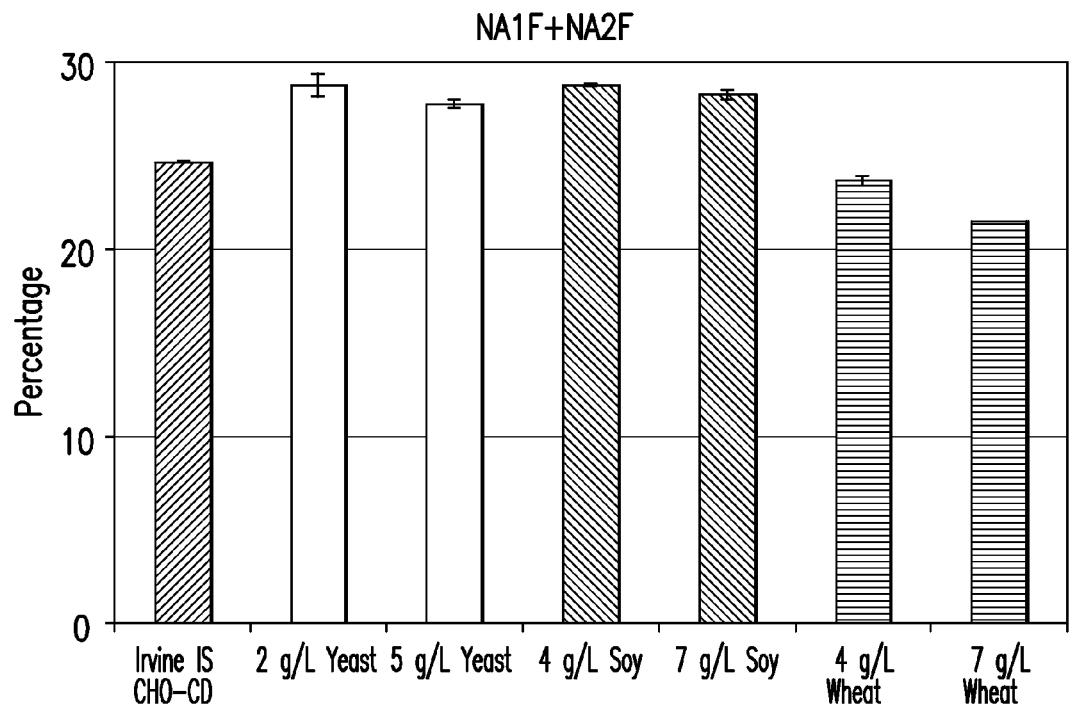

Supplementation of Irvine IS CHO-CD media with yeast hydrolysates decreased the percentage of NGA2F+NGA2F-GlcNac glycans by 3-4%, and increased the percentage of NA1F+NA2F glycans by the same percentage compared to control (NGA2F+NGA2F-GlcNac: 73%; NA1F+NA2F: 25%) (FIGS. 20A-B). Addition of soy hydrolysates to Irvine IS CHO-CD media decreased the percentage of NGA2F+NGA2F-GlcNac glycans by 4%, and increased the percentage of NA1F+NA2F glycans by the same percentage compared to control. However, addition of wheat hydrolysates to Irvine IS CHO-CD media resulted in an opposite trend. A concentration-dependent increase in the percentage of NGA2F+NGA2F-GlcNac glycans by 1-3% and a corresponding decrease in the percentage of NA1F+NA2F glycans was observed.

Example 7

Yeast, Soy, or Wheat Hydrolysate Addition to CD Media GIA-1 for Culture of an Adalimumab-Producing CHO Cell Line #2

In the study summarized in this example, the effects on glycosylation resulting from the addition of yeast, soy or wheat hydrolysates to CD media GIA-1 in an adalimumab-producing CHO cell line, generically named CHO cell line #2 were evaluated.

7.1 Materials and Methods

Adaptation and production media were supplemented with Bacto TC Yeastolate, BBL Phytone Peptone, or Wheat Peptone E1 according to the experimental design in FIG. 43. The control cultures were not supplemented with hydrolysates. All media pH was adjusted to approximately 7.1 and the media osmolality was adjusted to 290-300 mOsmol/kg.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 180 RPM in a 35° C., 5% $CO_2$ dry incubator. Production cultures were initiated in duplicate 500 mL (200 mL working volume) Corning vented non-baffled shake flasks at an initial VCD of approximately $0.5 \times 10^6$ cells/mL. The shake flask study was run in an extended-batch mode by feeding a glucose solution (1.25% (v/v) of 40% solution) when the media glucose concentration fell below 3 g/L.

7.2 Culture Growth and Productivity

Figure 21A:
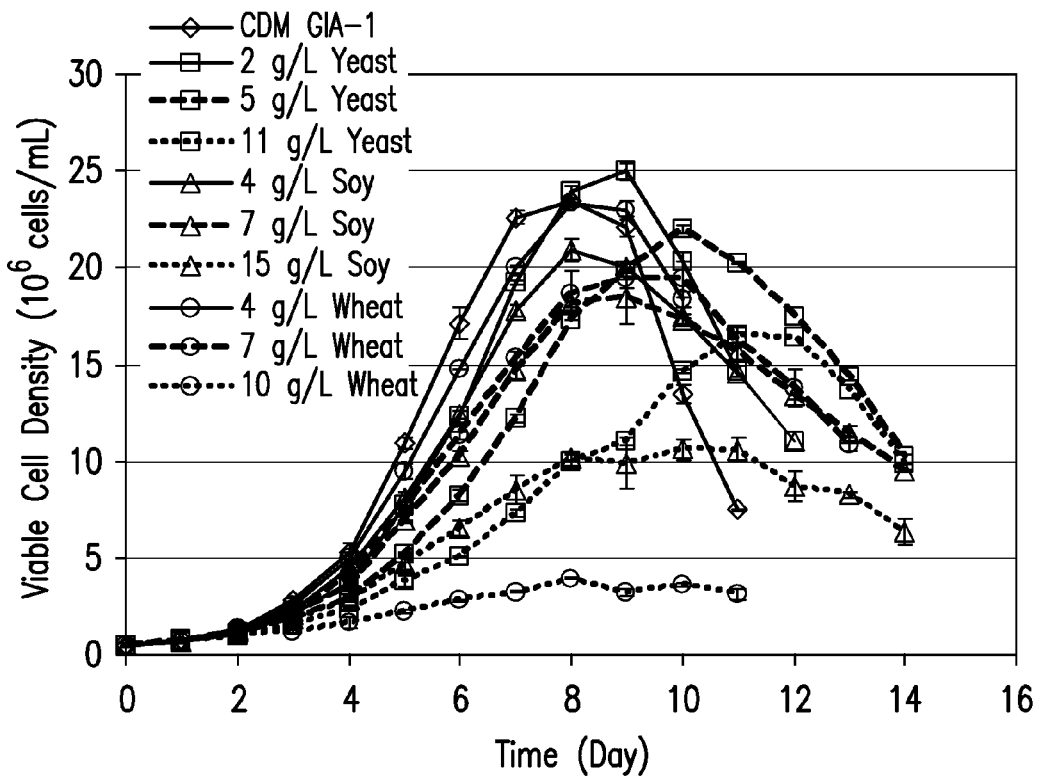
FIG. 21 depicts the effect of yeast, soy, or wheat hydrolysate addition to CDM GIA-1 in adalimumab-producing CHO cell line #2 on (a) Culture growth, (b) Culture viability, and (c) Harvest titer.
Figure 21B:
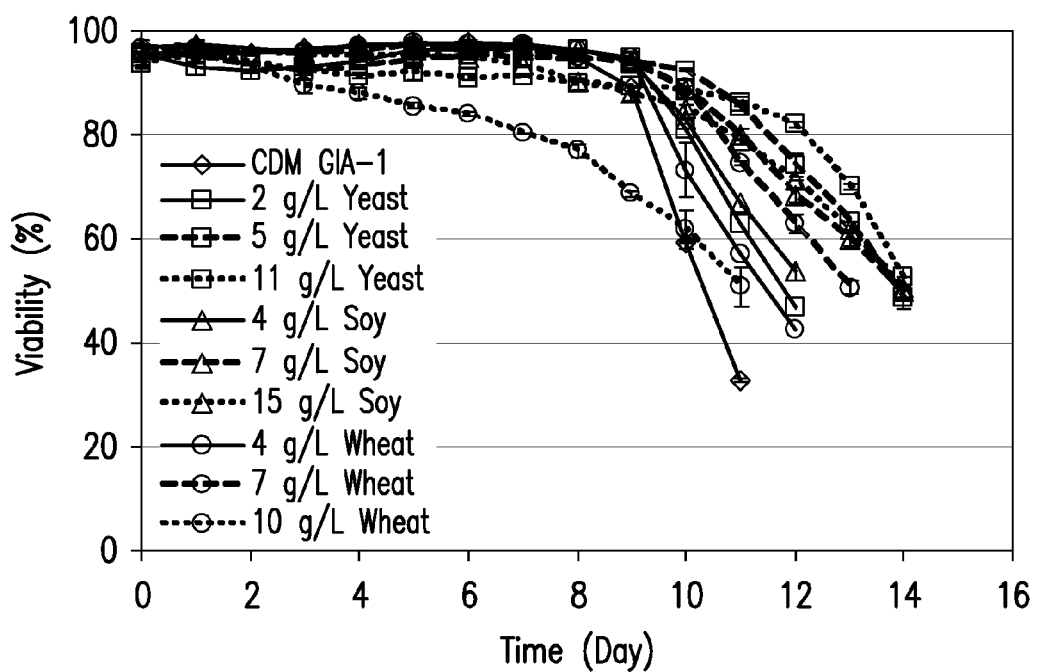
Figure 21C:
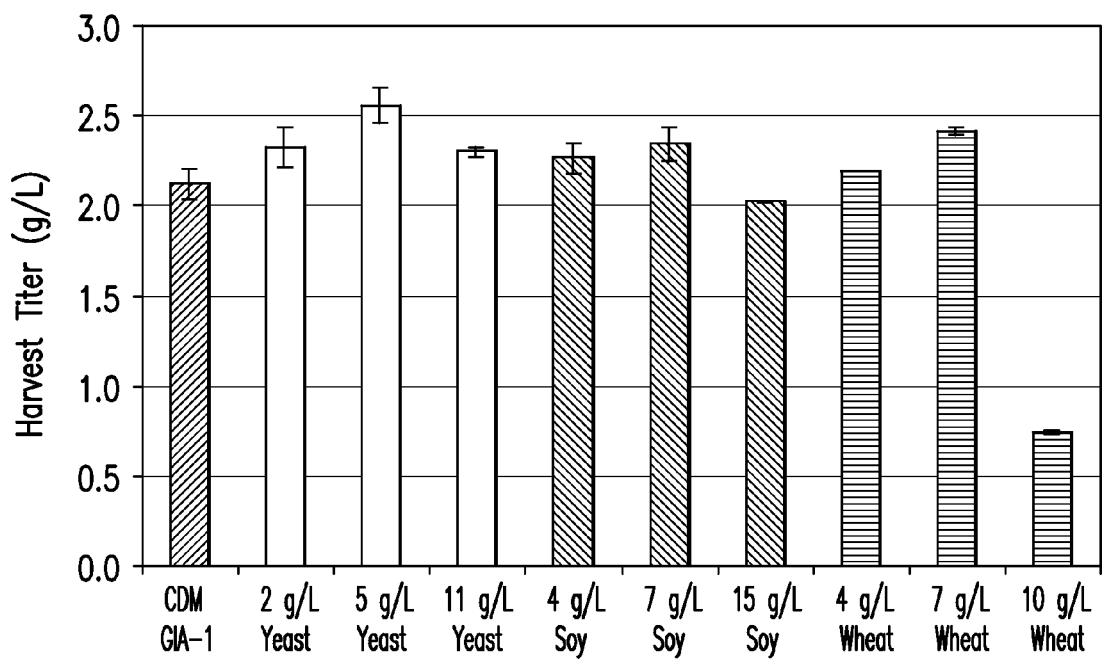

Supplementation of yeast, soy or wheat hydrolysates to CD media GIA-1 extended the culture length by 1 to 3 days and decreased the maximum VCD in a dose-dependent manner (FIGS. 21A-B). The addition of these hydrolysates at the highest concentrations significantly decreased maximum VCD, with wheat hydrolysates added at 10 g/L showing the most severe growth inhibition effects. However, an impact on harvest titer was only observed for the culture supplemented with 10 g/L wheat hydrolysates (65% reduction). An increase in the harvest titer compared to the control (FIG. 21C) was found in most other cultures.

7.3 Oligosaccharide Analysis

Figure 22A:
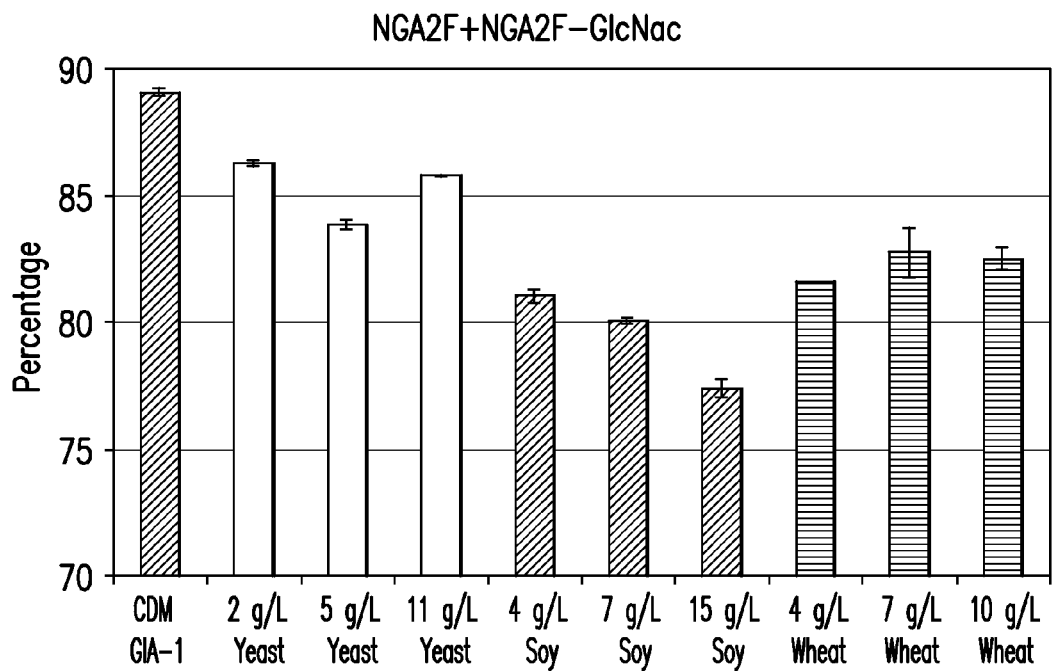
FIG. 22 depicts the effect of yeast, soy, or wheat hydrolysate addition to CDM GIA-1 in adalimumab-producing CHO cell line #2 on (a) NGA2F+NGA2F-GlcNac and (b) NA1F+NA2F.
Figure 22B:
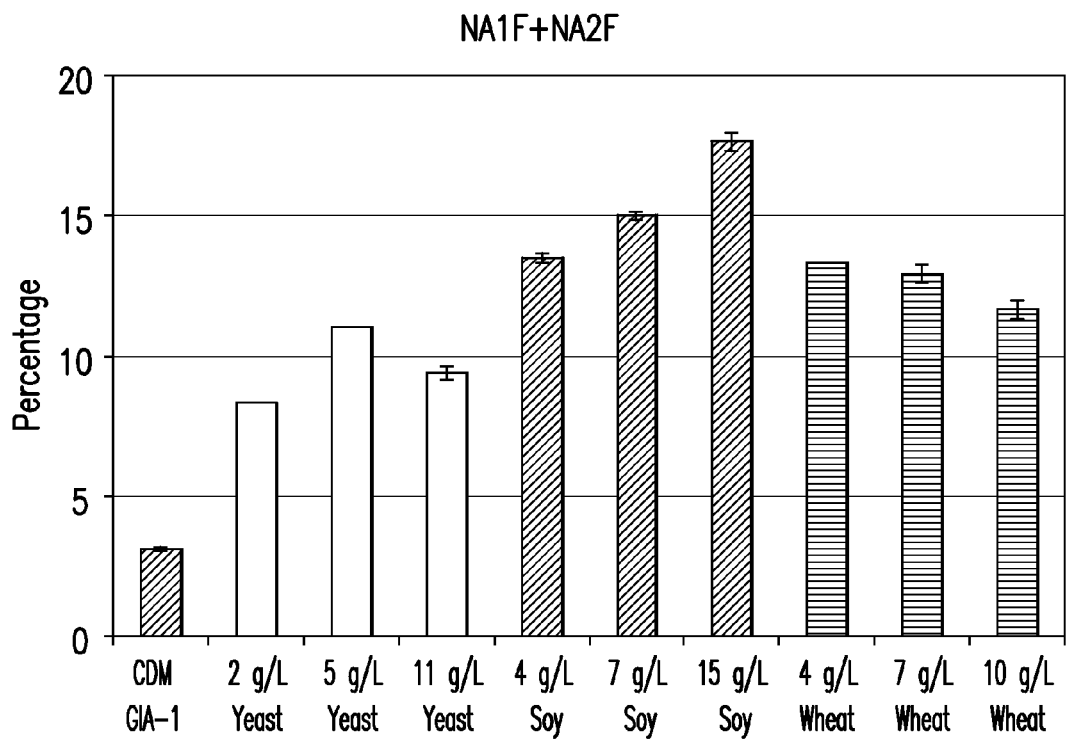

Addition of yeast hydrolysates decreased the percentage of NGA2F+NGA2F-GlcNac glycans by 3-5%, and increased the percentage of NA1F+NA2F glycans by 5-8% compared to control (NGA2F+NGA2F-GlcNac: 89%; NA1F+NA2F: 3%) (FIGS. 22A-B). Addition of soy hydrolysates to CD media GIA-1 decreased the NGA2F+NGA2F-GlcNac glycans by 8-12%, and increased the NA1F+NA2F glycans by 10-15% compared to control. Addition of wheat hydrolysates decreased the NGA2F+NGA2F-GlcNac glycans by 6-7%, and increased the NA1F+NA2F glycans by 9-10% compared to control.

Example 8

Yeast, Soy, or Wheat Hydrolysate Addition to CD Media GIA-1 for Culture of an Adalimumab-Producing CHO Cell Line #3

In the study summarized in this example, the effects on glycosylation resulting from the addition of yeast, soy or wheat hydrolysates to CD media GIA-1 in an adalimumab-producing CHO cell line, generically named CHO cell line #3 were evaluated.

8.1 Materials and Methods

Adaptation and production media were supplemented with Bacto TC Yeastolate, BBL Phytone Peptone, or Wheat Peptone E1 according to the experimental design in FIG. 44. The control cultures were not supplemented with hydrolysates. All media pH was adjusted to approximately 7.1 and the media osmolality was adjusted to 290-300 mOsmol/kg.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 140 RPM in a 36° C., 5% $CO_2$ dry incubator. Production cultures were initiated in duplicate 500 mL (200 mL working volume) Corning vented non-baffled shake flasks at an initial VCD of approximately $0.5 \times 10^6$ cells/mL. The shake flask study was run in an extended-batch mode by feeding a glucose solution (1.25% (v/v) of 40% solution) when the media glucose concentration fell below 3 g/L.

8.2 Culture Growth and Productivity

Figure 23A:
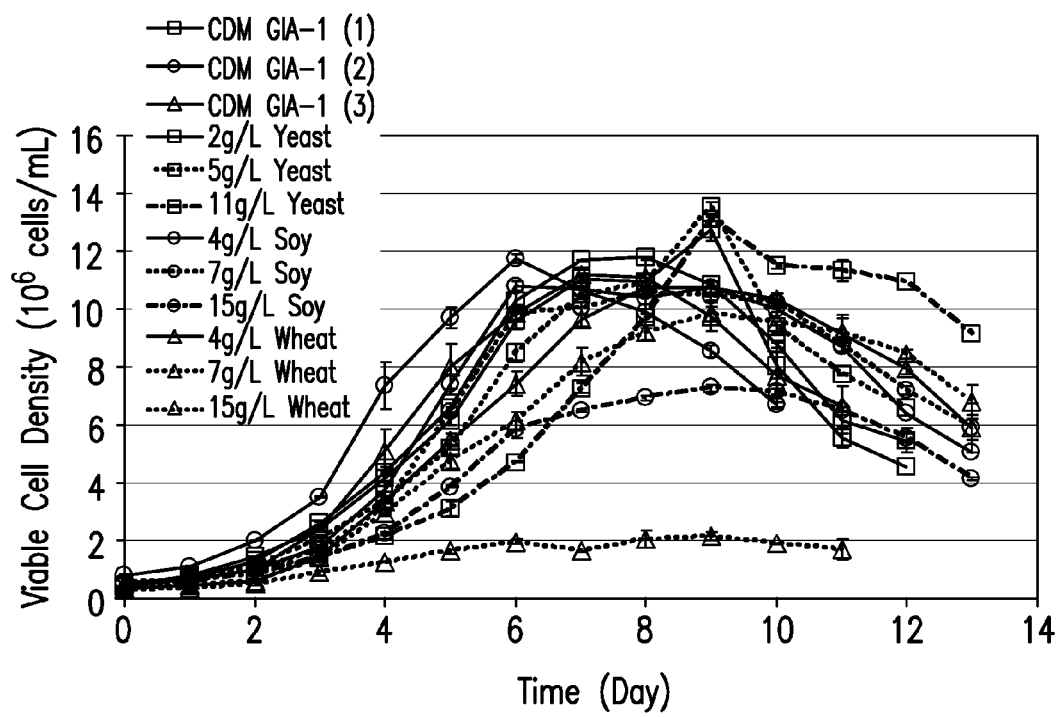
FIG. 23 depicts the effect of yeast, soy, or wheat hydrolysate addition to CDM GIA-1 in adalimumab-producing CHO cell line #3 on (a) Culture growth, (b) Culture viability, and (c) Harvest titer.
Figure 23B:
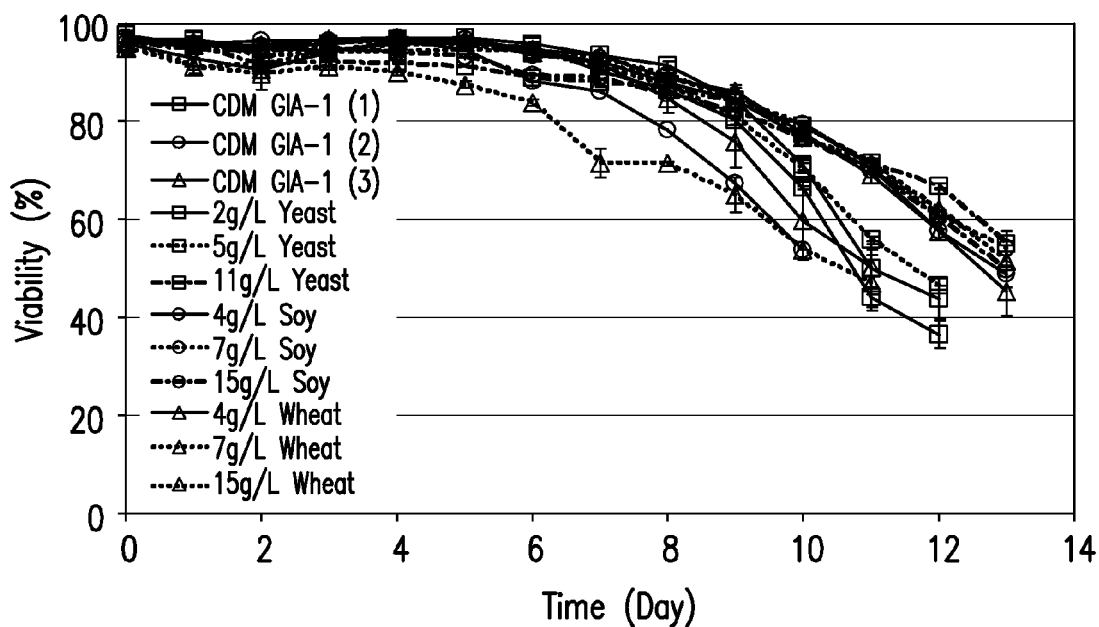
Figure 23C:
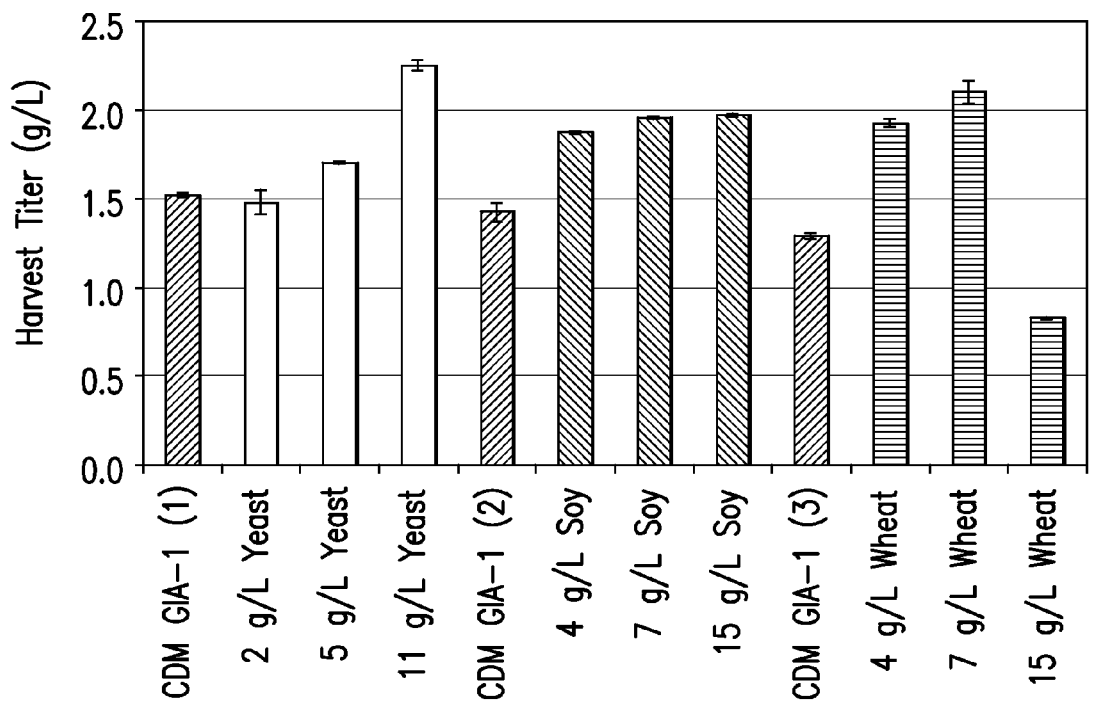

Supplementation of production CD media with high concentrations of hydrolysates—11 g/L yeast, 15 g/L soy or 15 g/L wheat hydrolysates, decreased the culture growth rate and increased the culture length compared to the control (FIGS. 23A-B). Harvest titer increased with increasing hydrolysate concentrations in the production media, except for the condition supplemented with 15 g/L wheat hydrolysates, which experienced significant growth inhibition and harvest titer decrease compared to control (FIG. 23C).

8.3 Oligosaccharide Analysis

Supplementation of CD media GIA-1 with yeast, soy or wheat hydrolysates decreased the percentage of NGA2F+NGA2F-GlcNac glycans and increased the percentage of NA1F+NA2F glycans in a dose-dependent manner (FIGS. 24A-B). Addition of yeast hydrolysates decreased the percentage of NGA2F+NGA2F-GlcNac glycans by 5-12%, and increased the percentage of NA1F+NA2F glycans by 3-11% compared to control (NGA2F+NGA2F-GlcNac: 91%; NA1F+NA2F: 6%). Addition of soy hydrolysates to CD media GIA-1 decreased the NGA2F+FGA2F-GlcNac glycans by 13-25%, and increased the NA1F+NA2F glycans by 13-25% compared to control. Addition of wheat hydrolysates decreased the NGA2F+NGA2F-GlcNac glycans by 12-18%, and increased the NA1F+NA2F glycans by 12-18% compared to control.

Example 9

Yeast, Soy, or Wheat Hydrolysate Addition to CD Media GIA-1 for Culture of a CHO Cell Line Producing mAb #1

In the studies summarized in this example, the effects on glycosylation resulting from the addition of yeast, soy or wheat hydrolysates to CD media GIA-1 in a CHO cell line producing mAb #1 were evaluated.

9.1 Materials and Methods

Adaptation and production media were supplemented with Bacto TC Yeastolate (BD Biosciences; catalog #255772), BBL Phytone Peptone (BD Biosciences; catalog #211096), or Wheat Peptone E1 (Organotechnie; catalog #19559) according to the experimental design in FIG. 45. The control cultures were not supplemented with hydrolysates. All media pH was adjusted to approximately 7.2 and the media osmolality was adjusted to 290-330 mOsmol/kg.

Cultures were expanded for 4 passages (3 days each) in their respective adaptation media in a combination of 250 mL (50 mL or 100 mL working volume) and 500 mL (150 mL working volume) Corning vented non-baffled shake flasks and maintained on an Infors Multitron orbital shaker at 140 RPM in a 36° C., 5% $CO_2$ incubator. Production cultures were initiated in duplicate 500 mL (200 mL working volume) Corning vented non-baffled shake flasks at approximately $1.0 \times 10^6$ cells/mL initial VCD. The study was run in an extended-batch mode by feeding a glucose solution (1.0% (v/v) of 40% solution) when the media glucose concentration fell below 3 g/L.

9.2 Culture Growth and Productivity

Figure 25A:
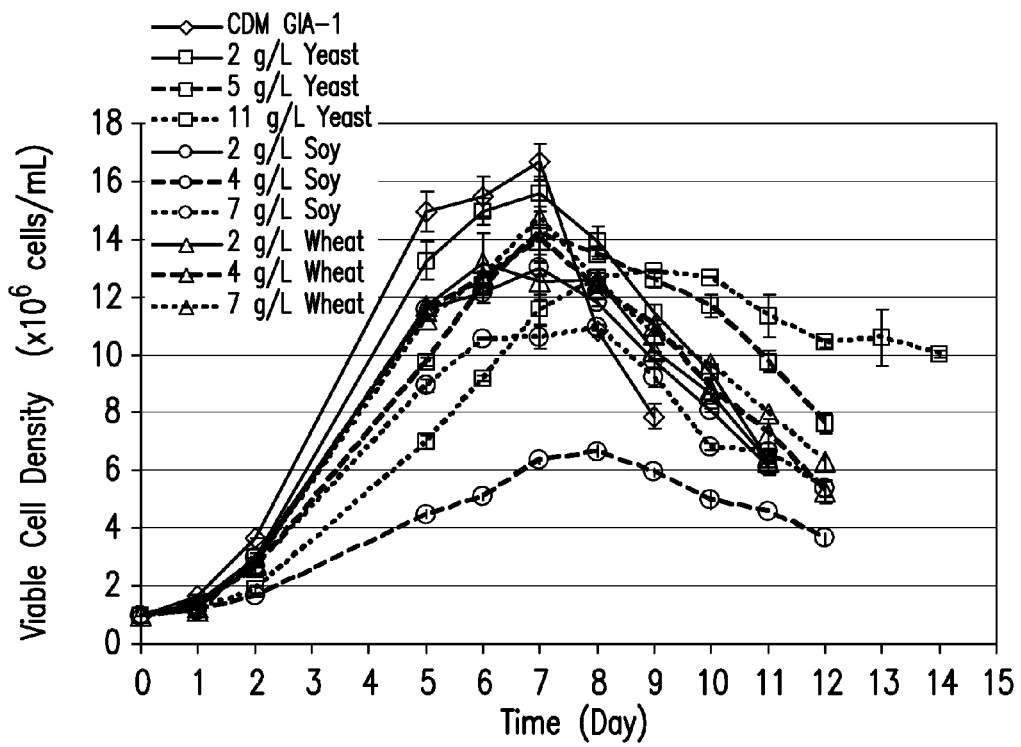
FIG. 25 depicts the effect of yeast, soy, or wheat hydrolysate addition to CDM GIA-1 in CHO cell line producing mAb #1 (a) Culture growth, (b) Culture viability, and (c) Harvest titer.
Figure 25B:
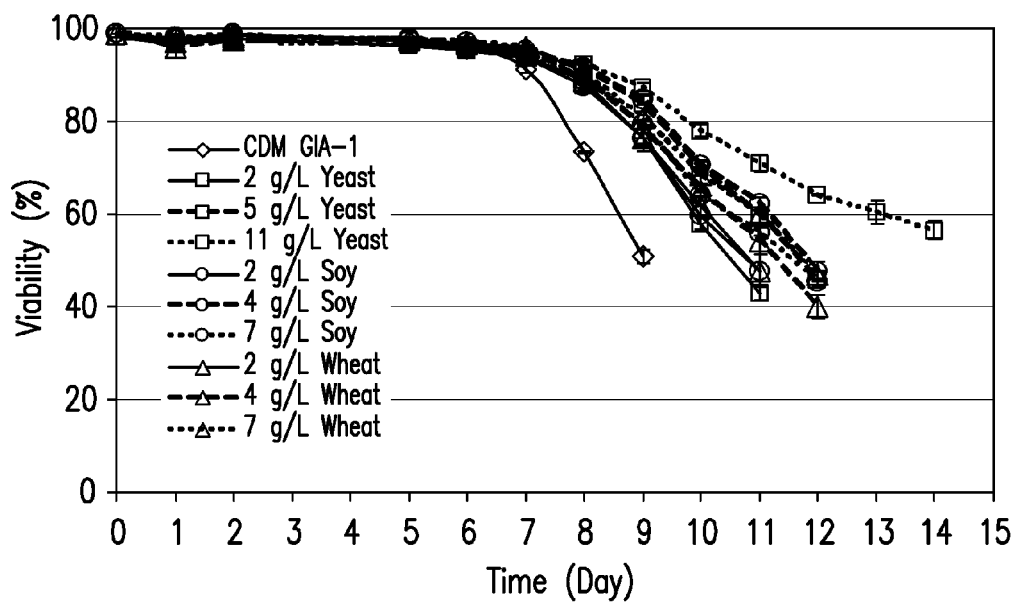
Figure 25C:
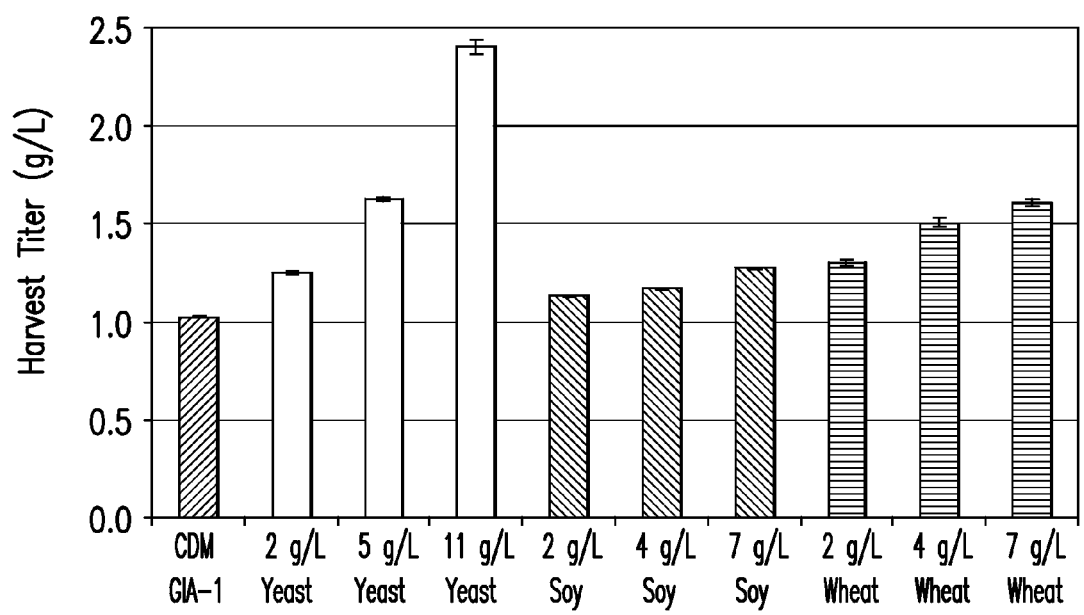

Supplementation of yeast, soy or wheat hydrolysates to the CD media GIA-1 did not affect culture growth profiles dramatically (FIGS. 25A-B). There was some dose-dependent reduction of the peak VCD compared to control as the hydrolysate concentrations increased, particularly in the case of soy hydrolysates, but overall the growth profiles were similar. However, the culture duration was extended to 11-14 days compared to 9 days for control. Cultures supplemented with 11 g/L yeast hydrolysate had a substantial increase in harvest titer (FIG. 25C) that far exceeded the other conditions.

9.3 Oligosaccharide Analysis

Figure 26A:
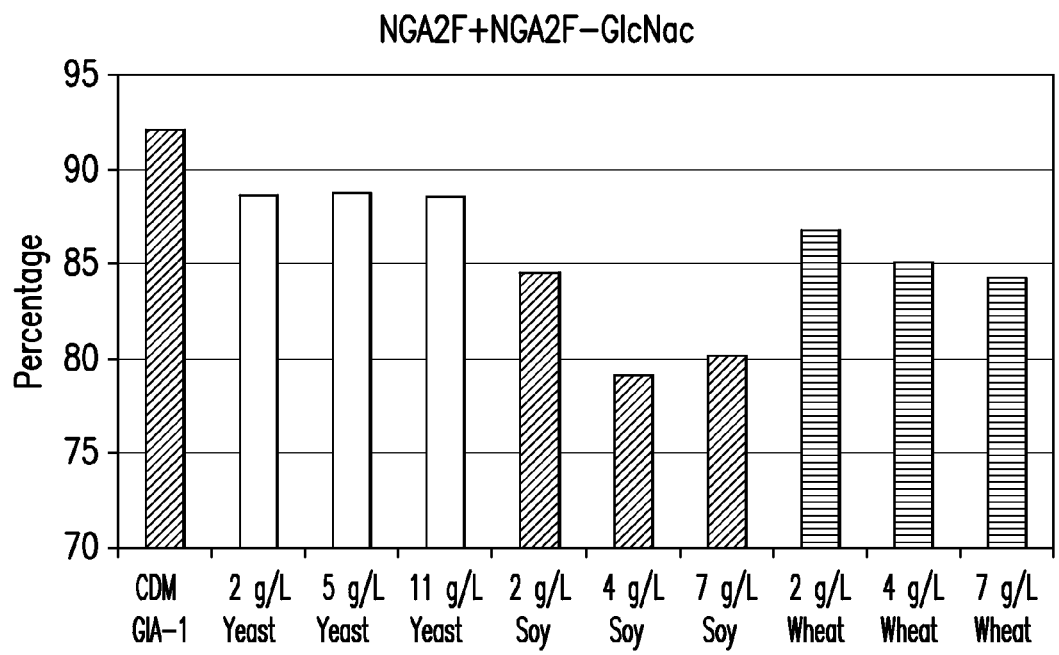
FIG. 26 depicts the effect of yeast, soy, or wheat hydrolysate addition to CDM GIA-1 in CHO cell line producing mAb #1 on (a) NGA2F+NGA2F-GlcNac and (b) NA1F+NA2F.
Figure 26B:
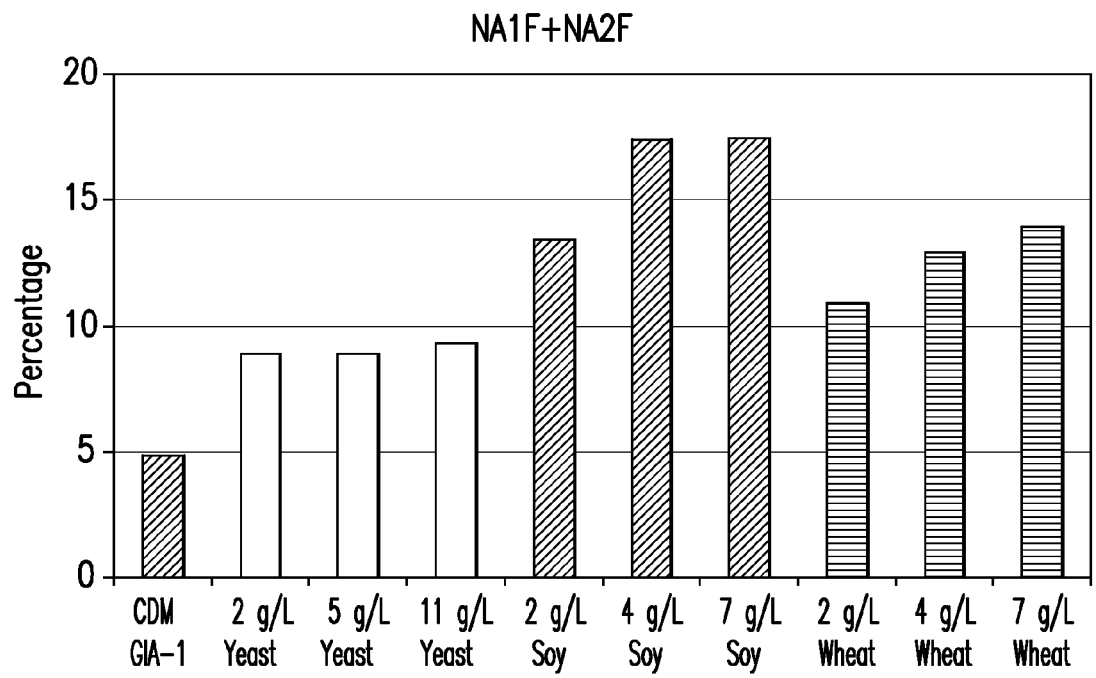

Addition of yeast hydrolysates to CD media GIA-1 lowered the percentage of NGA2F+NGA2F-GlcNac glycans by 3%, and increased the percentage of NA1F+NA2F glycans by 4% compared to control (NGA2F+NGA2F-GlcNac: 92%; NA1F+NA2F: 5%) (FIGS. 26A-B). Addition of soy hydrolysates lowered the percentage of NGA2F+NGA2F-GlcNac glycans by 7-13%, and increased the percentage of NA1F+NA2F glycans by 8-12% compared to control. Addition of wheat hydrolysates lowered the percentage of NGA2F+NGA2F-GlcNac glycans by 5-8%, and increased the percentage of NA1F+NA2F glycans by 6-9% compared to control.

Example 10

Yeast, Soy, or Wheat Hydrolysate Addition to CD Media GIA-1 for Culture of a CHO Cell Line Producing mAb #2

In the study summarized in this example, the effects on glycosylation resulting from the addition of yeast, soy or wheat hydrolysates to CD media GIA-1 in a CHO cell line producing mAb #2 were evaluated.

10.1 Materials and Methods

Adaptation and production media were supplemented with Bacto TC, BBL Phytone Peptone, or Wheat Peptone E1 according to the experimental design in FIG. 46. The control cultures were not supplemented with hydrolysates. All media pH was adjusted to approximately 7.2 and the media osmolality was adjusted to 280-330 mOsmol/kg.

Upon thaw, cells were cultured in CD media GIA-1 growth media in a combination of Corning vented non-baffled shake flasks and maintained on a shaker platform at 140 RPM and 20 L cell bags. Cultures were propagated in a 35° C., 5% $CO_2$ dry incubator. Production cultures were initiated in duplicate 500 mL (200 mL working volume) Corning vented non-baffled shake flasks at an initial VCD of approximately 0.5×$10^6$ cells/mL. The shake flask study was run in an extended-batch mode by feeding a glucose solution (1.25% (v/v) of 40% solution) when the media glucose concentration fell below 3 g/L. For this study, samples were collected daily and measured for cell density and viability using a NOVA cell counter.

10.2 Culture Growth and Productivity

Figure 27A:
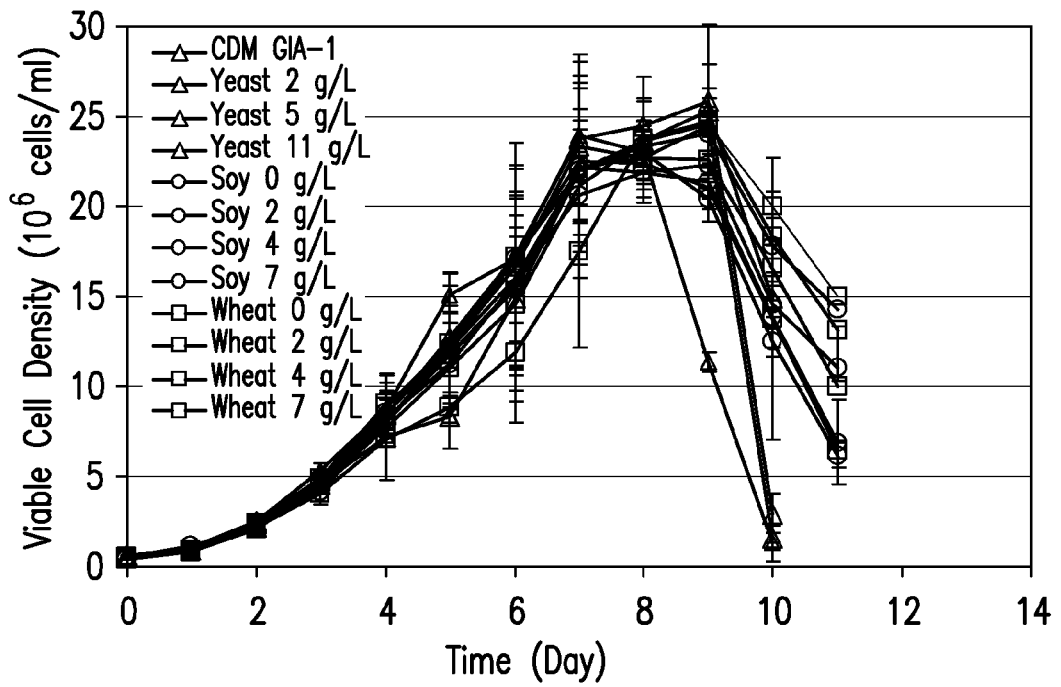
FIG. 27 depicts the effect of yeast, soy, or wheat hydrolysate addition to CDM GIA-1 in CHO cell line producing mAb #2 on (a) Culture growth, (b) Culture viability, and (c) Harvest titer.
Figure 27B:
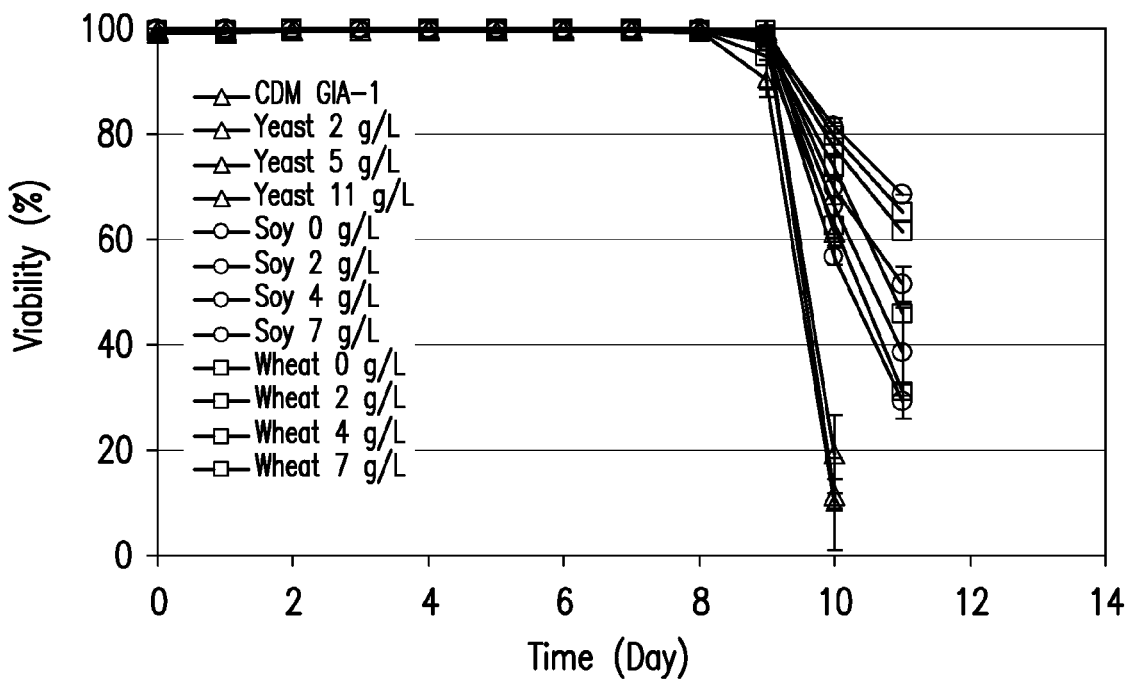
Figure 27C:
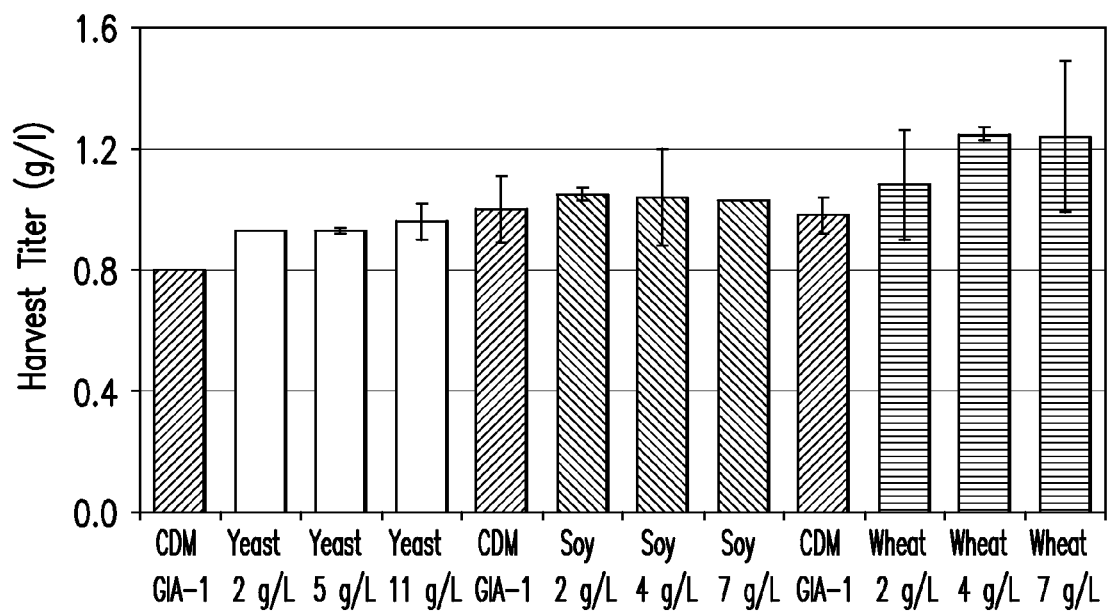

Supplementation of yeast, soy or wheat hydrolysates to CD media GIA-1 did not impact culture growth for most conditions studied compared to control (FIG. 27A). Supplementation with hydrolysates led to higher viability profiles compared to control (FIG. 27B). The addition of wheat hydrolysates increased harvest titer compared to the control (FIG. 27C).

10.3 Oligosaccharide Analysis

Figure 28A:
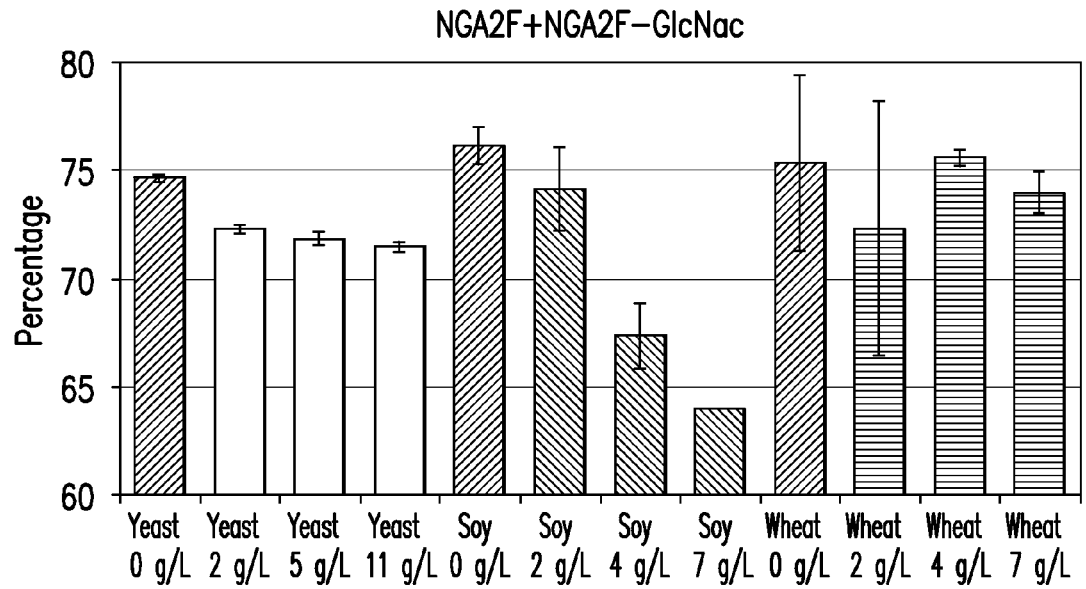
FIG. 28 depicts the effect of yeast, soy, or wheat hydrolysate addition to CDM GIA-1 in CHO cell line producing mAb #2 on (a) NGA2F+NGA2F-GlcNac and (b) NA1F+NA2F.
Figure 28B:
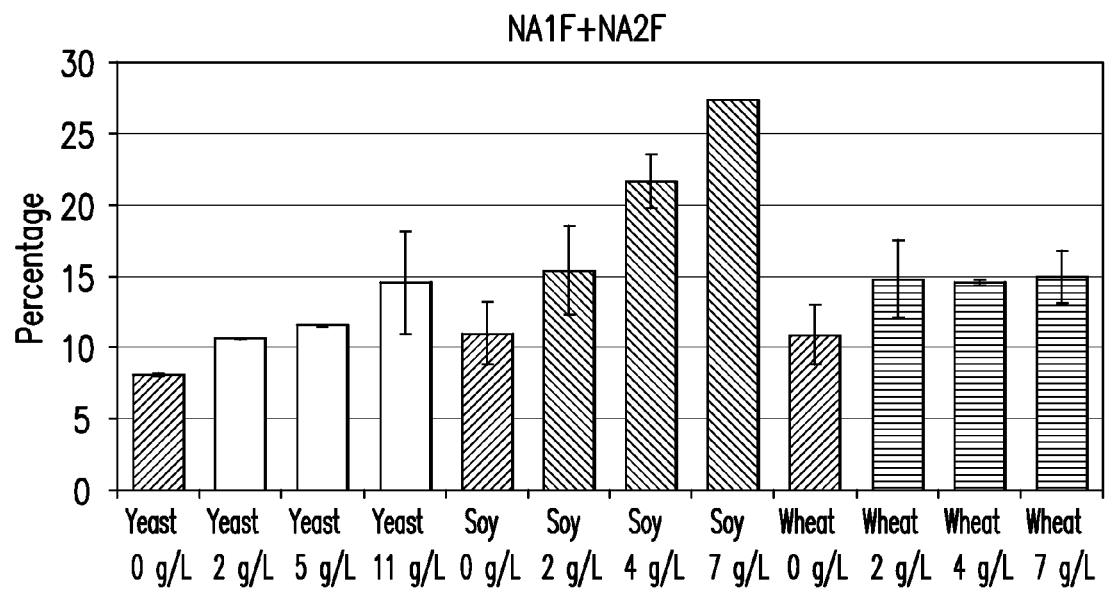

Addition of yeast hydrolysates to CD media GIA-1 lowered the percentage of NGA2F+NGA2F-GlcNac glycans by 3% (FIG. 28A), and increased the percentage of NA1F+NA2F glycans by 7% (FIG. 28B) in a dose-dependent manner compared to control (NGA2F+NGA2F-GlcNac: 75%; NA1F+NA2F: 8%). Addition of soy hydrolysates lowered the percentage of NGA2F+NGA2F-GlcNac by 2-12%, and increased the percentage of NA1F+NA2F by 4-16% compared to control (NGA2F+NGA2F-GlcNac: 76%; NA1F+NA2F: 11%). For this cell line, there was no significant difference in the percentage of NGA2F+NGA2F-GlcNac glycans between the control condition and the cultures supplemented with wheat hydrolysates at the concentration range evaluated. Furthermore, only a minor increase in the percentage of NA1F+NA2F glycans was observed.

Example 11

Combined Yeast, Soy, and/or Wheat Hydrolysate Addition to CD Media CIA-1 for Culture of an Adalimumab-Producing CHO Cell Line #1

In the study summarized in this example, the effects on glycosylation resulting from the individual or combined addition of yeast, soy, and/or wheat hydrolysates to CD media GIA-1 in the adalimumab-producing CHO cell line #1 utilized in Example 1 were evaluated.

11.1 Materials and Methods

Adaptation and production media were supplemented with Bacto TC Yeastolate, BBL Phytone Peptone, and/or Wheat Peptone E1 according to the experimental design in FIGS. 47 and 48. The control cultures were not supplemented with hydrolysates. All media pH was adjusted to approximately 7.1 and the media osmolality was adjusted to 290-300 mOsmol/kg.

Cultures were expanded for 3 passages (3 days each) in their respective adaptation media in a combination of 250 mL (50 mL or 100 mL working volume) and 500 mL (150 mL working volume) Corning vented non-baffled shake flasks and maintained on an orbital shaker at 110 RPM in a 35° C., 5% $CO_2$ dry incubator. Production cultures were initiated in duplicate 500 mL (200 mL working volume) Corning vented non-baffled shake flasks at an initial VCD of approximately 0.5×$10^6$ cells/mL. The shake flask study was run in an extended-batch mode by feeding a glucose solution (1.25% (v/v) of 40% solution) when the media glucose concentration fell below 3 g/L.

11.2 Culture Growth and Productivity

Figure 29A:
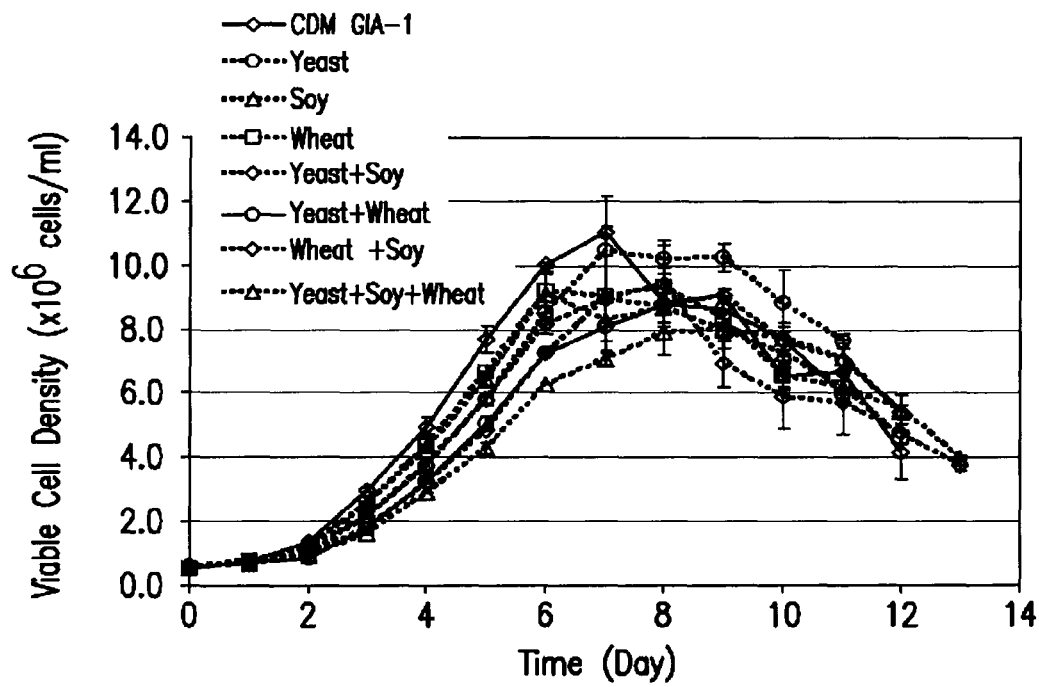
FIG. 29 depicts the effect of combined supplementation of yeast, soy and/or wheat hydrolysates to CDM GIA-1 in adalimumab-producing CHO cell line #1 on (a) Culture growth, (b) Culture viability, and (c) Harvest titer.
Figure 29B:
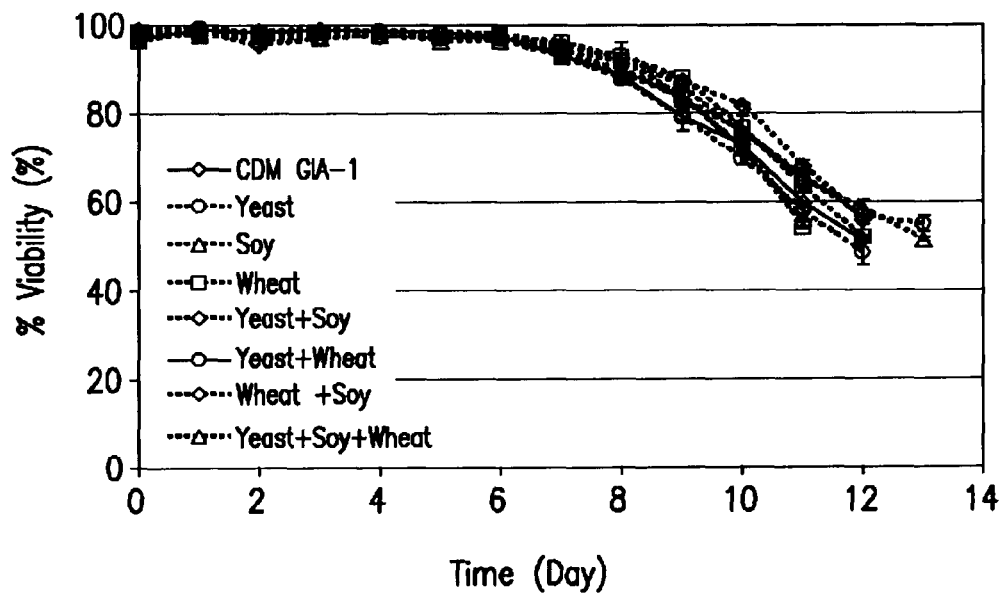
Figure 29C:
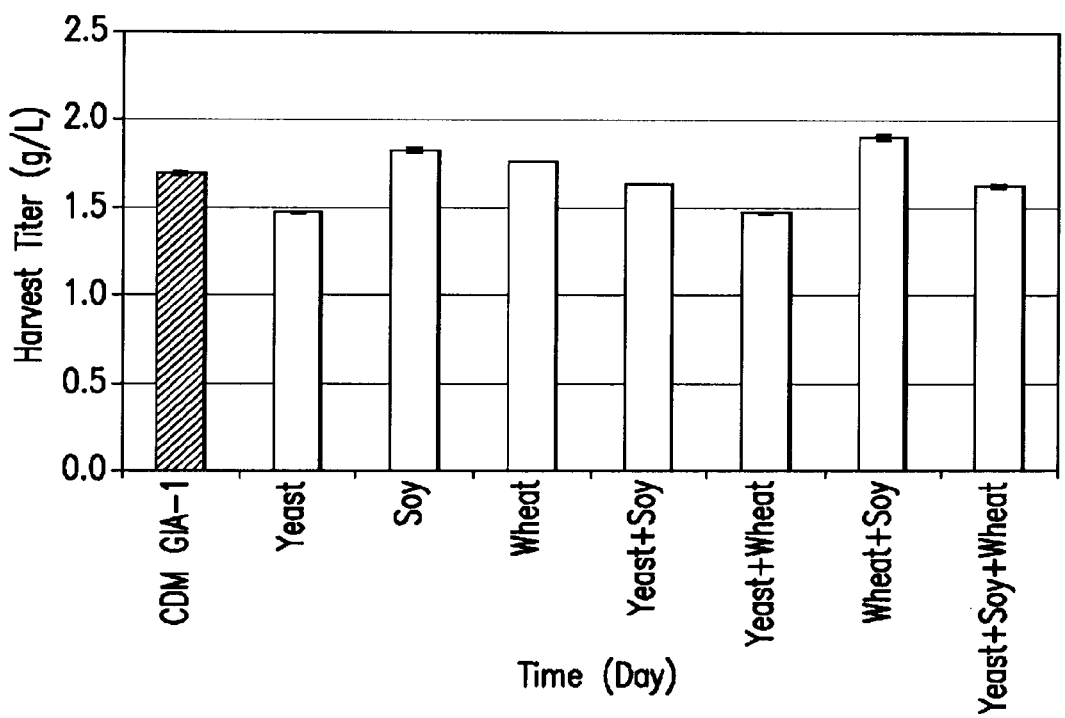

Supplementation of yeast, soy, and/or wheat hydrolysates to CD media GIA-1 resulted in slight growth inhibition and reduced maximum VCD compared to the control (FIG. 29A). Culture viability profiles and harvest titer were comparable for all cultures (FIGS. 29B-C).

11.3 Oligosaccharide Analysis

Figure 30A:
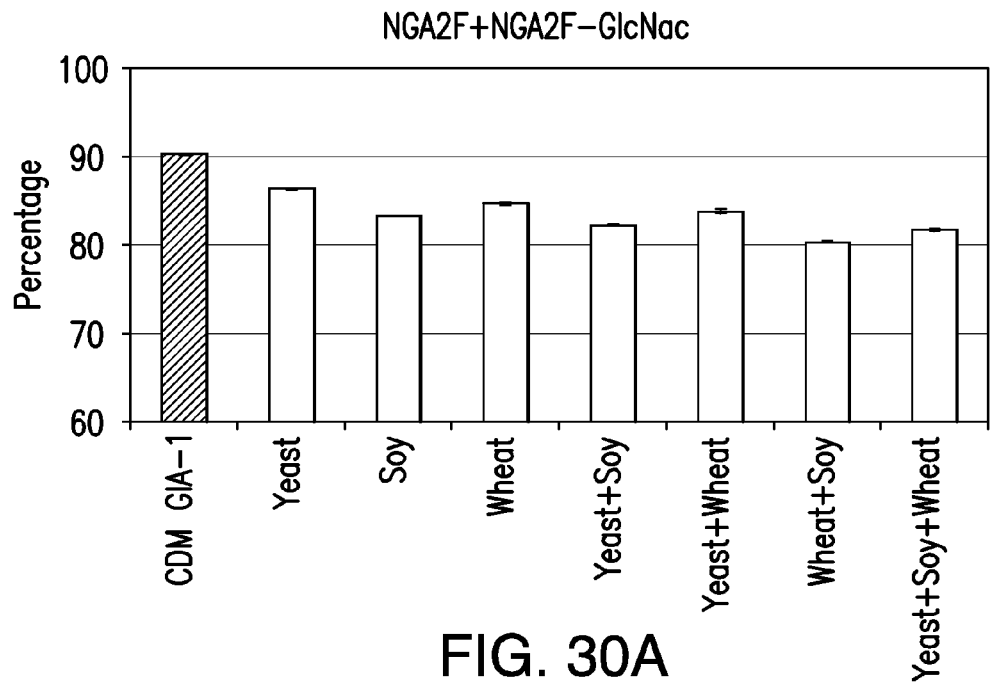
FIG. 30 depicts the effect of combined supplementation of yeast, soy, and/or wheat hydrolysates to CDM GIA-1 in adalimumab-producing CHO cell line #1 on (a) NGA2F+NGA2F-GlcNac and (b) NA1F+NA2F.
Figure 30B:
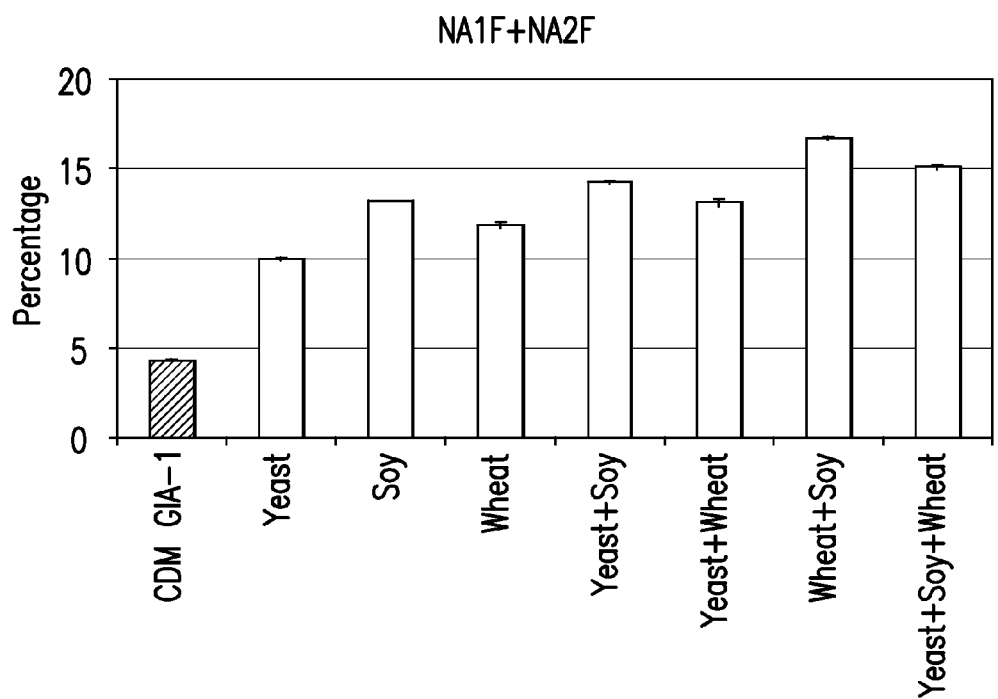

Supplementation of yeast hydrolysates only to CD media GIA-1 decreased the percentage of NGA2F+NGA2F-GlcNac glycans by 4% and increased the percentage of NA1F+NA2F glycans by 6% compared to control (NGA2F+NGA2F-GlcNac: 90%; NA1F+NA2F: 4%) (FIGS. 30A-B). Supplementation of soy hydrolysates only decreased the percentage of NGA2F+NGA2F-GlcNac glycans by 7%, and increased the percentage of NA1F+NA2F glycans by 9% compared to control. Supplementation of wheat hydrolysates only decreased the percentage of NGA2F+NGA2F-GlcNac glycans by 5% and increased the percentage of NA1F+NA2F glycans by 8% compared to control.

The addition of two hydrolysates (yeast and soy; yeast and wheat; soy and wheat) further decreased the percentage of NGA2F+NGA2F-GlcNac glycans and increased the percentage of NA1F+NA2F glycans by a couple of percentages compared to the addition of each component individually (FIGS. 30A-B). Supplementing CD media GIA-1 with all three hydrolysates did not result in any further changes in the glycosylation profile, indicating a saturation state being reached.

Example 12

Effect of Asparagine in CD Media GIA-1 for Culture of Adalimumab-Producing CHO Cell Line #1

In the study summarized in this Example, the effects on product quality attributes resulting from the addition of asparagine to CD media GIA-1 in an adalimumab-producing CHO cell line, generically named CHO cell line #1 were investigated.

12.1 Materials and Methods

The CHO cell line #1 was employed in the study covered here. Upon thaw, cells were expanded in a 19-days seed train and then transferred into seed reactors for up to 7 days in growth medium. The cells were then brought to the laboratory and adapted in 500-mL shaker flasks with 200 mL working volume in CD media GIA 1 medium for 13 days with 3 passages. The shaker flasks were placed on a shaker platform at 110 RPM in a 35° C., 5% $CO_2$ incubator.

The chemical defined growth or production media, was prepared from basal IVGN CD media GIA1. For preparation of the IVGN CD media formulation, the proprietary media was supplemented with L-glutamine, insulin, sodium bicarbonate, sodium chloride, and methotrexate solution. Production media consisted of all the components in the growth medium, excluding methotrexate. In addition, 5 mM of Galactose (Sigma, G5388) and 10 µM of Manganese (Sigma, M1787) were supplemented into production medium. Osmolality was adjusted by the concentration of sodium chloride.

All media was filtered through filter systems (0.22 μm PES) and stored at 4° C. until usage.

Production cultures were initiated in duplicate 500 mL Corning, vented, non-baffled shaker flasks each containing 200 mL culture in dry incubators with 5% $CO_2$ at 35° C. and 110 RPM. Initial VCD was approximately $0.5 \times 10^6$ cells/ml. The shake flask study was run in an extended batch mode by feeding a glucose solution (1.25% (v/v) of 40% solution) when the media glucose concentration fell below 3 g/L. Asparagine stock solution (20 g/L) was fed to culture on Day 6 to increase Asparagine concentration by 0, 0.4, 1.2 and 2.0 g/L.

Samples were taken daily from each reactor to monitor growth. The following equipment was used to analyze the samples: Cedex cell counter for cell density and viability; YSI 7100 analyzer for glucose and lactate concentration.

Some of the daily samples and the harvest samples were centrifuged at 3,000 rpm for 30 min and then supernatants were stored at −80° C. The thawed harvest samples were subsequently filtered through a 0.2 μm filter, purified by Protein A chromatography, and then oligosaccharide analysis was performed as described in Example 1.

12.2 Culture Growth and Productivity

Figure 31A:
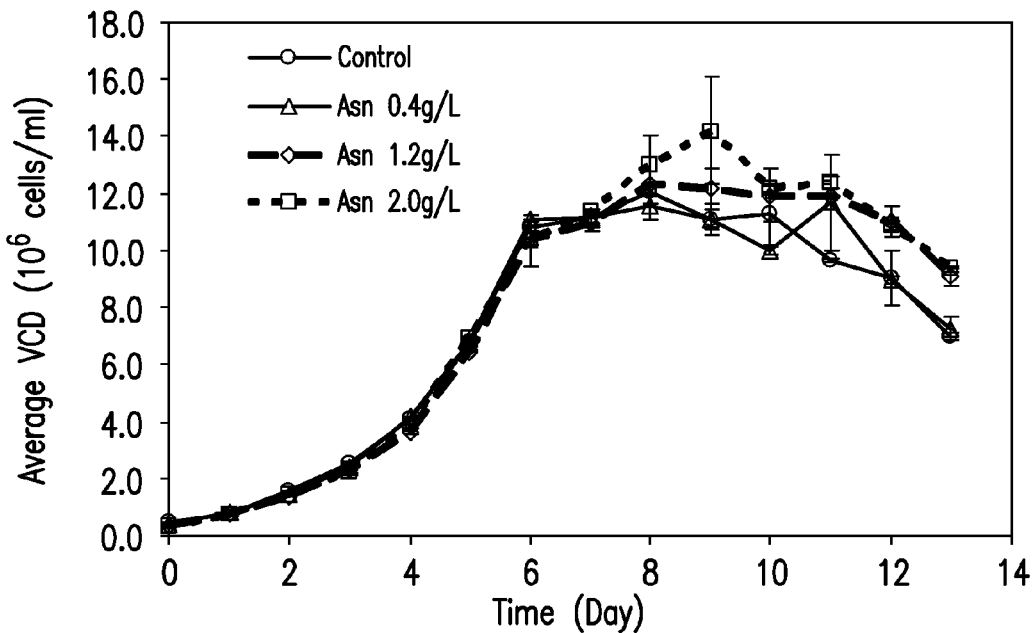
FIG. 31 depicts the dose dependent effect of supplementation of asparagine on Day 6 to CDM GIA-1 in adalimumab-producing CHO cell line #1 on culture growth (a) and culture viability (b) and product titer (c).
Figure 31B:
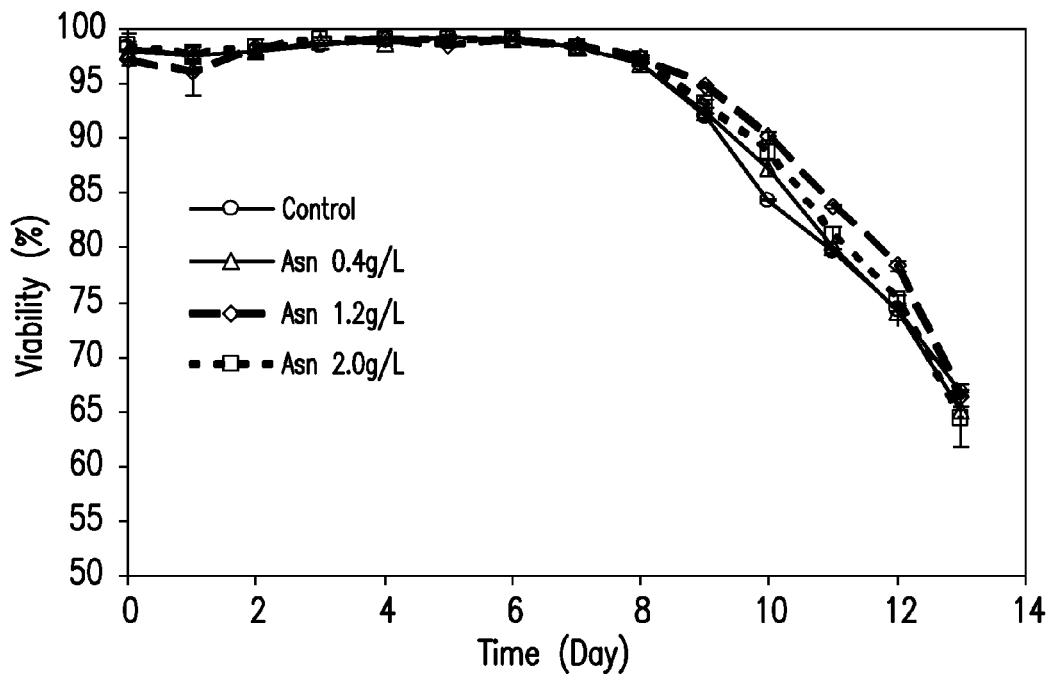
Figure 31C:
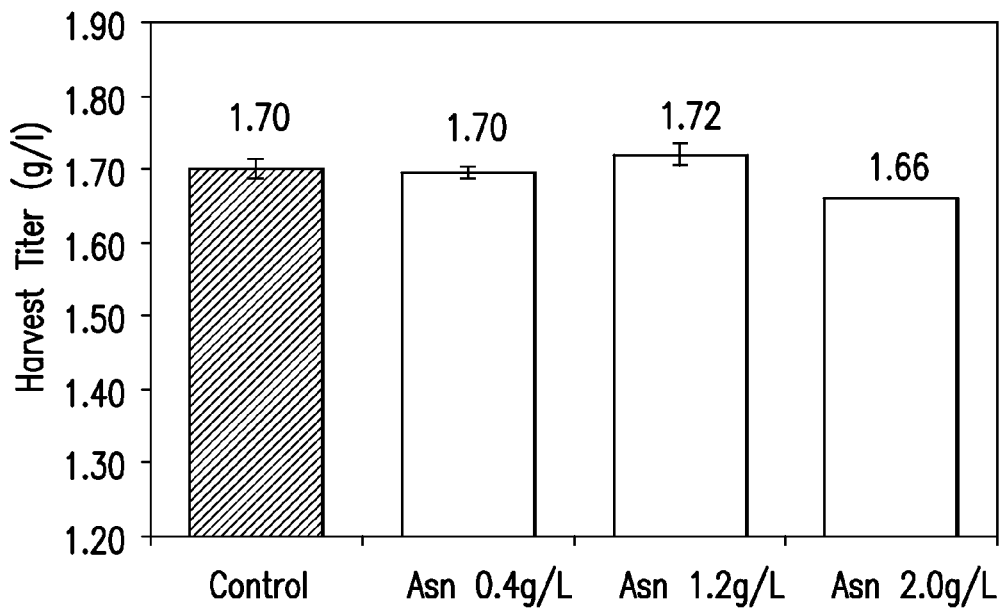

Feeding of asparagine to CD media GIA-1 did not impact culture growth for most conditions studied as compared to the control (FIG. 31A). The cultures showed similar growth rates and reached maximum VCD of $\sim 12 \times 10^6$ cells/mL. Culture viabilities were also very similar to that of the controls (FIG. 31B). Similarly, all the cultures examined here resulted in comparable harvest titers of approximately 1.7 g/L (FIG. 31C).

12.3 Oligosaccharide Analysis

Figure 32A:
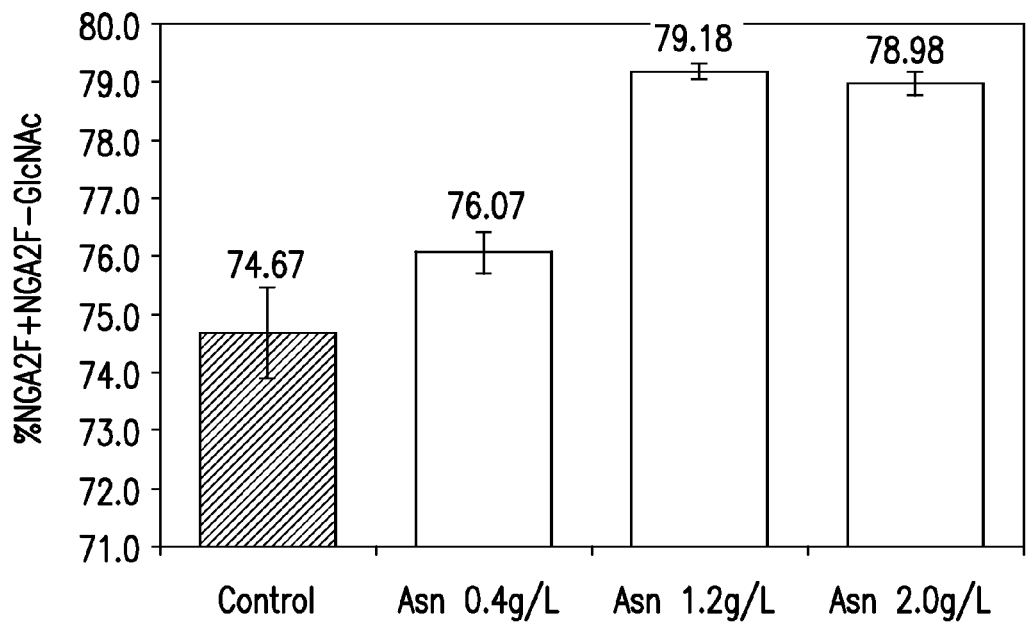
FIG. 32 depicts the dose dependent effect of supplementation of asparagine on Day 6 to CDM GIA-1 in adalimumab-producing CHO cell line #1 on NGA2F and NGA2F-GlcNac glycans (a) and on NA1F and NA2F glycans (b).

The effect of asparagine addition on oligosaccharide distribution was consistent with the experiments performed in hydrolysate based media described above. The addition of asparagine increased NGA2F+NGA2F-GlcNac glycans in a dose dependent manner (FIG. 32A). The percentage of NGA2F+NGA2F-GlcNac in the control sample (without Asparagine addition) was as low as 74.7%. In the sample with the addition of asparagine the percentage of NGA2F+NGA2F-GlcNAc was increased to 76.1% (0.4 g/L of asparagine), 79.2% (1.2 g/L of asparagine), and 79.0% (2.0 g/L of asparagine), for a total increase of 4.5%.

Figure 32B:
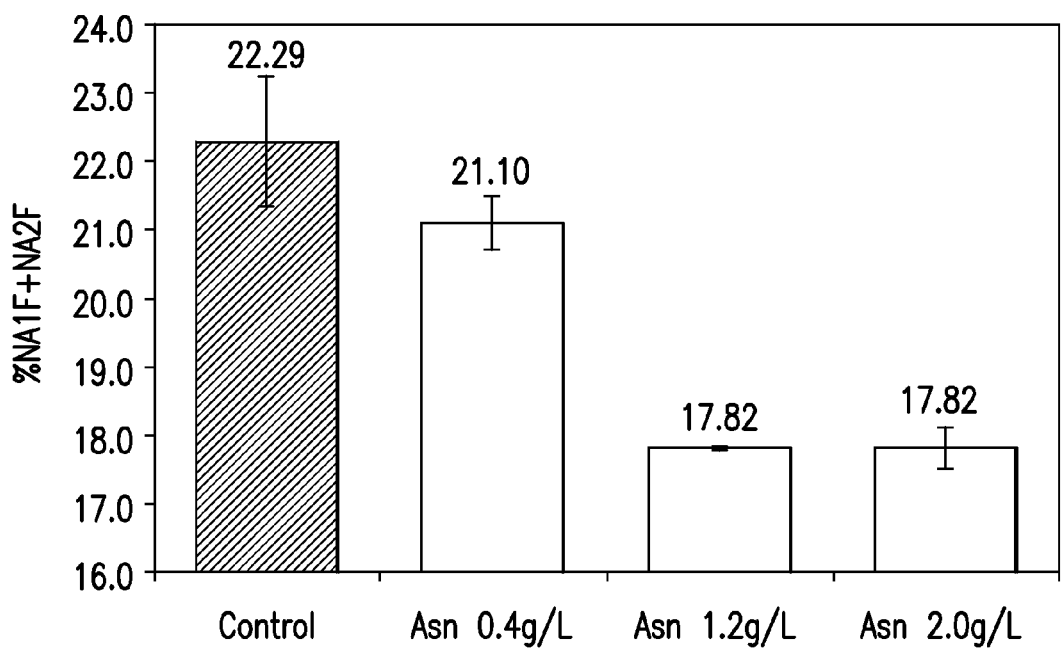

The percentage of NA1F+NA2F in the control sample (without asparagine addition) was as high as 22.3% (FIG. 32B). In the sample with the addition of asparagine the percentage of NA1F+NA2F was decreased to 21.1% (0.4 g/L of asparagine), 17.8% (1.2 g/L of asparagine), and 17.8% (2.0 g/L of asparagine), for a total reduction of 4.5%.

Example 13

Effect of Asparagine in CD Media GIA-1 for Culture of Adalimumab-Producing CHO Cell Line #3

In the study summarized in Example 13, the effects on product quality attributes resulting from the addition of asparagine to CD media GIA-1 in an adalimumab-producing CHO cell line, generically named CHO cell line #3 were investigated.

13.1 Materials and Methods

The CHO cell line #3 was employed in the study covered here. Upon thaw, adalimumab producing cell line #3 was cultured in CD media GIA-1 in a combination of vented shake flasks on a shaker platform @140 rpm and 20 L wave bags. Cultures were propagated in a 36° C., 5% $CO_2$ incubator to obtain the required number of cells to be able to initiate production stage cultures.

The chemical defined growth or production media was prepared from basal IVGN CD media GIA1. For preparation of the IVGN CD media formulation, the proprietary media was supplemented with L-glutamine, sodium bicarbonate, sodium chloride, and methotrexate solution. Production media consisted of all the components in the growth medium, excluding methotrexate. In addition, 10 mM of Galactose (Sigma, G5388) and 0.2 μM of Manganese (Sigma, M1787) were supplemented into production medium. Osmolality was adjusted by the concentration of sodium chloride. All media was filtered through filter systems (0.22 μm PES) and stored at 4° C. until usage.

Production cultures were initiated in duplicate 500 mL Corning, vented, non-baffled shaker flasks each containing 200 mL culture in dry incubators with 5% $CO_2$ at 36° C. and 140 RPM. Initial VCD was approximately $0.5 \times 10^6$ cells/ml. The shake flask study was run in an extended batch mode by feeding a glucose solution (1.25% (v/v) of 40% solution) when the media glucose concentration fell below 3 g/L. Asparagine stock solution (20 g/L) was fed to culture on Day 6 to increase asparagine concentration by 0, 0.4, 0.8, 1.2, 1.6, and 2.0 g/L.

Samples were taken daily from each reactor to monitor growth. The following equipment was used to analyze the samples: Cedex cell counter for cell density and viability; YSI 7100 analyzer for glucose and lactate concentration.

Some of the daily samples and the harvest samples were centrifuged at 3,000 rpm for 30 min and then supernatants were stored at −80° C. The thawed harvest samples were subsequently filtered through a 0.2 μm filter, purified by Protein A chromatography, and then oligosaccharide analysis was performed as described in Example 1.

13.2 Culture Growth and Productivity

Figure 33A:
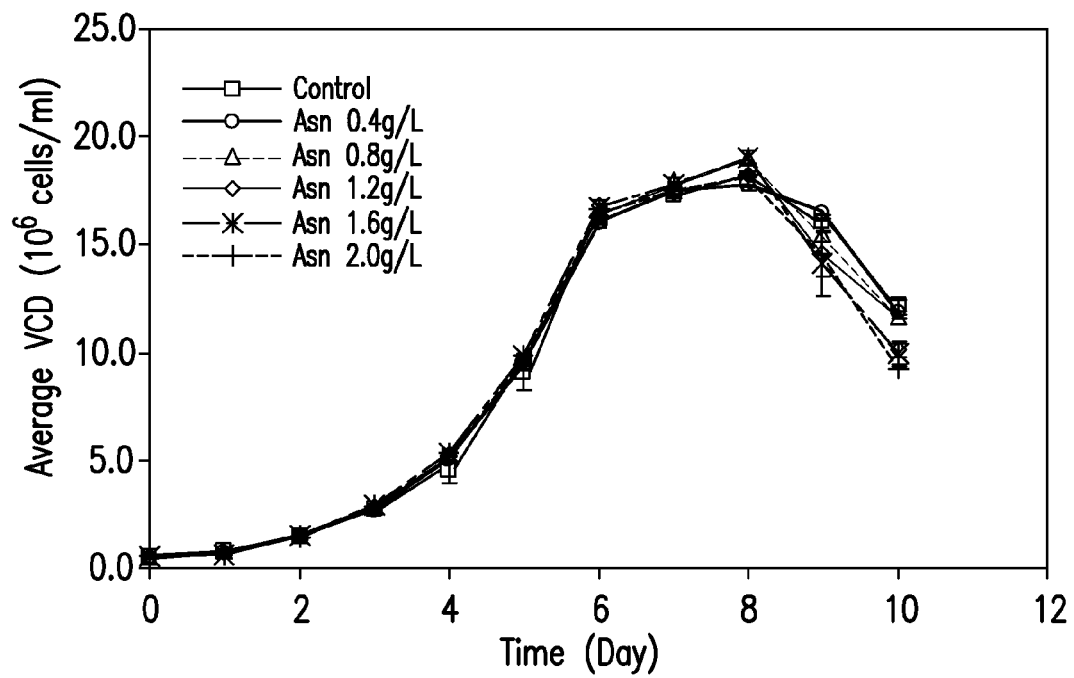
FIG. 33 depicts the dose dependent effect of supplementation of asparagine on Day 6 to CDM GIA-1 in adalimumab-producing CHO cell line #2 on culture growth (a) and culture viability (b) and product titer (c).
Figure 33B:
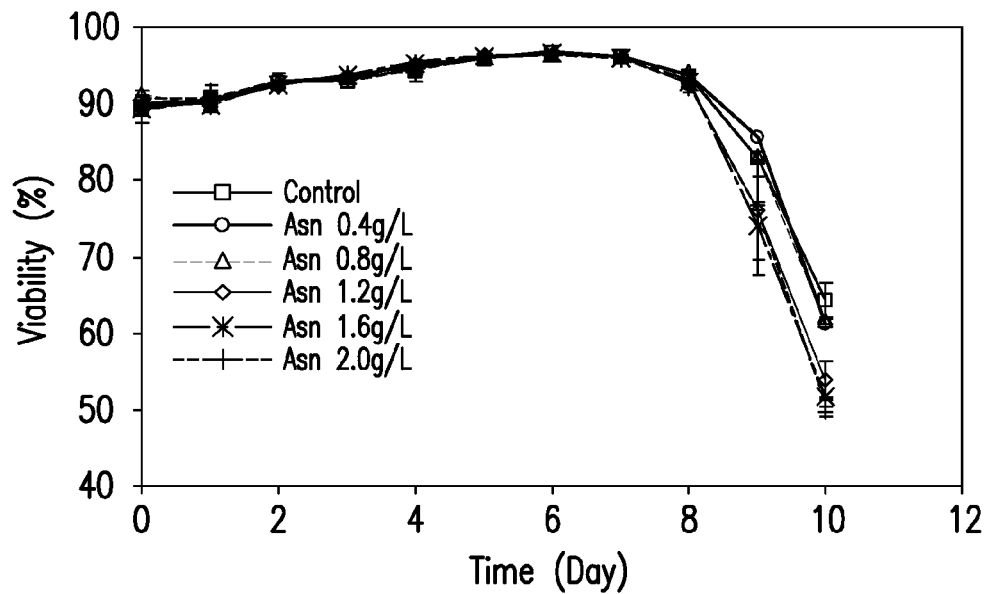
Figure 33C:
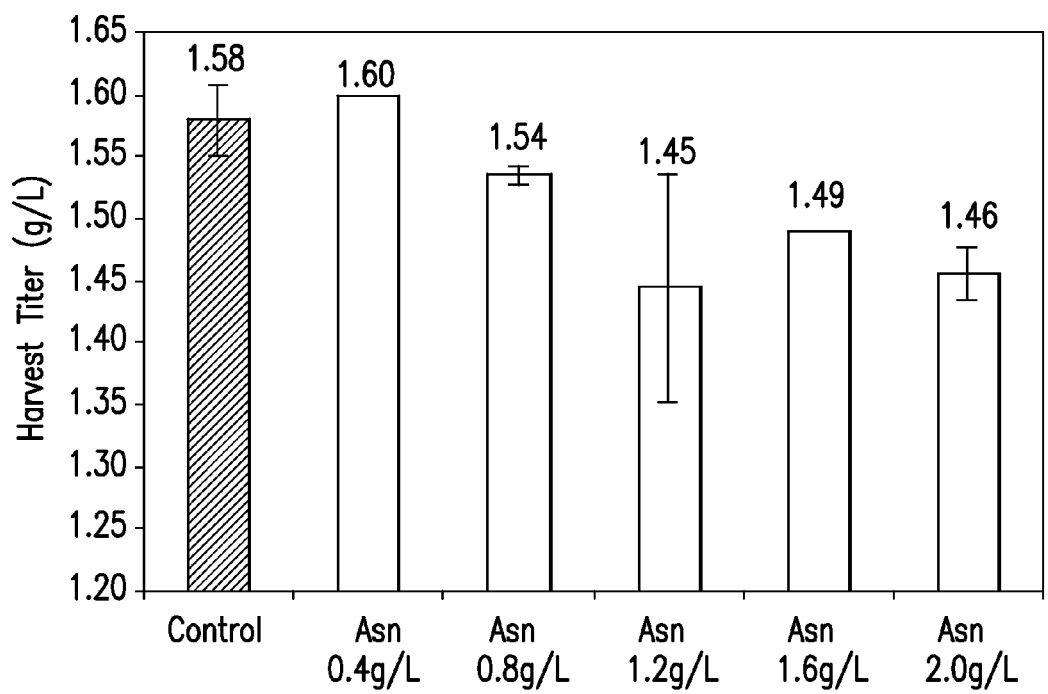

The experiment described in the instant Example used a different cell line (i.e., CHO cell line #3) in CD media GIA-1. Culture growth and viability profiles were comparable among all test conditions with different dosage of asparagine added on day 6 (FIGS. 33A and 33B). All cultures reached maximum VCD of $\sim 18-19 \times 10^6$ cells/mL. The product titer ($\sim 1.5$-1.6 g/L) was slightly reduced when higher dosage of asparagine was added (FIG. 33C).

13.3 Oligosaccharide Analysis

Figure 34A:
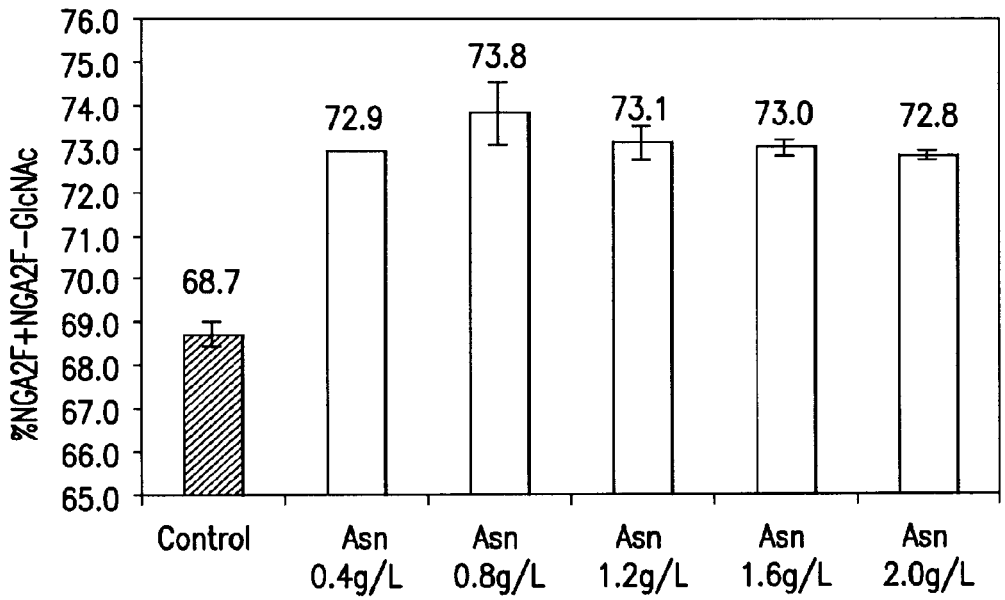
FIG. 34 depicts the dose dependent effect of supplementation of asparagine on Day 6 to CDM GIA-1 in adalimumab-producing CHO cell line #2 on NGA2F and NGA2F-GlcNac glycans (a) and on NA1F and NA2F glycans (b).
Figure 34B:
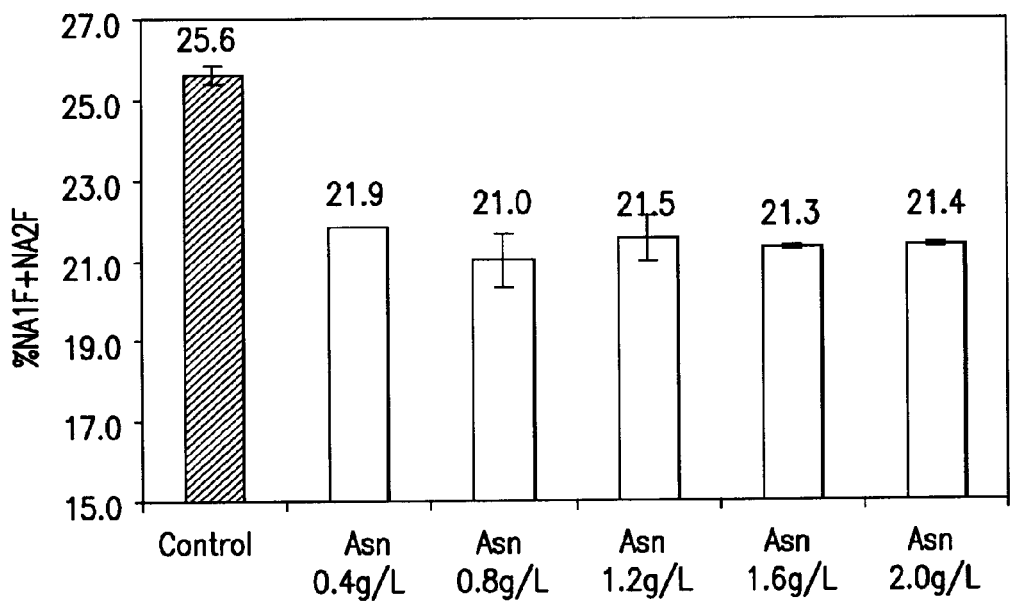

Again, the addition of asparagine increased NGA2F+NGA2F-GlcNac (FIG. 34A). The percentage of NGA2F+NGA2F-GlcNac in the control sample (without asparagine addition) was as low as 68.7%. In the sample with the addition of asparagine, the percentage of NGA2F+NGA2F-GlcNac was increased by 4.1-5.1% when 0.4 to 2.0 g/L asparagine was added on day 6 (FIG. 34A). The percentage of NA1F+NA2F in the control sample (without asparagine addition) was as high as 25.6% (FIG. 34B). In the sample with the addition of asparagine the percentage of NA1F+NA2F was decreased by 3.8-4.6% when 0.4 to 2.0 g/L asparagine was added on day 6 (FIG. 34B).

Example 14

Effect of Asparagine in a Shaker Flask Batch Culture in CD Media GIA-1 with a CHO Cell Line Producing mAb #2

In the studies summarized in Example 14, the effects on product quality attributes resulting from the addition of asparagine to CD media GIA-1 from Life Technologies Gibco in a CHO cell line producing monoclonal antibody #2 were investigated. In this instant Example, asparagine was either supplemented into culture media during media preparation or added on day 5 of the cell culture process.

14.1 Materials and Methods mAb #2 producing cell line was employed in the study covered here. Upon thaw, cells were cultured in chemically defined growth media in a combination of vented baffled shake flasks (Corning) on a shaker platform at 140 RPM. All media pH was adjusted to approximately 7.2 and the media osmolality was adjusted to 280-330 mOsmol/kg.

Cultures were propagated in a 35° C., 5% $CO_2$ incubator to obtain the required number of cells to be able to initiate production stage cultures. Production cultures were initiated in duplicate 500 mL vented non-baffled Corning shake flasks (200 mL working volume) at an initial viable cell density (VCD) of approximately $0.5 \times 10^6$ cells/mL. The shake flask study was run in an extended batch mode by feeding a glucose solution (1.25% (v/v) of 40% solution) when the media glucose concentration fell below 3 g/L. Asparagine (Sigma, Catalog Number A4284) were solubilized in Milli-Q water to make a 30 g/L stock solution. All media was filtered through Corning or Millipore 1 L filter systems (0.22 μn PES) and stored at 4° C. until usage.

For asparagine supplemented into culture media during media preparation, asparagine stock solution was supplemented to production media to increase asparagine concentration by 0, 0.4, 0.8 and 1.6 g/L. After addition of asparagine, media was brought to a pH similar to non-supplemented (control) media using 5N hydrochloric acid/5N NaOH, and it was brought to an osmolality similar to non-supplemented (control) media by adjusting the concentration of sodium chloride. For asparagine addition study, asparagine stock solution was added to culture on Day 5 to increase Asparagine concentration by 0, 0.4, 0.8 and 1.6 g/L.

For all studies described throughout this invention, samples were collected daily and measured for cell density and viability using a NOVA cell counter. Retention samples for titer analysis via Poros A method were collected by centrifugation at 12,000 RPM for 5 min when the culture viability began declining. The cultures were harvested by collecting 125 mL aliquots and centrifuging at 3,000 RPM for 30 min when culture viability was near or below 50%. All supernatants were stored at −80° C. until analysis. The harvest samples were Protein A purified and then oligosaccharide analysis was performed as described in Example 1.

14.2 Culture Growth and Productivity

Figure 35A:
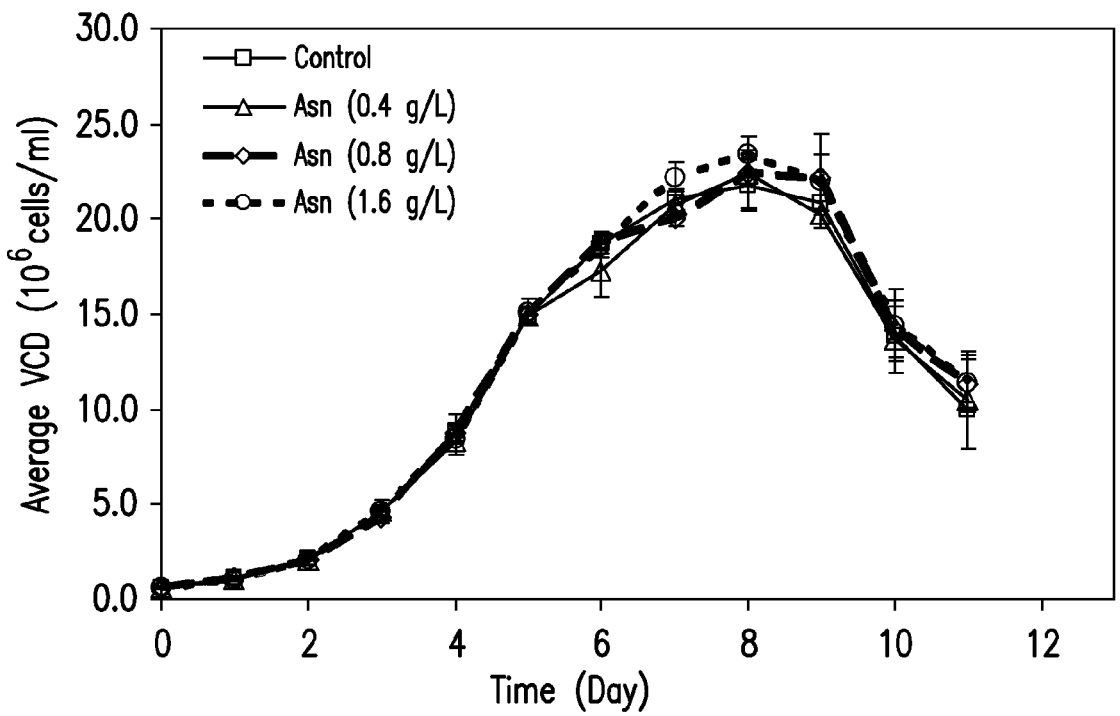
FIG. 35 depicts the dose dependent effect of supplementation of asparagine during medium preparation to CDM GIA-1 in CHO cell line producing mAb #2 on culture growth (a) and culture viability (b) and product titer (c).
Figure 35B:
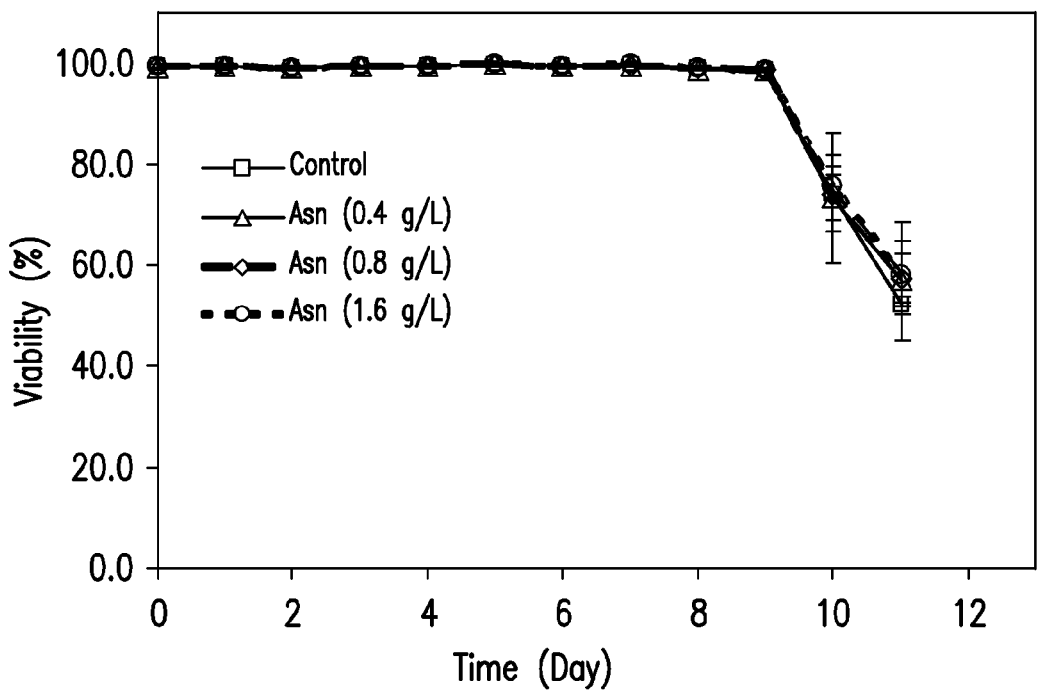
Figure 35C:
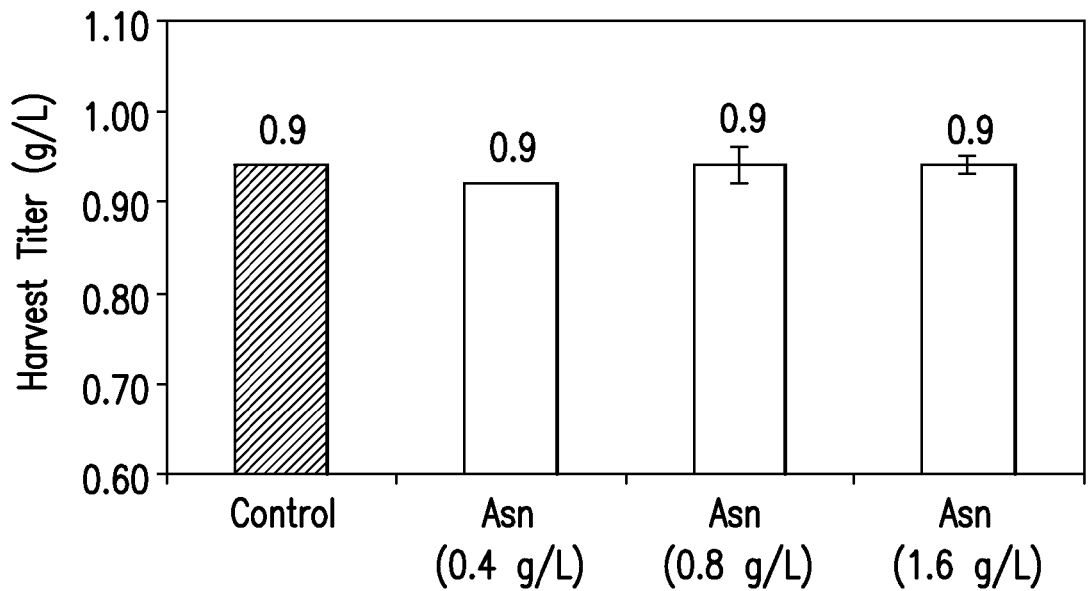
Figure 37A:
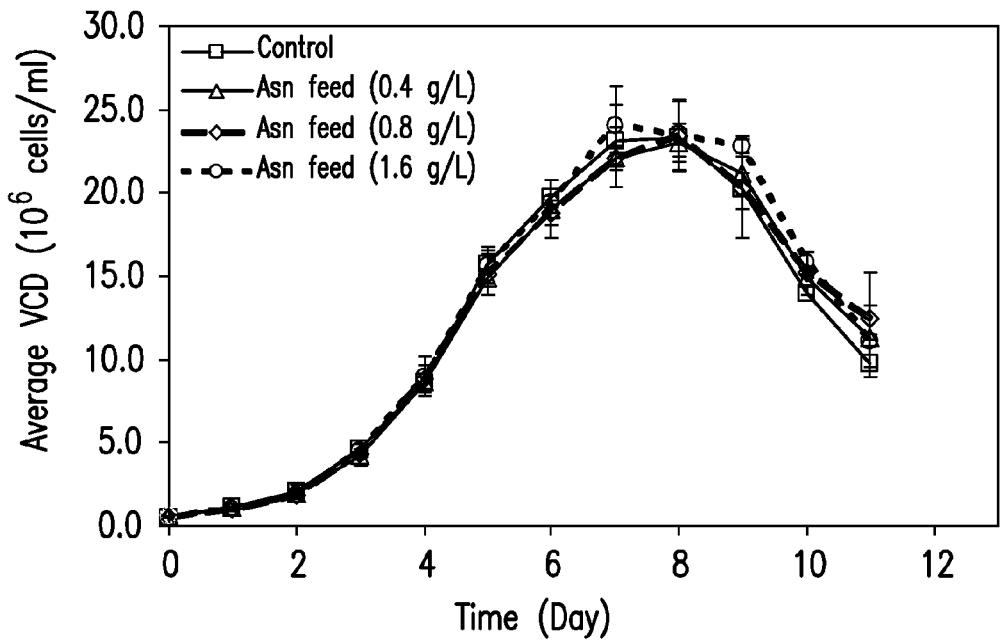
FIG. 37 depicts the dose dependent effect of supplementation of asparagine on Day 5 to CDM GIA-1 in CHO cell line producing mAb #2 on culture growth (a) and culture viability (b) and product titer (c).
Figure 37B:
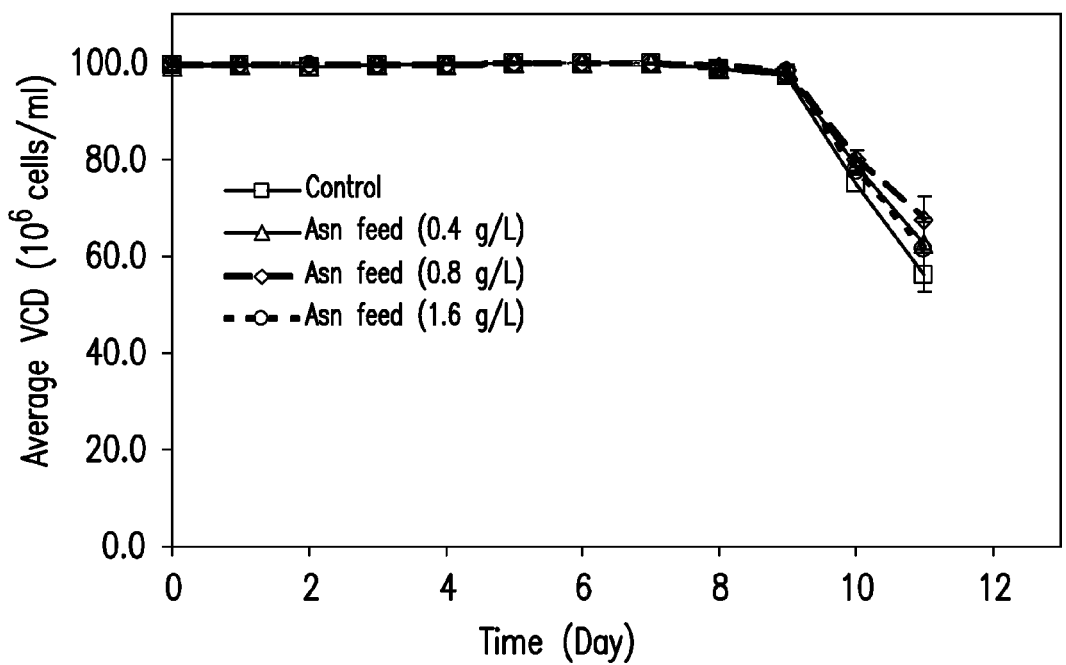
Figure 37C:
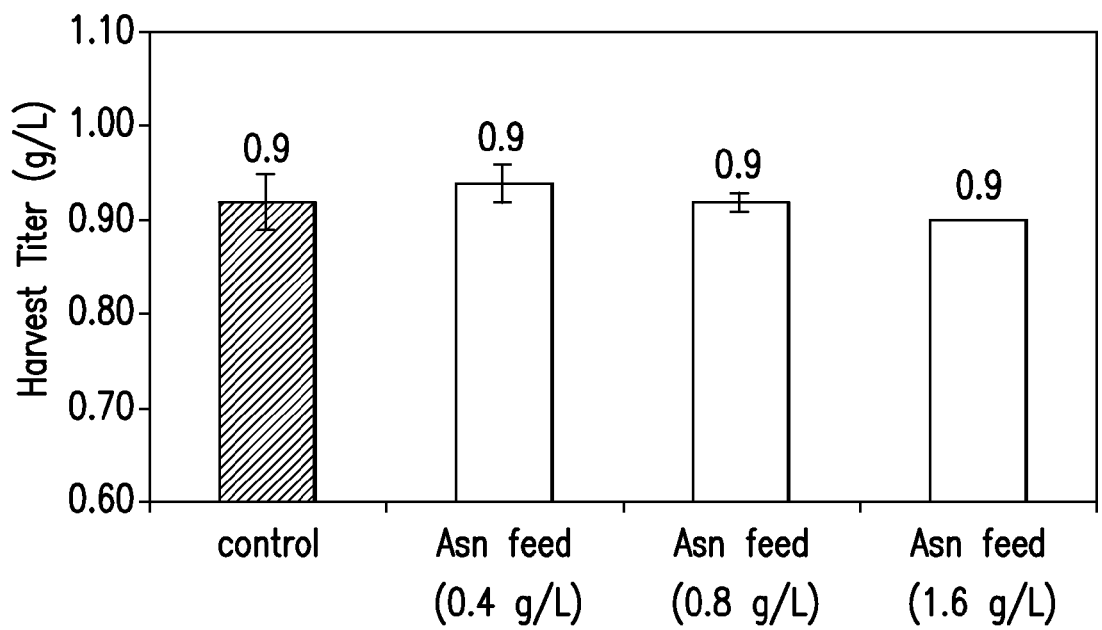

Adding asparagine to CD media GIA-1 during medium preparation or on day 5 of the cell culture did not impact culture growth for most conditions studied as compared to the non-supplemented 0 g/L controls (FIGS. 45A and 47A). The cultures showed similar growth rates and reached maximum VCD of $22-24 \times 10^6$ cells/mL. Culture viabilities were also very similar to that of the controls (FIGS. 35B and 37B). Similarly, all the cultures examined here resulted in comparable harvest titers of approximately 0.9 g/L of mAb #2 (FIGS. 35C and 37C).

14.3 Oligosaccharide Analysis

Figure 36A:
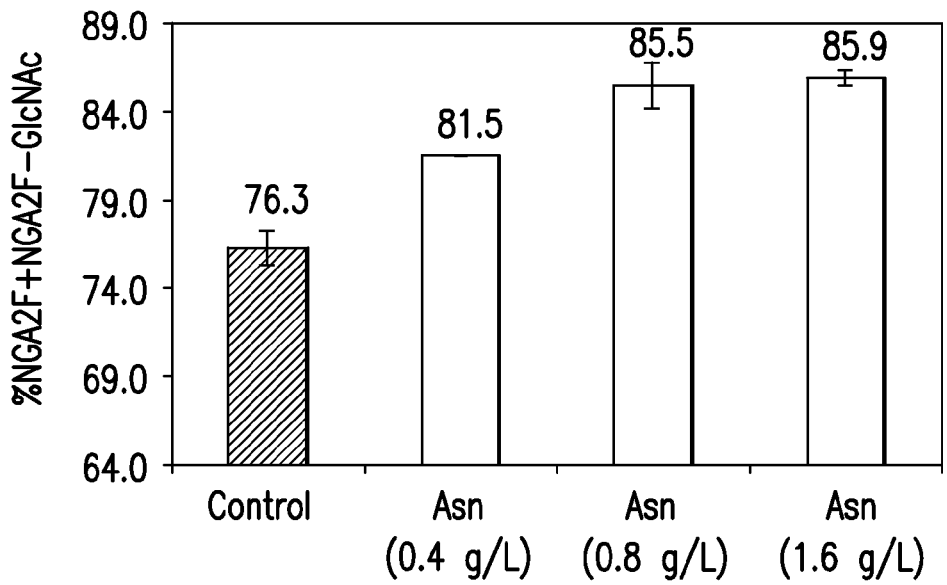
FIG. 36 depicts the dose dependent effect of supplementation of asparagine during medium preparation to CDM GIA-1 in CHO cell line producing mAb #2 on NGA2F and NGA2F-GlcNac glycans (a) and on NA1F and NA2F glycans (b).
Figure 36B:
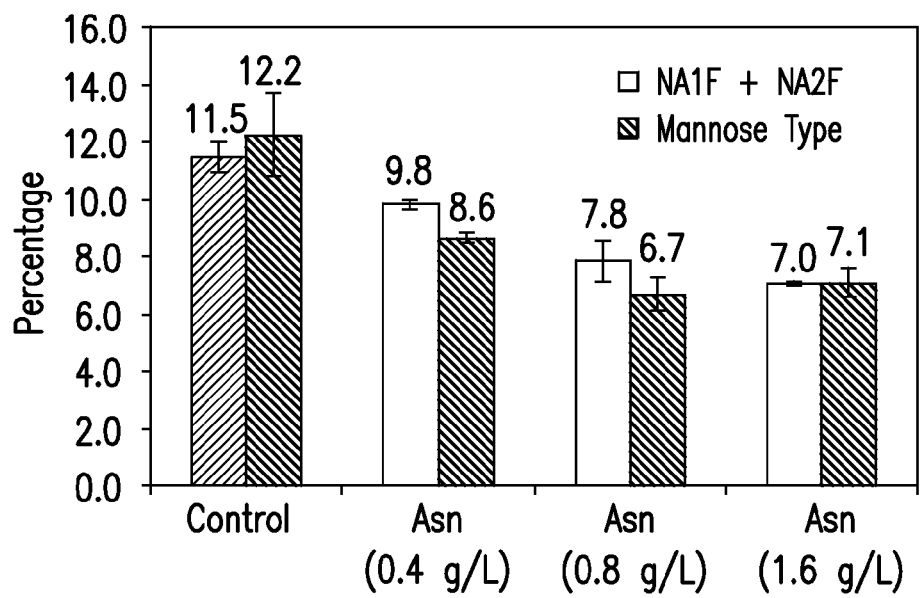

The addition of asparagine during medium preparation increased NGA2F+NGA2F-GlcNac glycans in a dose dependent manner (FIG. 36A). The percentage of NGA2F+NGA2F-GlcNac in the control sample (without asparagine addition) was as low as 76.3%. In the sample with the addition of asparagine the percentage of NGA2F+NGA2F-GlcNac was increased to 81.5% (0.4 g/L of asparagine), 85.5% (0.8 g/L of asparagine), and 85.9% (1.6 g/L of asparagine), for a total increase of 9.6%. The percentage of NA1F+NA2F in the control sample (without asparagine addition) was as high as 11.5% (FIG. 36B). In the sample with the addition of asparagine the percentage of NA1F+NA2F was decreased to 9.8% (0.4 g/L of asparagine), 7.8% (0.8 g/L of asparagine), and 7.0% (1.6 g/L of asparagine), for a total reduction of 4.5%. With mAb #2 cell line used in the study, the percentage of Mannose type glycans was also decreased with the supplementation of asparagine. The percentage of Mannoses in the control sample (without asparagine addition) was as high as 12.2% (FIG. 36B). In the sample with the addition of asparagine the percentage of Mannoses was decreased to 8.6% (0.4 g/L of asparagine), 6.7% (0.8 g/L of asparagine), and 7.1% (1.6 g/L of asparagine), for a total reduction of 5.5%.

Figure 38A:
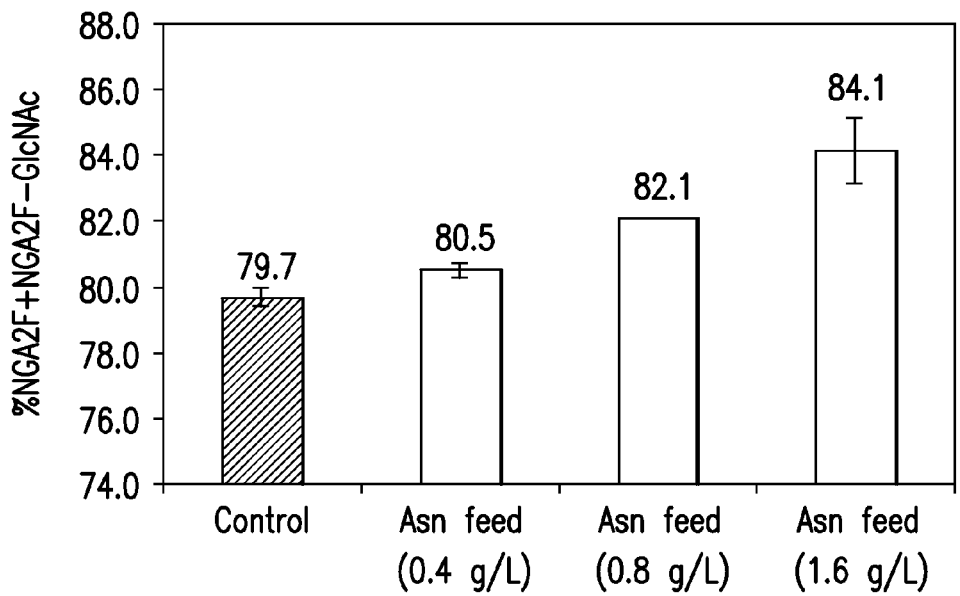
FIG. 38 depicts the dose dependent effect of supplementation of asparagine on Day 5 to CDM GIA-1 in CHO cell line producing mAb #2 on NGA2F and NGA2F-GlcNac glycans (a) and on NA1F and NA2F glycans (b).
Figure 38B:
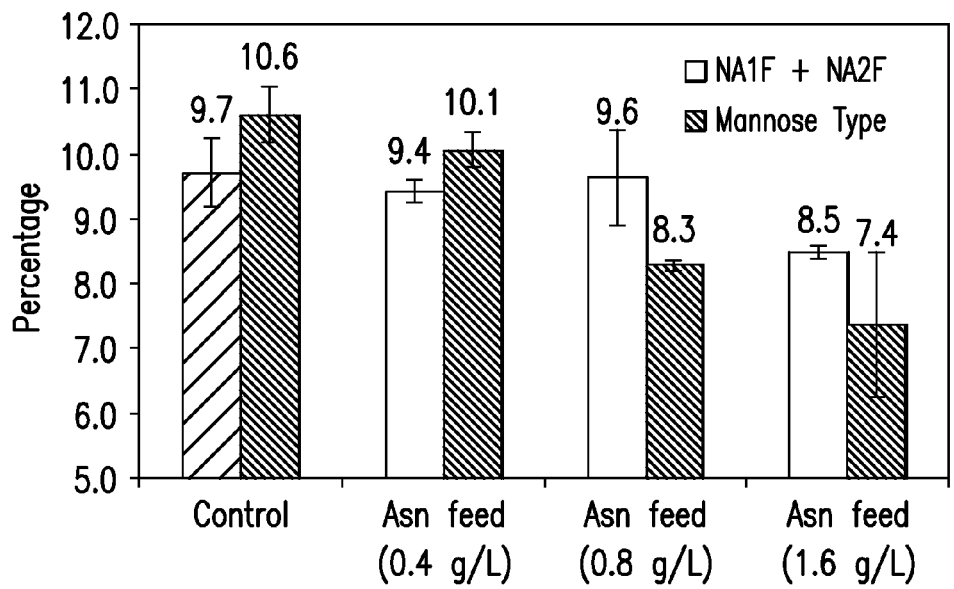

The addition of asparagine on day 5 of the culture also increased NGA2F+NGA2F-GlcNac glycans in a dose dependent manner (FIG. 38A). The percentage of NGA2F+NGA2F-GlcNac in the control sample (without asparagine addition) was as low as 79.7%. In the sample with the addition of asparagine the percentage of NGA2F+NGA2F-GlcNac was increased to 80.5% (0.4 g/L of asparagine), 82.1% (0.8 g/L of asparagine), and 84.1% (1.6 g/L of asparagine), for a total increase of 4.4%. The percentage of NA1F+NA2F in the control sample (without asparagine addition) was as high as 9.7% (FIG. 38B). In the sample with the addition of asparagine the percentage of NA1F+NA2F was decreased to 9.4% (0.4 g/L of asparagine), 9.6% (0.8 g/L of asparagine), and 8.5% (1.6 g/L of asparagine), for a total reduction of 1.2%. Again, the percentage of Mannose type glycans was also decreased with the supplementation of asparagine. The percentage of Mannoses in the control sample (without asparagine addition) was as high as 10.6% (FIG. 38B). In the sample with the addition of asparagine the percentage of Mannoses was decreased to 10.1% (0.4 g/L of asparagine), 8.3% (0.8 g/L of asparagine), and 7.4% (1.6 g/L of asparagine), for a total reduction of 3.2%.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. Furthermore, the strategies described herein can be easily implemented either in-process or ad hoc to control the oligosaccharide distribution, thus reducing the potential impact of raw material changes. For example, Adalimumab production strategies can use these techniques to achieve maximized cell growth and specific productivity without compromising product quality.

Patents, patent applications, publications, product descriptions, GenBank Accession Numbers, and protocols that may be cited throughout this application, the disclosures of which are incorporated herein by reference in their entireties for all purposes. For example, but not by way of limitation, patent applications designated by the following attorney docket numbers are incorporated herein by reference in their entireties for all purposes: 082254.0104; 082254.0235; 082254.0236; 082254.0238; and 082254.0242.

What is claimed is:

1. A method for controlling the oligosaccharide distribution of a recombinantly-expressed immunoglobulin comprising supplementing during a production stage a cell culture media used in the recombinant expression of said immunoglobulin with a yeast hydrolysate supplement and/or a plant hydrolysate supplement to achieve a yeast hydrolysate concentration in the media of at least 11 g/L and/or a plant hydrolysate concentration of at least 7 g/L and assessing the oligosaccharide distribution of the recombinantly-expressed immunoglobulin, thereby controlling the oligosaccharide distribution of the recombinantly-expressed immunoglobulin, wherein the level of agalactosyl fucosylated biantennary oligosaccharides (sum of NGA2F and NGA2F-G1cNac) present on the recombinantly-expressed immunoglobulin is decreased as compared to the level of agalactosyl fucosylated biantennary oligosaccharides (sum of NGA2F and NGA2F-G1cNac) of the immunoglobulin recombinantly-expressed in cell culture media which is not supplemented with said yeast hydrolysate supplement and/or said plant hydrolysate supplement during the production stage; and/or wherein the level of galactose containing fucosylated biantennary oligossacharides (sum of NA1F and NA2F) present on the recombinantly-expressed immunoglobulin is increased as compared to the level of galactose containing fucosylated biantennary oligossacharides (sum of NA1F and NA2F) of the immunoglobulin recombinantly-expressed in cell culture media which is not supplemented with said yeast hydrolysate supplement and/or said plant hydrolysate supplement during the production stage.

2. The method of claim 1, wherein the immunoglobulin is an anti-TNFα antibody.

3. The method of claim 2, wherein the anti-TNFα antibody is adalimumab.

4. The method of claim 3, wherein the method produces at least 2.0 g/L of adalimumab.

5. The method of claim 1, wherein the yeast hydrolysate supplement is selected from the group consisting of Bacto TC Yeastolate, HyPep Yeast Extract, and UF Yeast Hydrolysate.

6. The method of claim 1, wherein the plant hydrolysate supplement is selected from the group consisting of a soy hydrolysate, a wheat hydrolysate, a rice hydrolysate, a cotton seed hydrolysate, a pea hydrolysate, a corn hydrolysate and a potato hydrolysate.

7. The method of claim 1, wherein the cell culture media is supplemented with a sufficient amount of the plant hydrolysate supplement to achieve a plant hydrolysate concentration of 7 g/L to 15 g/L.

8. The method of claim 7, wherein the cell culture media is supplemented with a sufficient amount of the plant hydrolysate supplement to achieve a plant hydrolysate concentration of 10 g/L to 15 g/L.

9. The method of claim 1, wherein the cell culture media is supplemented with a sufficient amount of the yeast hydrolysate supplement and the plant hydrolysate supplement to achieve a yeast hydrolysate to plant hydrolysate ratio of 0.25 to 1.55.

10. The method of any one of claims 1 or 3, wherein assessing the oligosaccharide distribution of the recombinantly-expressed immunoglobulin or adalimumab comprises assessing the level of agalactosyl fucosylated biantennary oligosaccharides (sum of NGA2F and NGA2F-G1cNac) present on the recombinantly-expressed immunoglobulin or adalimumab.

11. The method of any one of claims 1 or 3, wherein 64%-89% of the total N-linked oligosaccharides present on the immunoglobulin or adalimumab are of an agalactosyl fucosylated biantennary oligosaccharide (sum of NGA2F and NGA2F-G1cNac) form.

12. The method of any one of claims 1 or 3, wherein 64%-69% of the total N-linked oligosaccharides present on the immunoglobulin or adalimumab are of an agalactosyl fucosylated biantennary oligosaccharide (sum of NGA2F and NGA2F-G1cNac) form.

13. The method of any one of claim 1 or 3, wherein assessing the oligosaccharide distribution of the recombinantly-expressed immunoglobulin or adalimumab comprises assessing the level of galactose containing fucosylated biantennary oligossacharides (sum of NA1F and NA2F) on the recombinantly-expressed immunoglobulin or adalimumab.

14. The method of any one of claims 1 or 3, wherein 8%-31% of the total N-linked oligosaccharides present on the immunoglobulin or adalimumab are of a galactose containing fucosylated biantennary oligossacharide (sum of NA1F and NA2F) form.

15. The method of any one of claims 1 or 3, wherein 29%-31% of the total N-linked oligosaccharides present on the immunoglobulin or adalimumab are of a galactose containing fucosylated biantennary oligossacharide (sum of NA1F and NA2F) form.

16. The method of claim 1, wherein the method is a fed batch process.

17. The method of any one of claims 1 or 3, further comprising collecting and isolating the produced immunoglobulin or adalimumab.

18. The method of any one of claims 1 or 3, wherein the production stage initiates at an initial viable cell density of approximately $0.5 \times 10^6$ cells/mL.

19. The method of any one of claim 1 or 3, wherein the recombinantly-expressed immunoglobulin or adalimumab is expressed in a mammalian cell.

20. The method of claim 19, wherein the mammalian cell is a CHO cell.

21. The method of any one of claim 1 or 3, wherein the oligosaccharide distribution of the recombinantly-expressed immunoglobulin or adalimumab is assessed after the recombinantly-expressed immunoglobulin or adalimumab has been harvested from the cell culture media.

22. A method for controlling the oligosaccharide distribution of recombinantly-expressed adalimumab comprising supplementing a cell culture media used in the recombinant expression of said adalimumab with a yeast hydrolysate supplement and/or a plant hydrolysate supplement and assessing the oligosaccharide distribution of the recombinantly-expressed adalimumab, wherein the method produces at least 2.5 g/L of adalimumab, thereby controlling the oligosaccharide distribution of said adalimumab, wherein the level of agalactosyl fucosylated biantennary oligosaccharides (sum of NGA2F and NGA2F-G1cNac) present on the recombinantly-expressed adalimumab is decreased as compared to the level of agalactosyl fucosylated biantennary oligosaccharides (sum of NGA2F and NGA2F-G1cNac) of adalimumab recombinantly-expressed in cell culture media which is not supplemented with said yeast hydrolysate supplement and/or said plant hydrolysate supplement; and/or wherein the level of galactose containing fucosylated biantennary oligossacharides (sum of NA1F and NA2F) present on the recombinantly-expressed adalimumab is increased as compared to the level of galactose containing fucosylated biantennary oligossacharides (sum of NA1F and NA2F) of adalimumab recombinantly-expressed in cell culture media which is not supplemented with said yeast hydrolysate supplement and/or said plant hydrolysate supplement.

23. A method for controlling the oligosaccharide distribution of recombinantly-expressed adalimumab comprising supplementing a cell culture media used in the recombinant expression of said adalimumab with a yeast hydrolysate supplement and/or a plant hydrolysate supplement, wherein the level of agalactosyl fucosylated biantennary oligosaccharides (sum of NGA2F and NGA2F-G1cNac) present on the recombinantly-expressed adalimumab is decreased as compared to the level of agalactosyl fucosylated biantennary oligosaccharides (sum of NGA2F and NGA2F-G1cNac) of adalimumab recombinantly-expressed in cell culture media which is not supplemented with said yeast hydrolysate supplement and/or said plant hydrolysate supplement, and wherein 66%-69% of the total N-linked oligosaccharides present on the recombinantly-expressed adalimumab are of an agalactosyl fucosylated biantennary oligosaccharide (sum of NGA2F and NGA2F-G1cNac) form, thereby controlling the oligosaccharide distribution of said adalimumab.

24. A method for controlling the oligosaccharide distribution of recombinantly-expressed adalimumab comprising supplementing a cell culture media used in the recombinant expression of said adalimumab with a yeast hydrolysate supplement and/or a plant hydrolysate supplement, wherein the level of galactose containing fucosylated biantennary oligossacharides (sum of NA1F and NA2F) present on the recombinantly-expressed adalimumab is increased as compared to the level of galactose containing fucosylated biantennary oligossacharides (sum of NA1F and NA2F) of adalimumab recombinantly-expressed in cell culture media which is not supplemented with said yeast hydrolysate supplement and/or said plant hydrolysate supplement, and wherein 29%-31% of the total N-linked oligosaccharides present on the recombinantly-expressed adalimumab are of a galactose containing fucosylated biantennary oligossacharide (sum of NA1F and NA2F) form, thereby controlling the oligosaccharide distribution of said adalimumab.

25. The method of any one of claim 22, 23 or 24, wherein the yeast hydrolysate supplement is selected from the group consisting of Bacto TC Yeastolate, HyPep Yeast Extract, and UF Yeast Hydrolysate.

26. The method of any one of claim 22, 23 or 24, wherein the plant hydrolysate supplement is selected from the group consisting of a soy hydrolysate, a wheat hydrolysate, a rice hydrolysate, a cotton seed hydrolysate, a pea hydrolysate, a corn hydrolysate and a potato hydrolysate.

27. The method of any one of claim 22, 23 or 24, wherein the cell culture media is supplemented with a sufficient amount of a yeast hydrolysate supplement and/or a plant hydrolysate supplement to achieve a yeast hydrolysate concentration in the media of at least 11 g/L and/or a plant hydrolysate concentration of at least 7 g/L.

28. The method of claim 27, wherein the cell culture media is supplemented with a sufficient amount of the plant hydrolysate supplement to achieve a plant hydrolysate concentration of 7 g/L to 15 g/L.

29. The method of claim 28, wherein the cell culture media is supplemented with a sufficient amount of the plant hydrolysate supplement to achieve a plant hydrolysate concentration of 10 g/L to 15 g/L.

30. The method of any one of claim 22, 23 or 24, wherein the cell culture media is supplemented with a sufficient amount of the yeast hydrolysate supplement and the plant hydrolysate supplement to achieve a yeast hydrolysate to plant hydrolysate ratio of 0.25 to 1.55.

31. The method of any one of claim 22, 23 or 24, wherein the method is a fed batch process.

32. The method of any one of claim 22, 23 or 24, further comprising collecting and isolating the produced adalimumab.

33. The method of claim 22, wherein assessing the oligosaccharide distribution of the recombinantly-expressed adalimumab comprises assessing the level of agalactosyl fucosylated biantennary oligosaccharides (sum of NGA2F and NGA2F-G1cNac) present on the recombinantly-expressed adalimumab.

34. The method of claim 22, wherein 64%-89% of the total N-linked oligosaccharides present on the adalimumab are of an agalactosyl fucosylated biantennary oligosaccharide (sum of NGA2F and NGA2F-G1cNac) form.

35. The method of claim 22, wherein 64%-69% of the total N-linked oligosaccharides present on the adalimumab are of an agalactosyl fucosylated biantennary oligosaccharide (sum of NGA2F and NGA2F-G1cNac) form.

36. The method of claim 22, wherein assessing the oligosaccharide distribution of the recombinantly-expressed adalimumab comprises assessing the level of galactose containing fucosylated biantennary oligossacharides (sum of NA1F and NA2F) on the recombinantly-expressed adalimumab.

37. The method of claim 22, wherein 8%-31% of the total N-linked oligosaccharides present on the adalimumab are of a galactose containing fucosylated biantennary oligossacharide (sum of NA1F and NA2F) form.

38. The method of claim 22, wherein 29%-31% of the total N-linked oligosaccharides present on the adalimumab are of a galactose containing fucosylated biantennary oligossacharide (sum of NA1F and NA2F) form.

39. The method of any one of claim 22, 23 or 24, wherein the recombinantly-expressed adalimumab is expressed in a mammalian cell.

40. The method of claim 39, wherein the mammalian cell is a CHO cell.

41. The method of any one of claim 22, 23 or 24, wherein the oligosaccharide distribution of the recombinantly-expressed adalimumab is assessed after the recombinantly-expressed adalimumab has been harvested from the cell culture media.

* * * * *